US006555691B2

(12) United States Patent
Uchida et al.

(10) Patent No.: US 6,555,691 B2
(45) Date of Patent: Apr. 29, 2003

(54) COLOR DEVELOPING AGENT, AZO DYE, SILVER HALIDE PHOTOGRAPHIC LIGHT-SENSITIVE MATERIAL, AND IMAGE-FORMING METHOD

(75) Inventors: Osamu Uchida, Minami-ashigara (JP); Yasuhiro Ishiwata, Minami-ashigara (JP); Takayuki Ito, Minami-ashigara (JP); Nobutaka Fukagawa, Minami-ashigara (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/911,727

(22) Filed: Jul. 25, 2001

(65) Prior Publication Data

US 2002/0146651 A1 Oct. 10, 2002

(30) Foreign Application Priority Data

Jul. 25, 2000 (JP) ....................................... 2000-224547
Jul. 25, 2000 (JP) ....................................... 2000-224563
Feb. 16, 2001 (JP) ....................................... 2001-040774

(51) Int. Cl.[7] ............................................. C07D 271/07
(52) U.S. Cl. ....................................................... 548/133
(58) Field of Search .......................................... 548/133

(56) References Cited

U.S. PATENT DOCUMENTS 3,932,380 A 1/1976 Krutak, Sr. et al. .......... 260/197
4,473,672 A 9/1984 Bottrill ........................ 523/215
5,874,203 A 2/1999 Morita et al. ................ 430/380
5,976,756 A 11/1999 Nakamura et al. .......... 430/203
2002/0039708 A1 * 4/2002 Katoh et al. ................ 430/350

OTHER PUBLICATIONS

Yousif, Chemical Abstracts, 117:212402, 1992.*

* cited by examiner

*Primary Examiner*—Fiona T. Powers
(74) *Attorney, Agent, or Firm*—Birch, Stewart, Kolasch & Birch, LLP

(57) ABSTRACT

A color-developing agent of the formula (1-1):

formula (1-1)

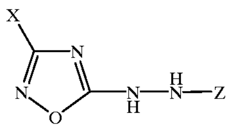

wherein X represents a hydrogen atom or a substituent, and Z represents a carbamoyl, acyl, alkoxycarbonyl, or aryloxycarbonyl group. An azo dye of the formula (2-1):

formula (2-1)

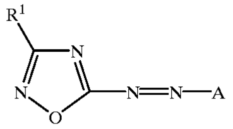

wherein $R^1$ represents a hydrogen atom or a substituent, and A represents a group of atoms necessary to form the azo dye by the compound of formula (2-1). A silver halide photographic light-sensitive material containing any of the color-developing agent and the azo dye in at least one photographic constitutional layer.

7 Claims, 1 Drawing Sheet

COLOR DEVELOPING AGENT, AZO DYE, SILVER HALIDE PHOTOGRAPHIC LIGHT-SENSITIVE MATERIAL, AND IMAGE-FORMING METHOD

FIELD OF THE INVENTION

The present invention relates to a novel color-developing agent, and a silver halide photographic light-sensitive material and image-forming method using the color-developing agent. More specifically, the present invention relates to a silver halide photographic light-sensitive material and image-forming method good in color-forming property at the time of development.

Further, the present invention relates to a novel 1,2,4-oxadiazolyl azo dye, which exhibits excellent absorption characteristics, and which is high in fastness to light, heat, humidity, air, chemicals and the like.

Further, the present invention relates to a silver halide color light-sensitive material containing an image-forming compound containing the novel 1,2,4-oxadiazolyl azo dye or a precursor thereof.

BACKGROUND OF THE INVENTION

In a color photographic light-sensitive material, when the light-sensitive material is exposed to light and thereafter subjected to color-development, the resultant oxidized color-developing agent reacts with a coupler, to form a dye image.

The color-development is attained, for example, by dipping an exposed light-sensitive material in an aqueous alkaline solution (a developing solution) in which a color-developing agent is dissolved. However, this technique have many problems, for example, a problem that the developing solution tends to be deteriorated with the lapse of time and problems concerning treatments of developing solution wastes.

As one measure to solve above problems, a method wherein an aromatic primary amine developing agent or its precursor is built in the hydrophilic colloid layer of a light-sensitive material is proposed. Further, a method wherein a sulfonylhydrazine-type developing agent is built in the hydrophilic colloid layer of a light-sensitive material is proposed. Examples of these include methods described, for example, in U.S. Pat. No. 803,783, JP-B-58-14671 ("JP-B" means examined Japanese patent publication), European Patent Nos. 545 491(A1) and 565 165(A1).

However, even these methods cannot attain satisfactory color formation when color-developed; and there is the problem of storage stability of the light-sensitive material.

In the fields of silver halide photographic light-sensitive materials, a so-called color diffusion transfer method in which a diffusible dye is formed imagewise on a light-sensitive material and the image is transferred and fixed to an image-receiving material, to form a color image, is a known technique, and many proposals concerned this have been made. In these methods, a compound (a preformed dye) obtained by causing an image-forming dye, which is beforehand colored to have nondiffusibility (the compound will be referred to as a colorant hereinafter), is generally used. Therefore, when the colorant is added to the same layer containing a silver halide emulsion, an undesired drop in the sensitivity to exposure is caused, because of a filter effect of the dye moiety. In order to improve these drawbacks, a so-called coupling system is proposed in U.S.

Pat. No. 4,469,773 and JP-B-63-36487 in which system a dye is formed by a coupling reaction between an oxidized product of a developing agent, which is produced as a function of the developing of silver halide, and a coupler. However, the color-developing agent described therein has a difficulty in the compatibility of the storage stability and the activity of the coupling reaction and a difficulty in modifying both the color-developing agent and the coupler to those having resistance to diffusion.

Novel color-developing agents are proposed in JP-A-09-152702 ("JP-A" means unexamined published Japanese patent application) and JP-A-09-152705. In these methods, however, sufficient color-forming property is not obtained yet. Also, whether or not there are problems concerning the hue and color image stability of a dye to be formed.

Hitherto, color diffusion transfer photography, using an azo dye image-forming compound that can supply an azo dye having a diffusibility different from the image-forming compound itself, as a result of development under a basic condition, has been widely known. For example, image-forming compounds that release a yellow dye are described in JP-A-52-7727 and JP-A-54-79031, and U.S. Pat. No. 4,473,672. Also, image-forming compounds that release a magenta dye are described, for example, in JP-A-49-114424, JP-A-4-331954, and U.S. Pat. No. 3,932,380

However, these yellow and magenta dye image-forming compounds have insufficient spectral characteristics of the resultant dye resulting in problems in color reproducibility, or they have low fastness to light, heat, air, chemicals, and the like. Thus, yellow or magenta dye image-forming compounds satisfying all performance requirements have not yet been found, and further improvement has been desired.

SUMMARY OF THE INVENTION

The present invention is a color-developing agent represented by the following formula (1-1):

formula (1-1)

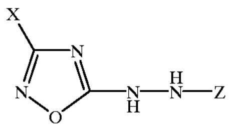

wherein X represents a hydrogen atom or a substituent, and Z represents a carbamoyl, acyl, alkoxycarbonyl, or aryloxycarbonyl group.

Further the present invention is a silver halide photographic light-sensitive material, which contains at least one color-developing agent represented by the formula (1-1) on a support.

Further, the present invention is an image-forming method, which comprises the step of subjecting the silver halide photographic light-sensitive material to heat-development.

Further, the present invention is an image-forming method, which comprises the step of subjecting the silver halide photographic light-sensitive material to development, under generation of an alkali by a slightly soluble metal salt and a complexing agent of the metal salt.

Further, the present invention is an image-forming method, which comprises the step of subjecting the silver halide photographic light-sensitive material to development by developing an alkaline processing solution.

Further, the present invention is an azo dye represented by the following formula (2-1):

formula (2-1)

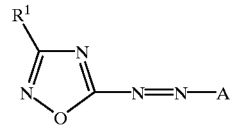

wherein $R^1$ represents a hydrogen atom or a substituent, and A represents a group of atoms necessary for formation of the azo dye by the compound of the formula (2-1).

Further, the present invention is a silver halide photographic light-sensitive material, which contains the azo dye represented by the formula (2-1).

Further, the present invention is a silver halide color photographic light-sensitive material, which contains at least one dye-forming compound represented by the following formula (2-5) on a support:

$$(Dye)_q\text{-}X^1\text{—}Y \qquad \text{formula (2-5)}$$

wherein Dye represents an azo dye represented by the formula (2-1) or azo dye precursor thereof, $X^1$ represents a single bond or a connecting group which is cleaved in correspondence to or in inverse correspondence to development, Y represents a group which has a nature of generating a difference in diffusibility of the dye component in correspondence to or in inverse correspondence to reaction of a light-sensitive silver salt having a latent image imagewise, Dye is bonded to $X^1$ at a position or positions of at least one of $R^1$ and A in the formula (2-1), q is 1 or 2, and when q is 2, Dye's may be the same or different.

Other and further features and advantages of the invention will appear more fully from the following description, taken in connection with the accompanying drawing.

DETAILED DESCRIPTION OF THE INVENTION

Figure 1:
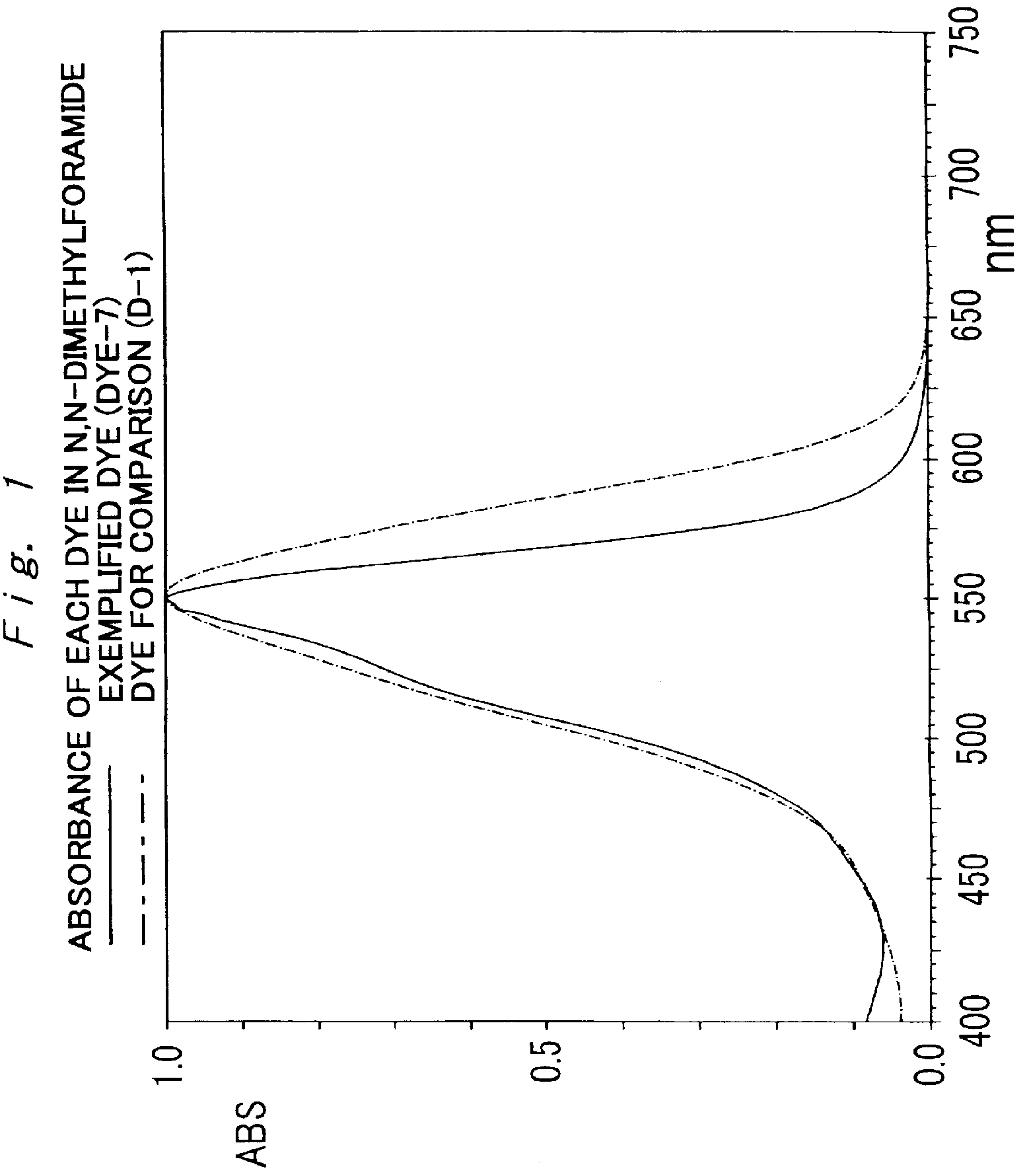
FIG. 1 is a graph showing absorbances of the exemplified dye (DYE-7) according to the present invention and the dye for comparison (D-1) in N,N-dimethylformamide.

According to the present invention there is provided the following means.

(1) A color-developing agent, represented by the following formula (1-1):

formula (1-1)

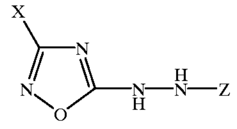

wherein X represents a hydrogen atom or a substituent, and Z represents a carbamoyl, acyl, alkoxycarbonyl, or aryloxycarbonyl group.

(2) The color-developing agent according to item (1), wherein X in the formula (1-1) is a substituent having at least one selected from the group consisting of —COOH, $—NHSO_2R$, $—SO_2NHR$, $—SO_2NHCOR$, $—CONHSO_2R$, $—NHCONHSO_2R$, $—SO_2NHCONRR$, —OH and —SH, in which R represents an alkyl, aryl or aromatic heterocyclic group which may be substituted, and R's may be the same or different from each other and may bond together to form a ring.

(3) The color-developing agent according to item (1), wherein Z in the formula (1-1) is a carbamoyl group, in which the nitrogen atom on the carbamoyl group has at least one hydrogen atom.

(4) A silver halide photographic light-sensitive material, containing at least one color-developing agent represented by the formula (1-1) on a support.

(5) An image-forming method, comprising the step of subjecting the silver halide photographic light-sensitive material according to item (4) to heat-development.

(6) An image-forming method, comprising the step of subjecting the silver halide photographic light-sensitive material according to item (4) to development under generation of an alkali by a metal salt that is hardly soluble in water and a completing agent for the metal salt.

(7) An image-forming method, comprising the step of subjecting the silver halide photographic light-sensitive material according to item (4) to development by developing an alkaline processing solution.

(Hereinafter, the color-developing agents described in the above (1) to (3), the silver halide photographic light-sensitive material described in the above (4), and the image-forming method described in the above (5) to (7) are collectively referred to as the first embodiment of the present invention.)

(8) An azo dye, represented by the following formula (2-1):

formula (2-1)

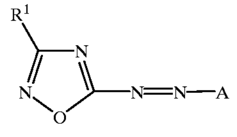

wherein $R^1$ represents a hydrogen atom or a substituent, and A represents a group of atoms necessary to form the azo dye by the compound of the formula (2-1).

(9) The azo dye according to item (8), wherein A in the formula (2-1) is a group represented by the following formula (2-2):

formula (2-2)

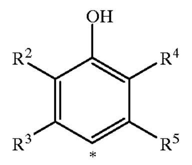

wherein $R^2$, $R^3$, $R^4$ and $R^5$ each represents a hydrogen atom or a substituent, and $R^2$ and $R^3$ and/or $R^4$ and $R^5$ may bond together to form a ring, and * represents a position which is bonded to the azo moiety in the formula (2-1).

(10) The azo dye according to item (8), wherein A in the formula (2-1) is a group represented by the following formula (2-3):

formula (2-3)

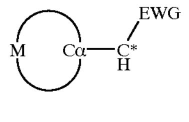

wherein Cα represents a carbon atom, EWG represents a cyano, carbamoyl or alkoxycarbonyl group, M represents a group of atoms necessary to form together with the Cα a 5- or 6-memebered aromatic heteroring, and * represents a position which is bonded to the azo moiety in the formula (2-1).

(11) The azo dye according to item (8), wherein A in the formula (2-1) is a group represented by the following formula (2-4):

formula (2-4)

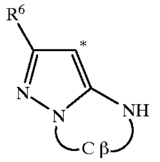

wherein $R^6$ represents a hydrogen atom or a substituent, Cβ represents a group of atoms necessary to form together with the N—C—NH a 5- or 6-memebered aromatic heteroring, and * represents a position which is bonded to the azo moiety in the formula (2-1).

(12) A silver halide photographic light-sensitive material, containing the azo dye represented by the formula (2-1) in item (8).

(13) A silver halide color photographic light-sensitive material, containing at least one dye-forming compound represented by the following formula (2-5) on a support:

$(Dye)_q$-$X^1$—Y formula (2-5)

wherein Dye represents the azo dye represented by the formula (2-1) in item (8) or azo dye precursor thereof, $X^1$ represents a single bond or a connecting group which is cleaved in correspondence to or in inverse correspondence to development, Y represents a group which has a nature of generating a difference in diffusibility of the dye component in correspondence to or in inverse correspondence to reaction of a light-sensitive silver salt having a latent image imagewise, Dye is bonded to $X^1$ at a position or positions of at least one of $R^1$ and A in the formula (2-1) in item (8), q is 1 or 2, and when q is 2, Dye's may be the same or different.

(Hereinafter, the azo dyes described in the above (8) to (11), the silver halide photographic light-sensitive material described in the above (12), and the silver halide color photographic light-sensitive material described in the above (13) are collectively referred to as the second embodiment of the present invention.)

Herein, the present invention means to include both the first embodiment and the second embodiment, unless otherwise specified.

In the present invention, the color-developing agent represented by the formula (1-1) is preferable as a raw material to obtain the azo dye represented by the formula (2-1).

Further, an example of an azo dye preferable in the present invention include the azo dye represented by the formula (2-1) obtainable by coupling reaction of an oxidation product of the color-developing agent represented by the formula (1-1) with a coupler.

The following will describe the compound represented by the formula (1-1) and used in the present invention in detail.

Examples of the substituent represented by X in the formula (1-1) include halogen atoms, alkyl (including cycloalkyl and bicycloalkyl), alkenyl (including cycloalkenyl and bicycloalkenyl), alkynyl, aryl, heterocyclic, cyano, hydroxyl, nitro, carboxyl, alkoxy, aryloxy, silyloxy, heterocylic oxy, acyloxy, carbamoyloxy, alkoxycarbonyloxy, aryloxycarbonyloxy, amino (including anilino), acylamino, aminocarbonylamino, alkoxycarbonylamino, aryloxycarbonylamino, sulfamonylamino, alkyl- and arylsulfonylamino, mercapto, alkylthio, arylthio, heterocyclic thio, sulfamoyl, sulfo, alky- and aryl-sulfinyl, alkyl- and aryl-sulfonyl, acyl, aryloxycarbonyl, alkoxycarbonyl, carbamoyl, arylazo, heterocyclic azo, imido, phosphino, phosphinyl, phosphinyloxy, phosphinylamino, and silyl groups.

More specifically, examples of the substituent represented by X include halogen atoms (such as fluorine, chlorine, bromine and iodine atoms), noncyclic alkyl (preferably, alkyl having 1–30 carbon atoms, such as methyl, ethyl, n-propyl, isopropyl, t-butyl, n-octyl, eicosyl, 2-chloroethyl, 2-cyanoethyl, and 2-ethylhexyl), cycloalklyl (preferably, substituted or unsubstituted cycloalkyl having 3–30 carbon atoms, such as cyclohexyl, cyclopentyl, and 4-n-dodecylcyclohexyl), bicycloalkyl groups (preferably, substituted or unsubstituted bicycloalkyl having 5–30 carbon atoms, that is, monovalent groups obtained by removing one hydrogen atom from bicycloalkane having 5–30 carbon atoms, such as bicyclo[1,2,2]heptane-2-yl, and bicyclo[2,2,2]octane-3-yl), and tircyclo structure and higher structures, which have a larger number of rings. An alkyl group in substituents that will be described below (for example, alkyl in alkylthio) represents an alkyl group within the scope of such a concept.

Examples of the substituent represented by X further include noncyclic alkenyl (preferably, substituted or unsubstituted alkenyl having 2–30 carbon atoms, such as vinyl, allyl, prenyl, geranyl and oleyl), cycloalkenyl (preferably, substituted or unsubstituted cycloalkenyl having 3–30 carbon atoms, that is, monovalent groups obtained by removing one hydrogen atom from cycloalkene having 3–30 carbon atoms, such as 2-cyclopentene-1-yl, and 2-cyclohexene-1-yl), bicycloalkenyl (substituted or unsubstituted bicycloalkenyl, preferably substituted or unsubstituted bicycloalkenyl having 5–30 carbon atoms, that is, monovalent groups obtained by removing one hydrogen atom from bicycloalkene having one double bond, such as bicyclo[2,2,1]hept-2-ene-1-yl, and bicyclo[2,2,2]oct-2-ene-4-yl), alkynyl (preferably, substituted or unsubstituted alkynyl having 2–30 carbon atoms, such as ethynyl, propargyl, and trimethylsilylethynyl), aryl (preferably, substituted or unsubstituted aryl having 6–30 carbon atoms, such as phenyl, p-tolyl, naphthyl, m-chlorophenyl, and o-hexadecanoylaminophenyl), heterocyclic (preferably, monovalent groups obtained by removing one hydrogen atom from 5- or 6-membered and substituted or unsubstituted and aromatic or non-aromatic heterocyclic compounds, and more preferably 5- or 6-membered and aromatic heterocyclic groups having 3–30 carbon atoms, such as 2-furyl, 2-thienyl, 2-pyrimidinyl, 2-benzothiazolyl), cyano, hydroxyl, nitro, carboxyl, alkoxy (preferably, substituted or unsubstituted alkoxy having 1–30 carbon atoms, such as methoxy, ethoxy, isopropoxy, t-butoxy, n-octyloxy, 2-methoxyethoxy), aryloxy (preferably, substituted or unsubstituted aryloxy having 6–30 carbon atoms, such as phenoxy, 2-ethylphenoxy, 4-t-butylphenoxy, and 3-nitrophenoxy, 2-tetradecanoylaminophenoxy), silyloxy (preferably, silyloxy having 3–20 carbon atoms, such as trimethylsilyloxy, and t-butyldimethylsilyloxy), heterocyclic oxy (preferably, substituted or unsubstituted heterocyclic oxy having 2–30 carbon atoms, such as 1-phenyltetrazole-5-oxy, and 2-tetrahydropyranyloxy), acyloxy (preferably, formyloxy, substituted or unsubstituted alkylcarbonyloxy having 2–30 carbon atoms, and substituted or unsubstituted arylcarbonyloxy having 6–30 carbon atoms, such as formyloxy, acetyloxy, pivaloyloxy, stearoyloxy, benzoyloxy, and p-methoxyphenylcarbonyloxy), carbamoyloxy (preferably, substituted or unsubstituted carbamoyloxy having 1–30 carbon atoms, such as N,N-dimethylcarbamoyloxy, N,N-diethylcarbamoyloxy, morpholinocarbonyloxy, N,N-di-n-octylaminocarbonyloxy, N-n-octylcarbamoyloxy), alkoxycarbonyloxy (preferably, substituted or unsubstituted alkoxycarbonyloxy having 2–30 carbon atoms, such as methoxycarbonyloxy, ethoxycarbonyloxy, t-butoxycarbonyloxy, and n-octylcarbonyloxy), aryloxycarbonyloxy (preferably, substituted or unsubstituted aryloxycarbonyloxy having 7–30 carbon atoms, such as phenoxycarbonyloxy, p-methoxyphenoxycarbonyloxy, and p-n-hexadecyloxyphenoxycarbonyloxy), amino (preferably, amino, substituted or unsubstituted alkylamino having 1–30 carbon atoms, and substituted or unsubstituted anilino having 6–30 carbon atoms, such as amino, methylamino, dimethylamino, anilino, N-methyl-anilino, and diphenylamino), acylamino (preferably, formylamino, substituted or unsubstituted alkylcarbonylamino having 1–30 carbon atoms, and substituted or unsubstituted arylcarbonylamino having 6–30 carbon atoms, such as formylamino, acetylamino, pyvaroylamino, lauroylamino, benzoylamino, 3,4,5-tri-n-octyloxyphenylcarbonylamino), aminocarbonylamino (preferably, substituted or unsubstituted aminocarbonylamino having 1–30 carbon atoms, such as carbamoylamino, N,N-dimethylaminocarbonylamino, N,N-diethylaminocarbonylamino, and morpholinocarbonylamino), alkoxycarbonylamino (preferably, substituted or unsubstituted alkoxycarbonylamino having 2–30 carbon atoms, such as methoxycarbonylamino, ethoxycarbonylamino, t-butoxycarbonylamino, n-octadecyloxycarbonylamino, N-methyl-methoxycarbonylamino), aryloxycarbonylamino (preferably, substituted or unsubstituted aryloxycarbonylamino having 7–30 carbon atoms, such as phenoxycarbonylamino, p-chlorophenoxycarbonylamino, m-n-octyloxyphenoxycarbonylamino), sulfamoylamino (preferably, substituted or unsubstituted sulfamoylamino having 0–30 carbon atoms, such as sulfamoylamino, N,N-dimethylaminosulfonylamino, and N-n-octylaminosulfonylamino), alkyl- and aryl-sulfonylamino (preferably, substituted or unsubstituted alkylsulfonylamino having 1–30 carbon atoms, and substituted or unsubstituted arylsulfonylamino having 6–30 carbon atoms, such as methylsulfonylamino, butylsulfonylamino, phenylsulfonylamino, 2,3,5-trichlorophenylsulfonylamino, and p-methylphenylsulfonylamino), mercapto, alkylthio (preferably, substituted or unsubstituted alkylthio having 1–30 carbon atoms, such as methylthio, ethylthio, n-hexadecylthio), arylthio (preferably, substituted or unsubstituted arylthio having 6–30 carbon atoms, such as phenylthio, and p-chlorophenylthio, m-methoxyphenylthio), heterocyclic thio (preferably, substituted or unsubstituted heterocyclic thio having 2–30 carbon atoms, such as 2-benzothiazolylthio, and 1-phenyltetrazole-5-ylthio), sulfamoyl (preferably, substituted or unsubstituted sulfamoyl having 0–30 carbon atoms, such as N-ethylsulfamoyl, N-(3-dodecyloxypropyl)sulfamoyl, N,N-dimethylsulfamoyl, N-acetylsulfamoyl, N-benzoylsulfamoyl, and N-(N'-phenylcarbamoyl)sulfamoyl), sulfo, alkyl- and aryl-sulfinyl (preferably, substituted or unsubstituted alkylsulfinyl having 1–30 carbon atoms, and substituted or unsubstituted arylsulfinyl having 6–30 carbon atoms, such as methylsulfinyl, ethylsulfinyl, phenylsulfinyl, and p-methylphenylsulfinyl), alkyl- and aryl-sulfonyl (preferably, substituted or unsubstituted alkylsulfonyl having 1–30 carbon atoms, and substituted or unsubstituted arylsulfonyl having 6–30 carbon atoms, such as methylsulfonyl, ethylsulfonyl, phenylsulfonyl, and p-methylphenylsulfonyl), acyl (preferably, formyl, substituted or unsubstituted alkylcarbonyl having 2–30 carbon atoms, and substituted or unsubstituted arylcarbonyl having 7–30 carbon atoms, such as acetyl, pivaloyl, 2-chloroacetyl, stearoyl, benzoyl, p-n-octyloxyphenylcarbonyl), aryloxycarbonyl (preferably, substituted or unsubstituted aryloxycarbonyl having 7–30 carbon atoms, such as phenoxycarbonyl, o-chlorophenoxycarbonyl, m-nitrophenoxycarbonyl, and p-t-butylphenoxycarbonyl), alkoxycarbonyl (preferably, substituted or unsubstituted alkoxycarbonyl having 2–30 carbon atoms, such as methoxycarbonyl, ethoxycarbonyl, t-butoxycarbonyl, and n-octadecylcarbonyl), carbamoyl (preferably, substituted or unsubstituted carbamoyl having 1–30 carbon atoms, such as carbamoyl, N-methylcarbamoyl, N,N-dimethylcarbamoyl, N,N-di-n-octylcarbamoyl, and N-(methylsulfonyl)carbamoyl), arylazo and heterocyclic azo (preferably, substituted or unsubstituted arylazo having 6–30 carbon atoms, and substituted or unsubstituted heterocyclic azo having 3–30 carbon atoms, such as phenylazo, p-chlorophenylazo, 5-ethylthio-1,3,4-thiadiazole-2-ylazo), imido (preferably, N-succimido, and N-phthalimido), phosphino (preferably, substituted or unsubstituted phosphino having 2–30 carbon atoms, such as dimethylphosphino, diphenylphosphino, and methylphenoxyphosphino), phosphinyl (preferably, substituted or unsubstituted phosphinyl having 2–30 carbon atoms, such as phosphinyl, dioctyloxyphosphinyl, and diethoxyphosphinyl), phosphinyloxy (preferably, substituted or unsubstituted phosphinyloxy having 2–30 carbon atoms, such as diphenoxyphospinyloxy, dioctyloxyphosphinyloxy), phosphinylamino (preferably, substituted or unsubstituted phosphinylamino having 2–30 carbon atoms, such as dimethoxyphosphyinylamino, and dimethylaminophosphinylamino), silyl groups (preferably, substituted or unsubstituted silyl having 3–30 carbon atoms, such as trimethylsilyl, t-butyldimethylsilyl, and phenyldimethylsilyl).

Groups having one or more hydrogen atoms, among the above-mentioned functional groups, may be removed the hydrogen atom(s) and may be further substituted with the above-mentioned group(s). Examples of such a functional group include alkylcarbonylaminosulfonyl, arylcarbonylaminosulfonyl, alkylsulfonylaminocarbonyl, and arylsulfonylaminocarbonyl groups. Specific examples thereof include methylsulfonylaminocarbonyl, p-methylphenylsulfonylaminocarbonyl, acetylaminosulfonyl, and benzoylaminosulfonyl.

Among these groups, preferred are halogen atoms, alkyl, aryl, alkylthio, alkylsulfonyl, arylthio, arylsulfonyl, cyano, carbamoyl, and sulfamoyl groups.

Alkyl and aryl groups are more preferred.

X in the formula (1-1) preferably has at least one substituent represented by —COOH, —$NHSO_2R$, —$SO_2NHR$, —$SO_2NHCOR$, —$CONHSO_2R$, —$NHCONHSO_2R$, —$SO_2NHCONRR$, —OH and —SH. The substituent represented by X may be any one of these substituents themselves.

R represents an alkyl, aryl or aromatic heterocyclic group which may be substituted, and R's may be the same or be different and may be connected to each other to form a ring.

Preferred examples of the above-mentioned substituent are —COOH, —$NHSO_2R$, —$CONHSO_2R$, and —$NHCONHSO_2R$. More preferred examples thereof are —$NHSO_2R$ and —$NHCONHSO_2R$.

Z represents a carbamoyl, acyl, alkoxycarbonyl, or aryloxycarbonyl group. Examples of these substituents are the same as described about X. Among theses groups, a carbamoyl group is preferred. A carbamoyl group wherein its nitrogen atom has a hydrogen atom(s) is particularly preferred.

As the carbamoyl group, carbamoyl having 1–50 carbon atoms is preferred, and carbamoyl having 8–40 carbon atoms is more preferred. Specific examples thereof include N-hexadecylcarbamoyl, N-octadecylcarbamoyl, N-3-(2,4-tert-pentylphenoxy)propylcarbamoyl, N-(4-dodecyloxyphenyl)carbamoyl, N-(2-chloro-5-dodecyloxycarbonylphenyl)carbamoyl, and N-naphthylcarbamoyl groups.

Examples of the color-developing agent represented by the formula (1-1) will be shown below. However, the scope of the present invention is not limited to these exemplified examples.

R-1

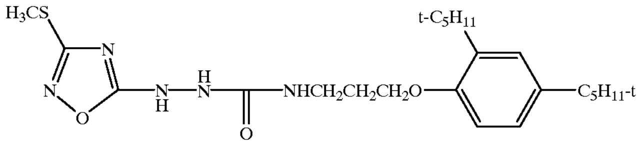

R-2

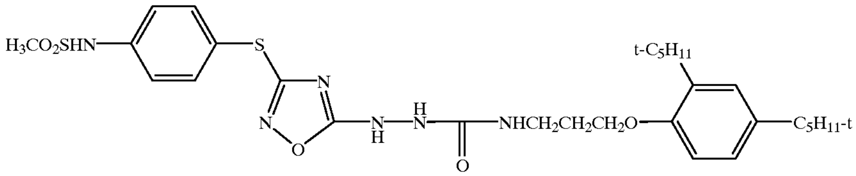

R-3

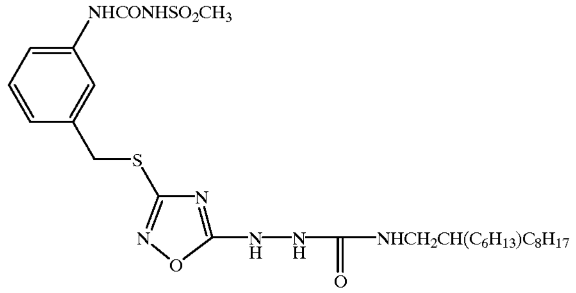

R-4

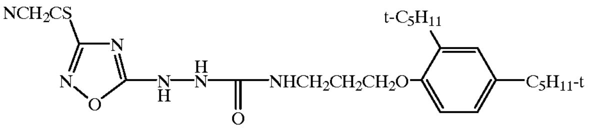

R-5

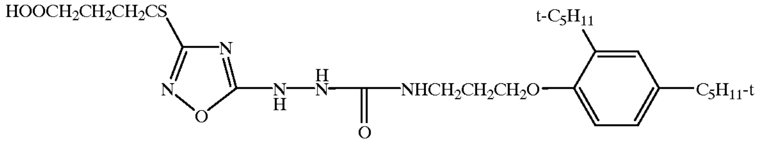

R-6

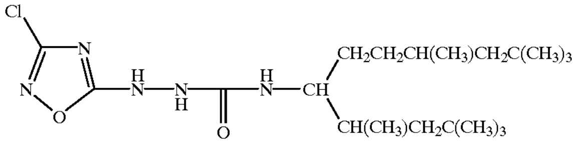

R-7

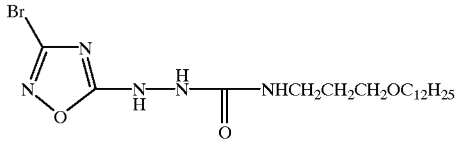

R-8

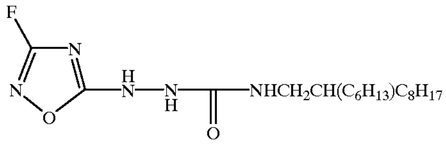

R-9

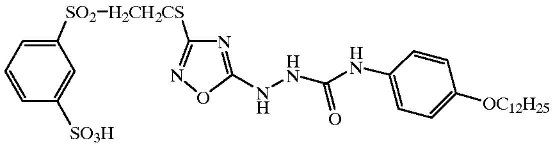

-continued
R-10
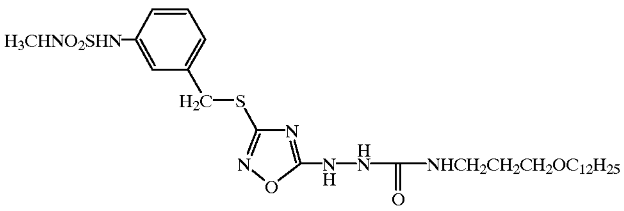
R-11
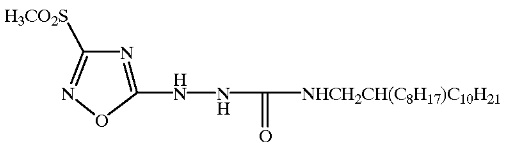
R-12
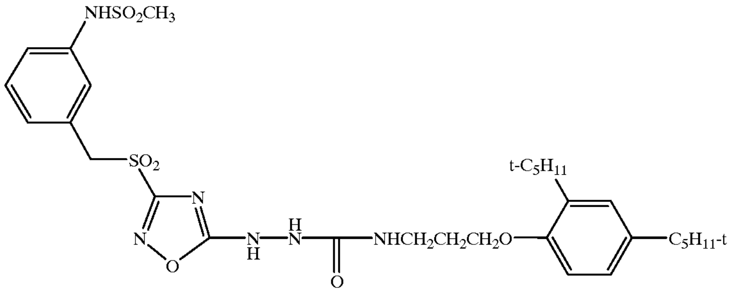
R-13
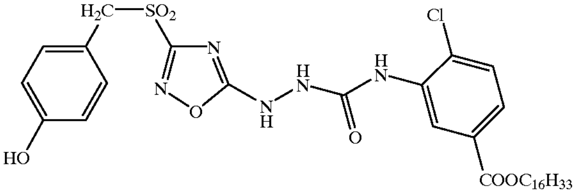
R-14
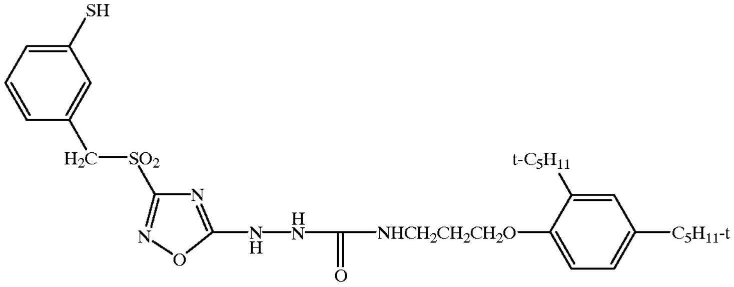
R-15
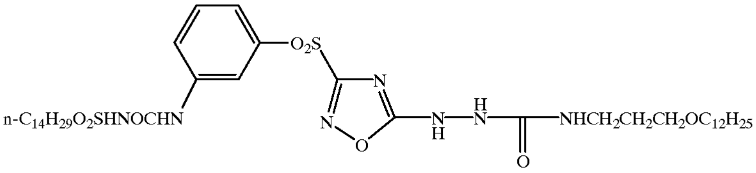

-continued
R-16
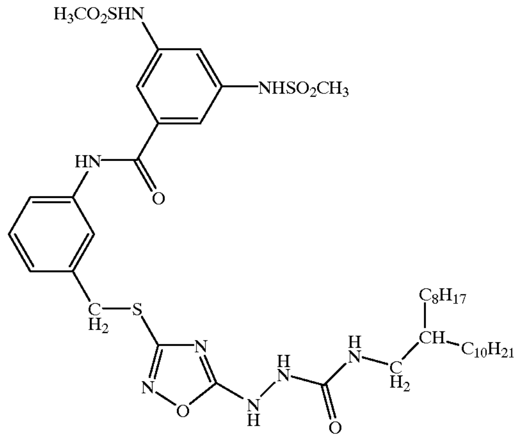
R-17
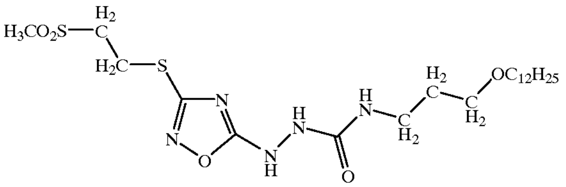
R-18
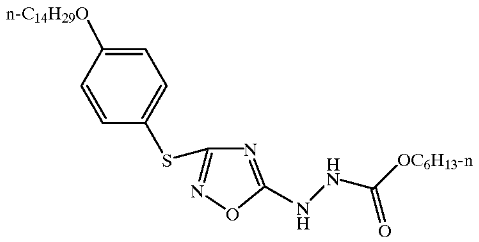
R-19
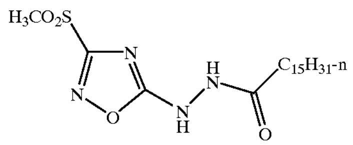
R-20
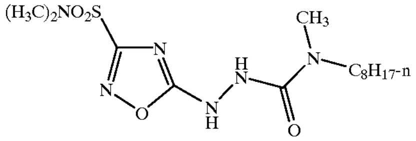
R-21
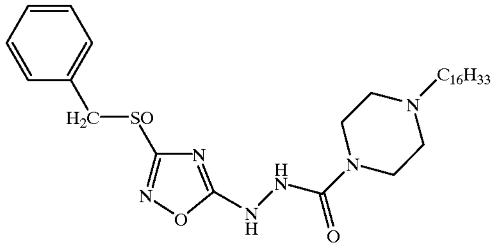
R-22
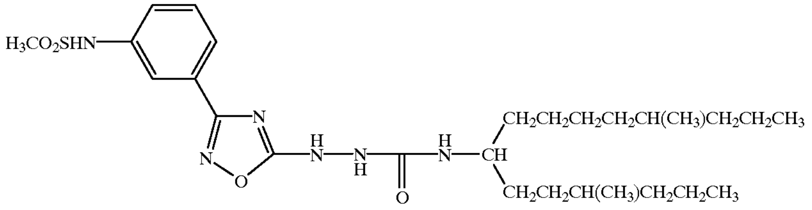
R-23
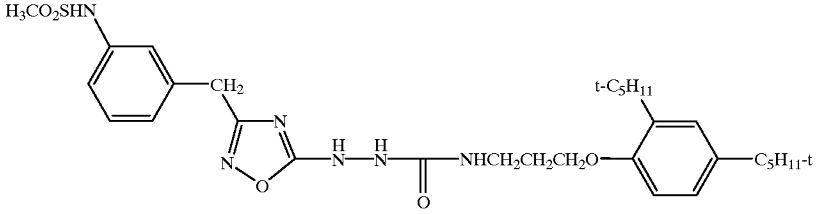

-continued
R-24
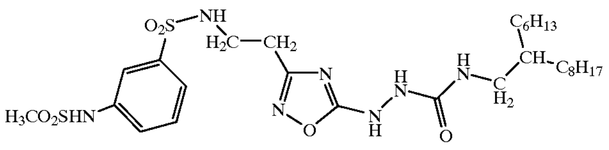
R-25
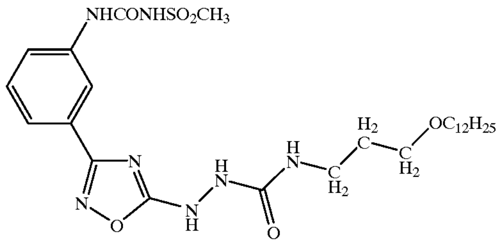
R-26
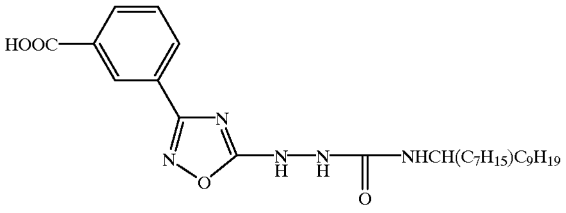
R-27
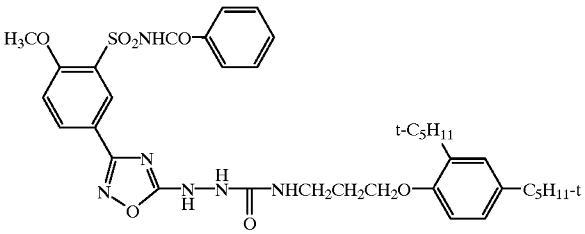
R-28
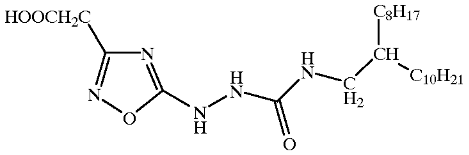
R-29
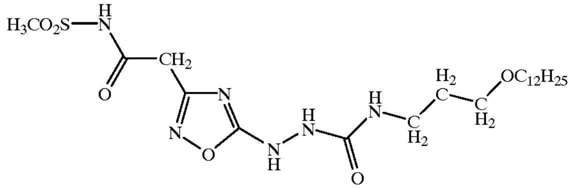
R-30
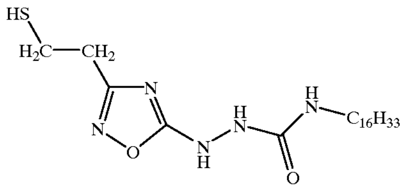
R-31
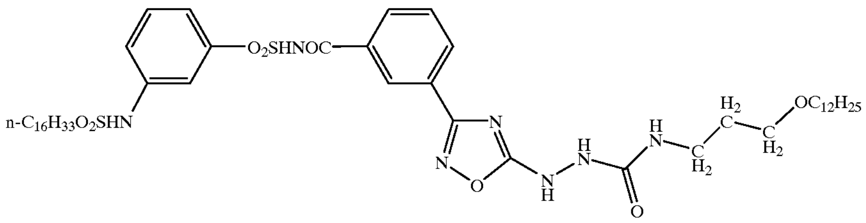
R-32
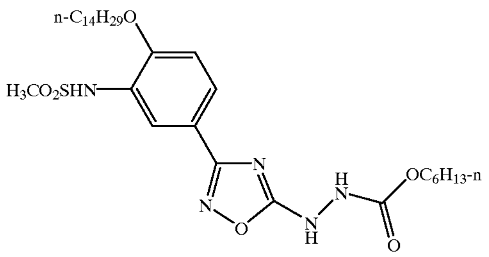
R-33
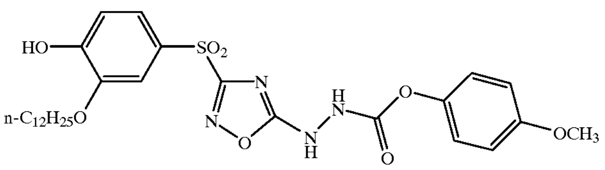

-continued
R-34
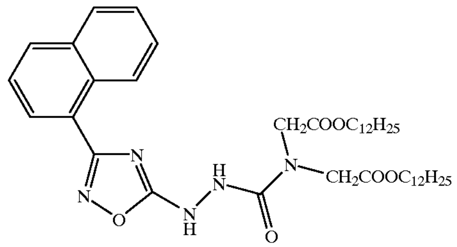
R-35
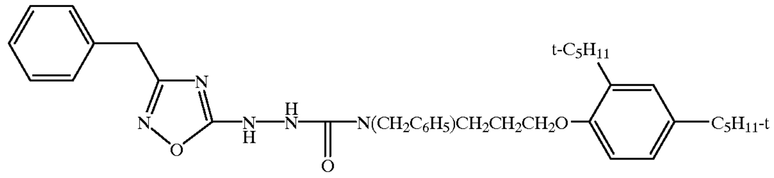
R-36
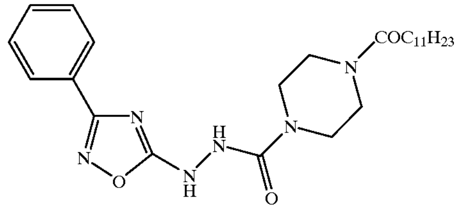
R-37
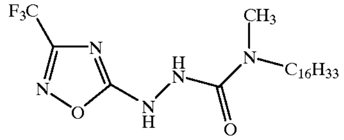
R-38
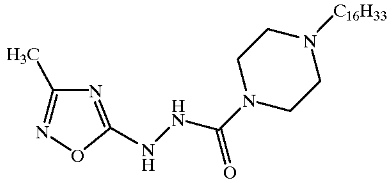
R-39
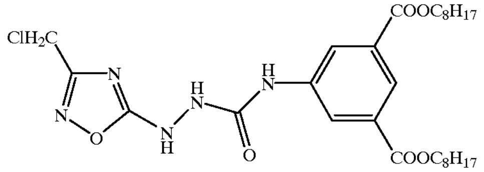
R-40
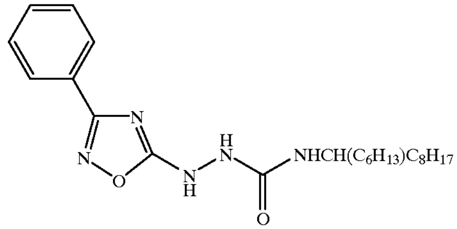
R-41
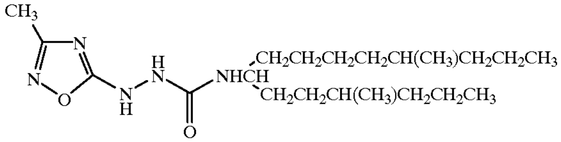
R-42
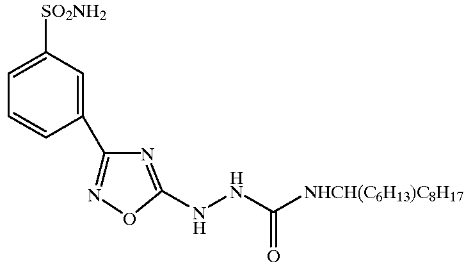
R-43
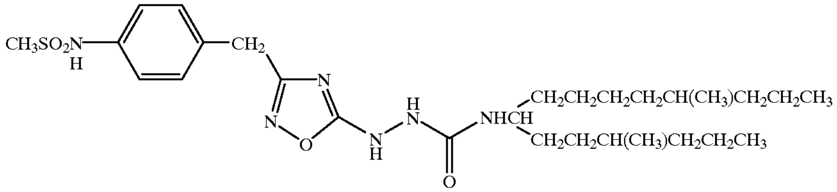

Next, a general method of synthesizing the compound of the present invention will be explained.

SYNTHETIC EXAMPLE 1

Synthesis of Exemplified Compound (R-22)

The exemplified compound (R-22) was synthesized in the following synthetic rate. Other compounds can be synthesized in the similar manner as above.

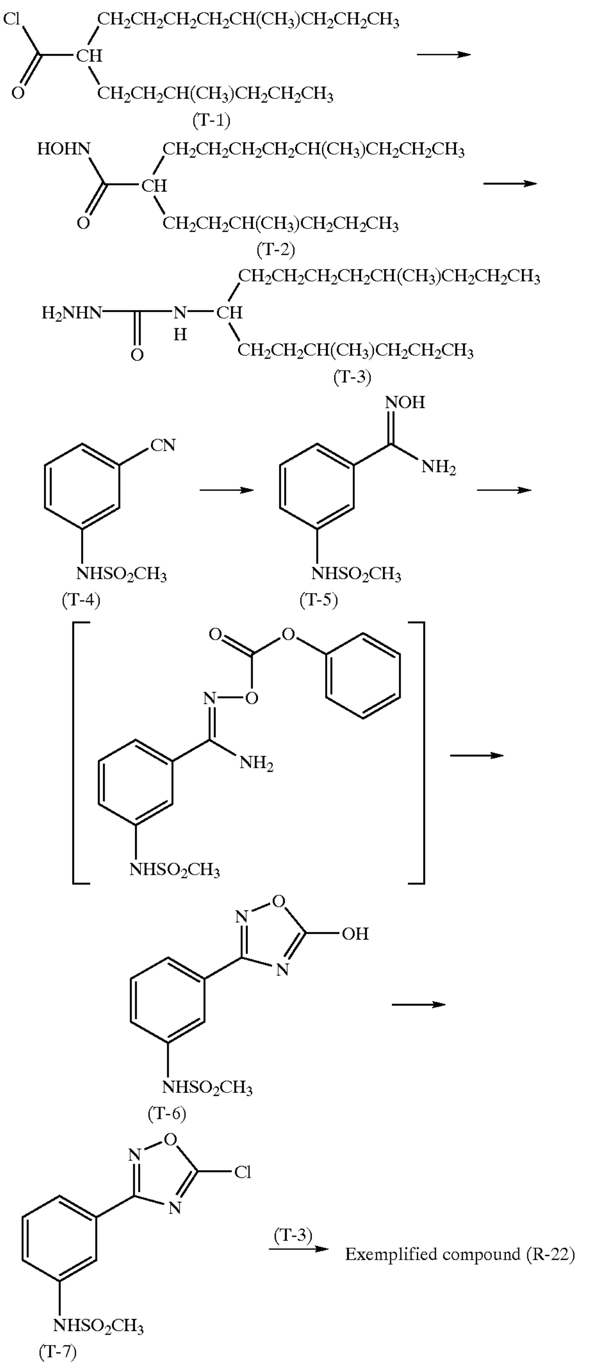

(T-1)

(T-2)

(T-3)

(T-4)

(T-5)

(T-6)

(T-7)

Exemplified compound (R-22)

Synthesis of a Compound (T-2)

Into 500 ml of acetonitrile was dissolved 152.0 g of a compound (T-1), and then 40.5 g of hydroxylamine hydrochloride was added thereto in five separate operations under cooling with ice. After the addition, 140 ml of triethylamine was dropwise added thereto in the manner that the internal temperature would be not over 20° C. After the dropwise addition, the solution was subjected to further reaction for one hour. The reaction solution was poured into 2000 ml of 0.5 N hydrochloric acid, and then precipitated crystal was collected by filtration, and was then washed with 200 ml of water. Thus, 138.7 g of the compound (T-2) was obtained as white crystal.

Synthesis of a Compound (T-3)

Into 350 ml of acetonitrile and 47.5 ml of triethylamine was dissolved 100.0 g of the compound (T-2), and then 28.1 ml of methanesulfonyl chloride was dropwise added thereto at room temperature. At this time, the reaction temperature rose from 24° C. to 32° C. After the dropwise addition, the reaction system was heated under reflux for 2 hours. After the reaction, the reaction system was cooled to room temperature and precipitated crystal was filtered. The filtrate was concentrated into an approximately half volume under reduced pressure. The residue was dropwise added to 300 ml of tetrahydrofuran dispersion solution (not completely homogenous) in which 60.5 g of water-saturated hydrazine was dispersed, which was separately prepared and vigorously stirred. At this time, the reaction temperature rose from 23° C. to 35° C. After the reaction, 600 ml of ethyl acetate and 850 ml of water were added thereto, and then an extraction operation was performed. The organic phase was dried over anhydrous magnesium sulfate and was then concentrated under reduced pressure. The residue was subjected to silica gel column chromatography, to obtain 87.2 g of the compound (T-3) as a colorless oily substance from an outflow of ethyl acetate and n-hexane (1/1).

Synthesis of a Compound (T-5)

Into 1000 ml of ethanol was dissolved 196.2 g of a compound (T-4), and then 83.4 g of powder of hydroxylamine hydrochloride was added thereto at room temperature. Next, the temperature of the reaction system was raised. While the reaction system was heated under reflux, 246 ml of sodium methoxide (28% methanol solution) was dropwise added thereto over 30 minutes. Thereafter, the reaction system was heated under reflux for 3 hours. After the reaction, the reaction solution was added to 2500 ml of ice water. Precipitated crystal was collected by filtration, and was then washed with 300 ml of water. The collected crystal was washed with 400 ml of cool isopropyl alcohol, to obtain 173.5 g of the compound (T-5) as yellow powder.

Synthesis of a Compound (T-6)

Into 60 ml of N,N-dimethylacetoamide and 8.6 ml of pyridine was dissolved 22.9 g of the compound (T-5), and then 16.5 g of phenyl chloroformate was dropwise added thereto at room temperature over 20 minutes. During the dropwise addition, the reaction temperature rose from 24° C. to 32° C. After the dropwise addition, the temperature was raised to 60° C. and the solution was subjected to reaction for 5 hours at 60° C. After the reaction, the solution was added to a mixed solution of 500 ml of water and 20 ml of conc. hydrochloric acid. Precipitated crystal was collected by filtration, and was then washed with 300 ml of water, to obtain 14.7 g of the compound (T-6) as pale yellow crystal.

The resultant crystal was crystal containing one molecule of N,N-dimethylacetoamide.

Synthesis of a Compound (T-7)

7.7 g of the compound (T-6) was mixed with 45.0 g of phosphorus oxychloride, and the mixture was heated. The compound (T-6) was completely dissolved at about 80° C. When the solution was heated to 100° C., 2.4 ml of pyridine was dropwise added thereto with sufficient attention. One hour was necessary for the dropwise addition. After the dropwise addition, the solution was subjected to reaction at 110° C. for 20 hours. After the reaction, the reaction system was cooled to room temperature, and was poured into 300 ml of ice water. Precipitated crystal was collected by filtration, and was then washed with 50 ml of water. The resultant crystal was suspended into a mixed solution of 50 ml of water and 50 ml of acetonitrile, and the suspension was stirred for 20 minutes. After the stirring, the crystal was collected by filtration, and was then washed with 20 ml of cool acetonitrile, to obtain 4.7 g of the compound (T-7) as pale red crystal.

Synthesis of an Exemplified Compound (R-22)

Into 50 ml of N,N-dimethylacetoamide was dissolved 4.1 g of the compound (T-3), and then 6.4 g of the compound (T-7) was added thereto in eight separate operations at room temperature. During the addition, the reaction temperature rose from 24° C. to 28° C. After the addition, the reaction temperature was raised and then the solution was subjected to further reaction at 60° C. for 6 hours. After the reaction, 300 ml of ethyl acetate and 350 ml of water were poured thereto to perform an extraction operation. The organic phase was dried over anhydrous magnesium sulfate, and was then concentrated under reduced pressure. The residue was subjected to silica gel column chromatography, to obtain 5.2 g of the exemplified compound (R-22) as colorless amorphous powder from an outflow of ethyl acetate and n-hexane (2/3).

The following will describe the formula (2-1) in detail.

The preferable examples of $R^1$ include halogen atoms, alkyl (including cycloalkyl and bicycloalkyl), alkenyl (including cycloalkenyl and bicycloalkenyl), alkynyl, aryl, heterocyclic, cyano, hydroxyl, nitro, carboxyl, alkoxy, aryloxy, silyloxy, heterocylic oxy, acyloxy, carbamoyloxy, alkoxycarbonyloxy, aryloxycarbonyloxy, amino (including anilino), acylamino, aminocarbonylamino, alkoxycarbonylamino, aryloxycarbonylamino, sulfamonylamino, alkyl- and aryl-sulfonylamino, mercapto, alkylthio, arylthio, heterocyclic thio, sulfamoyl, sulfo, alky- and aryl-sulfinyl, alkyl- and aryl-sulfonyl, acyl, aryloxycarbonyl, alkoxycarbonyl, carbamoyl, arylazo, heterocyclic azo, imido, phosphino, phosphinyl, phosphinyloxy, phosphinylamino, and silyl groups.

More specifically, examples of the substituent represented by $R^1$ include halogen atoms (such as fluorine, chlorine, bromine and iodine atoms), alkyl (straight-chain, branched or cyclic, and substituted or unsubstituted alkyl, preferably alkyl having 1–10 carbon atoms, such as methyl, ethyl, n-propyl, isopropyl, t-butyl, n-octyl, 2-chloroethyl, 2-cyanoethyl, and 2-ethylhexyl), and cycloalklyl groups (preferably, substituent or nonsubstituent cycloalkyl having 3–12 carbon atoms, such as cyclohexyl, cyclopentyl, and 4-n-dodecylcyclohexyl). An alkyl group in a substituent that will be described below (for example, alkyl in alkylthio) represents the alkyl group within a scope of such a concept.

Examples of the substituent represented by $R^1$ further include an alkenyl (preferably, substituted or unsubstituted alkenyl having 2–10 carbon atoms, such as vinyl, and allyl), cycloalkenyl (preferably, substituted or unsubstituted cycloalkenyl having 3–12 carbon atoms, that is, monovalent groups obtained by removing one hydrogen atom from cycloalkene having 3–12 carbon atoms, such as 2-cyclopentene-1-yl, and 2-cyclohexene-1-yl), alkynyl (preferably, substituted or unsubstituted alkynyl having 2–10 carbon atoms, such as ethynyl, propargyl, and trimethylsilylethynyl), aryl (preferably, substituted or unsubstituted aryl having 6–18 carbon atoms, such as phenyl, p-tolyl, naphthyl, m-chlorophenyl, and o-propanoylaminophenyl), heterocyclic (preferably, monovalent groups obtained by removing one hydrogen from 5- or 6-membered, substituted or unsubstituted and aromatic or non-aromatic heterocyclic compounds, and more preferably 5- or 6-membered and aromatic heterocyclic groups having 3–18 carbon atoms, such as 2-furyl, 2-thienyl, 2-pyrimidinyl, 2-benzothiazolyl), cyano, hydroxyl, nitro, carboxyl, alkoxy (preferably, substituted or unsubstituted alkoxy having 1–10 carbon atoms, such as methoxy, ethoxy, isopropoxy, t-butoxy, n-octyloxy, 2-methoxyethoxy), aryloxy (preferably, substituted or unsubstituted aryloxy having 6–18 carbon atoms, such as phenoxy, 2-methylphenoxy, 4-t-butylphenoxy, and 3-nitrophenoxy, 2-butanoylaminophenoxy), silyloxy (preferably, silyloxy having 3–10 carbon atoms, such as trimethylsilyloxy, and t-butyldimethylsilyloxy), heterocyclic oxy (preferably, substituted or unsubstituted heterocyclic oxy having 2–18 carbon atoms, such as 1-phenyltetrazole-5-oxy, and 2-tetrahydropyranyloxy), acyloxy (preferably, formyloxy, substituted or unsubstituted alkylcarbonyloxy having 2–10 carbon atoms, and substituted or unsubstituted arylcarbonyloxy having 6–18 carbon atoms, such as formyloxy, acetyloxy, pivaloyloxy, benzoyloxy, and p-methoxyphenylcarbonyloxy), carbamoyloxy (preferably, substituted or unsubstituted carbamoyloxy having 1–12 carbon atoms, such as N,N-dimethylcarbamoyloxy, N,N-diethylcarbamoyloxy, morpholinocarbonyloxy, N-n-octylcarbamoyloxy), alkoxycarbonyloxy (preferably, substituted or unsubstituted alkoxycarbonyloxy having 2–12 carbon atoms, such as methoxycarbonyloxy, ethoxycarbonyloxy, t-butoxycarbonyloxy, and n-octylcarbonyloxy), aryloxycarbonyloxy (preferably, substituted or unsubstituted aryloxycarbonyloxy having 7–18 carbon atoms, such as phenoxycarbonyloxy, p-methoxyphenoxycarbonyloxy, and p-n-propyloxyphenoxycarbonyloxy), amino (preferably, amino, substituted or unsubstituted alkylamino having 1–10 carbon atoms, and substituted or unsubstituted anilino having 6–18 carbon atoms, such as amino, methylamino, dimethylamino, anilino, N-methyl-anilino, and diphenylamino), acylamino (preferably, formylamino, substituted or unsubstituted alkylcarbonylamino having 1–10 carbon atoms, and substituted or unsubstituted arylcarbonylamino having 6–18 carbon atoms, such as formylamino, acetylamino, pyvaroylamino, benzoylamino), aminocarbonylamino (preferably, substituted or unsubstituted aminocarbonylamino having 1–12 carbon atoms, such as carbamoylamino, N,N-dimethylaminocarbonylamino, N,N-diethylaminocarbonylamino, and morpholinocarbonylamino), alkoxycarbonylamino (preferably, substituted or unsubstituted alkoxycarbonylamino having 2–12 carbon atoms, such as methoxycarbonylamino, ethoxycarbonylamino, t-butoxycarbonylamino, n-octyloxycarbonylamino, N-methyl-methoxycarbonylamino), aryloxycarbonylamino (preferably, substituted or unsubstituted aryloxycarbonylamino having 7–18 carbon atoms, such as phenoxycarbonylamino, p-chlorophenoxycarbonylamino, m-n-octyloxyphenoxycarbonylamino), sulfamoylamino (preferably, substituted or unsubstituted sulfamoylamino having 0–10 carbon atoms, such as sulfamoylamino, N,N-dimethylaminosulfonylamino, and N-n-octylaminosulfonylamino), alkyl- and aryl-sulfonylamino (preferably, substituted or unsubstituted alkylsulfonylamino having 1–10 carbon atoms, and substituted or unsubstituted arylsulfonylamino having 6–18 carbon atoms, such as methylsulfonylamino, butylsulfonylamino, phenylsulfonylamino, 2,3,5-trichlorophenylsulfonylamino, and p-methylphenylsulfonylamino), mercapto, alkylthio (preferably, substituted or unsubstituted alkylthio having 1–10 carbon atoms, such as methylthio, ethylthio, n-hexadecylthio), arylthio (preferably, substituted or unsubstituted arylthio having 6–18 carbon atoms, such as phenylthio, and p-chlorophenylthio, m-methoxyphenylthio), heterocyclic thio (preferably, substituted or unsubstituted heterocyclic thio having 2–18 carbon atoms, such as 2-benzothiazolylthio, and 1-phenyltetrazole-5-ylthio), sulfamonyl (preferably, substituted or unsubstituted sulfamoyl having 0–10 carbon atoms, such as N-ethylsulfamoyl, N-(3-hydroxypropyl)sulfamoyl, N,N-dimethylsulfamoyl, N-acetylsulfamoyl, N-benzoylsulfamoyl, and N-(N'-phenylcarbamoyl)sulfamoyl), sulfo, alkyl- and aryl-sulfinyl (preferably, substituted or unsubstituted alkylsulfinyl having 1–10 carbon atoms, and substituted or unsubstituted arylsulfinyl having 6–18 carbon atoms, such as methylsulfinyl, ethylsulfinyl, phenylsulfinyl, and p-methylphenylsulfinyl), alkyl- and aryl-sulfonyl (preferably, substituted or unsubstituted alkylsulfonyl having 1–10 carbon atoms, and substituted or unsubstituted arylsulfonyl having 6–18 carbon atoms, such as methylsulfonyl, ethylsulfonyl, phenylsulfonyl, and p-methylphenylsulfonyl), acyl (preferably, formyl, substituted or unsubstituted alkylcarbonyl having 2–12 carbon atoms, and substituted or unsubstituted arylcarbonyl having 7–20 carbon atoms, such as acetyl, pivaloyl, 2-chloroacetyl, benzoyl, p-n-propyloxyphenylcarbonyl), aryloxycarbonyl (preferably, substituted or unsubstituted aryloxycarbonyl having 7–20 carbon atoms, such as phenoxycarbonyl, o-chlorophenoxycarbonyl, m-nitrophenoxycarbonyl, and p-t-butylphenoxycarbonyl), alkoxycarbonyl (preferably, substituted or unsubstituted alkoxycarbonyl having 2–10 carbon atoms, such as methoxycarbonyl, ethoxycarbonyl, and t-butoxycarbonyl), carbamoyl (preferably, substituted or unsubstituted carbamoyl having 1–20 carbon atoms, such as carbamoyl, N-methylcarbamoyl, N,N-dimethylcarbamoyl, N,N-di-n-octylcarbamoyl, and N-(methylsulfonyl) carbamoyl), arylazo and heterocyclic azo (preferably, substituted or unsubstituted arylazo having 6–20 carbon atoms, and substituted or unsubstituted heterocyclic azo having 3–20 carbon atoms, such as phenylazo, p-chlorophenylazo, 5-ethylthio-1,3,4-thiadiazole-2-ylazo), imido (preferably, N-succimido, and N-phthalimido), phosphino (preferably, substituted or unsubstituted phosphino having 2–18 carbon atoms, such as dimethylphosphino, diphenylphosphino, and methylphenoxyphosphino), phosphinyl (preferably, substituted or unsubstituted phosphinyl having 2–18 carbon atoms, such as phosphinyl, dioctyloxyphosphinyl, and diethoxyphosphinyl), phosphinyloxy (preferably, substituted or unsubstituted phosphinyloxy having 2–18 carbon atoms, such as diphenoxyphospinyloxy, dioctyloxyphosphinyloxy), phosphinylamino (preferably, substituted or unsubstituted phosphinylamino having 2–18 carbon atoms, such as dimethoxyphosphyinylamino, and dimethylaminophosphinylamino), silyl groups(preferably, substituted or unsubstituted silyl having 3–12 carbon atoms, such as trimethylsilyl, t-butyldimethylsilyl, and phenyldimethylsilyl).

Groups having one or more hydrogen atoms, among the above-mentioned functional groups, may be removed the hydrogen atom(s) and further substituted with the above-mentioned group(s). Examples of such a functional group include alkylcarbonylaminosulfonyl, arylcarbonylaminosulfonyl, alkylsulfonylaminocarbonyl, and arylsulfonylaminocarbonyl groups. Specific examples thereof include methylsulfonylaminocarbonyl, p-methylphenylsulfonylaminocarbonyl, acetylaminosulfonyl, and benzoylaminosulfonyl.

Among the above-mentioned $R^1$, halogen atoms, alkyl, aryl and heterocyclic groups are preferred. Aryl and heterocyclic groups are more preferred. Examples of the substituent thereon are the same as described above.

A represents a group of atoms necessary for formation of the azo dye by the compound of the formula (2–1), and A is preferably a group to give a coupler which has been used in a silver halide photographic light-sensitive material. The bonding of the coupler to the azo moiety is the same position where the coupler is coupling-reacted with a p-phenylenediamine-series developing agent in a silver halide photographic light-sensitive material.

The following describe specific examples of the coupler in detail: on pages 291–343 and pages 354–361 in "The Theory of the Photographic Process" (4th edition, edited by T. H. James, Macmillian, 1977), JP-A-58-12353, JP-A-58-149046, JP-A-58-149047, JP-A-59-11114, JP-A-59-124399, JP-A-59-174835, JP-A-59-231539, JP-A-59-231540, JP-A-60-2951, JP-A-60-14242, JP-A-60-23474, JP-A-60-66249, on pages 80–83 in Research Disclosure No. 37038 (February, 1995), and on pages 614–617 in Research Disclosure No. 40145 (September, 1997).

A is particularly preferably a group represented by the following formula (2-2).

formula (2-2)

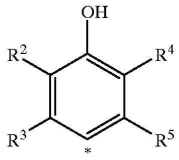

In the formula (2-2), $R^2$, $R^3$, $R^4$ and $R^5$ each represent a hydrogen atom or a substituent. Examples of the substituent are the same as described about $R^1$. Preferred examples of the substituent include halogen atoms, alkyl, cyano, alkoxy, acylamino, aminocarbonylamino, alkoxycarbonylamino, alkyl- and aryl-sulfonylamino, sulfamoyl, sulfo, alkyl- and aryl-sulfinyl, alkyl- and aryl-sulfonyl, acyl, alkoxycarbonyl, and carbamoyl groups. $R^2$ and $R^3$ and/or $R^4$ and $R^5$ may bond together to form a ring. The number of the atoms in the ring is preferably 5 to 7. * represents a position which is bonded to the azo moiety in the formula (2-1).

A is preferably a group represented by the following formula (2-3):

formula (2-3)

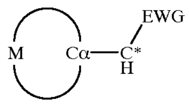

In the formula (2-3), Cα represents a carbon atom, EWG represents a cyano, carbamoyl or alkoxycarbonyl group, and most preferably a cyano group. M represents a group of atoms necessary to form together with the Cα a 5- or 6-memebered aromatic heteroring. Examples of the aromatic heteroring include pyrrole, imidazole, pyrazole, 1,2,3-triazole, 1,2,4-triazole, tetrazole, 1,3,4-thiadiazole, 1,2,4-thiadiazole, 1,3,4-oxadiazole, 1,2,4-oxadiazole, thiazole, oxazole, isothiazole, isooxazole, thiophene, benzoxazole, benzimidazole, benzothiazole, benzoisothiazole, pyrazine, pyrimidine, pyridazine, 1,2,4-triazine, 1,3,5-triazine, quinazoline, quinazolone, quinoxaline, synoline, pteridine, and thiazinone rings. To these rings, an aromatic ring such as a benzene ring or a naphthalene ring, and an aromatic heteroring as mentioned above may be condensed.

Among the exemplified aromatic heterorings, 1,3,4-thiadiazole, 1,2,4-thiadiazole, thiazole, benzothiazole, benzoisothiazole and pyrimidine rings are more preferred.

* represents a position which is bonded to the azo moiety in the formula (2-1).

A is preferably a group represented by the following formula (2-4):

formula (2-4)

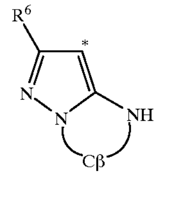

wherein $R^6$ represents a hydrogen atom or a substituent, and examples of the substituent are the same as described about $R^1$. Preferred examples of the substituent include alkyl, alkoxy, phenoxy, acylamino, alkoxycarbonyl and carbamoyl groups. Cβ represents a group of atoms necessary to form together with the N—C—NH a 5- or 6-memebered aromatic heteroring. Preferred examples of the aromatic heteroring include imidazole, triazole, and benzimidazole rings. * represents a position which is bonded to the azo moiety in the formula (2-1).

In the case that the dye of the present invention is used in a diffusion transfer image forming method, the dye is used as the following image-forming compound (also referred to as dye-providing compound).

formula (2-5)

$(Dye)_q$-$X^1$—Y

In the formula (2-5), Dye represents a dye represented by the formula (2-1) (e.g. yellow azo dye) or a dye precursor (e.g. yellow azo dye precursor), $X^1$ represents a single bond or a connecting group which is cleaved in correspondence to or in inverse correspondence to development, Y represents a group which has a nature of generating a difference in diffusibility of the dye component in correspondence to or in inverse correspondence to reaction of a light-sensitive silver salt having a latent image imagewise, Dye is bonded to $X^1$ at a position or positions of at least one of $R^1$ and A in the above-mentioned formula (2-1), q is 1 or 2, and when q is 2, Dye's may be the same or different.

The following will describe the compound of the formula (2-5) in detail.

q is 1 or 2, and when q is 2, Dye's may be the same or different. Preferably, q is 1. Dye and $X^1$ are bonded to each other at a position or positions of at least one of $R^1$ and A in the above-mentioned formula (2-1).

Typical examples of the connecting group represented by $X^1$ include groups represented by —$N(R^7)$— (in which $R^7$ is a hydrogen atom or an alkyl or substituted alkyl group), —$SO_2$—, —CO—, alkylene, substituted alkylene, phenylene, substituted phenylene, naphthylene, substituted naphthylene, —O—, —SO—, and groups obtianed by combining two or more of these divalent groups. Preferred are groups represented by —$NR^7SO_2$—, —$NR^7$—CO—, and —$R^8$—$(L)_k$—$(R^9)_j$—. $R^8$ and $R^9$ each represent an alkylene, substituted alkylene, phenylene, substituted phenylene, naphthylene, or substituted naphthylene group. L represents —O—, —CO—, —SO—, —$SO_2$—, —$SO_2NH$—, —$NHSO_2$—, —CONH—, or —NHCO—. k is 0 or 1, and j is 1 or 0.

Any combination of elements selected from —$NR^7$—$SO_2$—, —$NR^7$—CO—, and —$R^8$—$(L)_k$—$(R^9)_j$— is also preferred.

The following will describe Y. Y represents a group which has a nature that the Y-$X^1$ bond is cleaved in correspondence to or in inverse correspondence to a light-sensitive silver halide having a latent image. Such a group is known in the field of photographic chemistry using diffusion transfer of a dye, and is described in, for example, U.S. Pat. No. 5,021,334 (corresponding to JP-A-2-184852).

The following will describe Y in detail. (Respective formulae which will be shown below are described in the state that $X^1$ is included.)

The bonding form of the Dye moiety and the Y moiety is particularly preferably a Dye-$SO_2NH$—Y form.

(1) First, Y may be a negative-acting releaser which releases a photographically useful group in correspondence to development.

As Y classified into the negative-acting releaser, a group of releasers which release a photographically useful group from an oxidized product is known. A preferred example of Y of this type is represented by the following formula (Y-1):

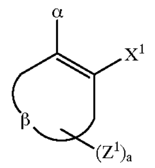

In the above-mentioned formula, β represents a group of non-metal atoms necessary for forming a benzene ring, and a saturated or unsaturated carbon ring or heteroring may be condensed to this benzene ring. α represents —$OZ^2$ or —$NHZ^3$ wherein $Z^2$ represents a hydrogen atom or a group which can generate a hydroxyl group by hydrolysis, and $Z^3$ represents a hydrogen atom, an alkyl or aryl group, or a group which can generate an amino group by hydrolysis. $Z^1$ represents an alkyl, aryl, aralkyl, alkoxy, alkylthio, aryloxy, arylthio, acyl, sulfonyl, acylamino, sulfonylamino, carbamoyl, sulfamoyl, ureido, urethane, heterocyclic or cyano group, each of which may have a substituent if possible, or a halogen atom, and a is a positive integer. When the number of $Z^1$s is two or more, all of $Z^1$s may be the same or different. In the formula (Y-1), —$X^1$ is a group represented by —$NHSO_2Z^4$ wherein $Z^4$ is a divalent group.

A more preferred group of the formula (Y-1) is the following formula (Y-2) or (Y-3).

formula (Y-2)

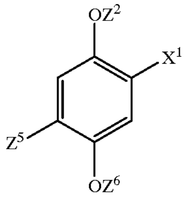

formula (Y-3)

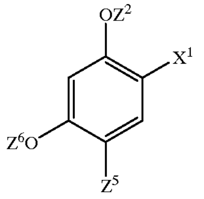

In the above-mentioned formulae, $Z^2$ and $X^1$ have the same meanings as described about the formula (Y-1), and $Z^5$ and $Z^6$ each represent an alkyl, aryl or aralkyl group. These may have a substituent. $Z^5$ is more preferably a secondary or tertiary alkyl group. The total number of carbon atoms in $Z^5$ and $Z^6$ is preferably from 20–50.

Specific examples thereof are described in U.S. Pat. No. 4,055,428 and No. 4,336,322, JP-A-51-113624, JP-A-56-16131, JP-A-56-71061, JP-A-56-71060, JP-A-56-71072, JP-A-56-73057, JP-A-57-650, JP-A-57-4043, JP-A-59-60439, JP-B-56-17656 and JP-B-60-25780.

Another example of Y is represented by the following formula (Y-4):

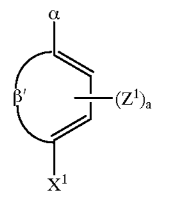

wherein α, $X^1$, $Z^1$ and a have the same meanings as described about for the formula (Y-1), β' represents a group of non-metal atoms necessary for forming a benzene ring, and a saturated or unsaturated carbon ring or heteroring may be condensed to this benzene ring.

Among the groups represented by the formula (Y-4), a group wherein α is —$OZ^2$ and β' forms into a naphthalene skeleton is preferred. Specific examples thereof are described in U.S. Pat. No. 3,928,312 and No. 4,135,929.

Examples of the releaser which releases a photographically useful group by a reaction similar to the formula (Y-1) or (Y-4) include groups described in JP-A-51-104343, JP-A-53-46730, JP-A-54-130122, JP-A-57-85055, JP-A-53-3819, JP-A-54-48534, JP-A-49-64436, JP-A-57-20735, JP-B-48-32129, JP-B-48-39165, and U.S. Pat. No. 3,443,934.

Examples of a compound which releases a photographically useful group from an oxidized product in accordance with another reaction mechanism include hydroquinone derivatives represented by the following formula (Y-5) or (Y-6):

formula (Y-5)

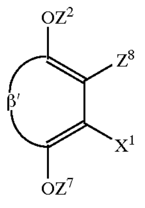

-continued formula (Y-6)

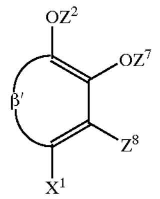

wherein β' and $Z^2$ have the same meanings as described about for the formula (Y-4) and the formula (Y-1), respectively, $Z^7$ has the same meaning as $Z^2$, and $Z^8$ represents the same substituent as described about for $Z^1$ or a hydrogen atom. $Z^2$ and $Z^7$ may be the same or different. Specific examples of this type releaser are described in U.S. Pat. No. 3,725,062.

A releaser having a nucleophilic group in its molecule of the above-mentioned type of hydroquinone derivative releaser may also be used. Specific examples thereof are described in JP-A-4-97347.

Examples of another Y include p-hydroxydiphenylamine derivatives described in U.S. Pat. No. 3,443,939, and hydrazine derivatives described in U.S. Pat. No. 3,844,785 and No. 4,684,604, and on page 22 of R. D. Vol. 128.

The negative-acting releaser may be represented by the following formula (Y-7):

Coup-$X^1$ wherein Coup is a group which is coupled with an oxidized product of any one of p-phenylenediamines or p-aminophenols, that is, a group to give a compound which is known as a photographic coupler. Specific examples thereof are described in G.B. Patent No. 1,330,524.

(2) Secondly, Y may be a positive-acting releaser which releases a photographically useful group in reverse correspondence to development.

The positive-acting releaser may be a releaser which exhibits a function when the releaser is reduced at the time of development processing. Preferred examples of Y of this type releaser include those represented by the following formula (Y-8):

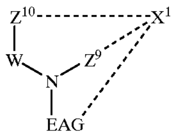

wherein EAG represents a group which accepts an electron from a reducing substance, N represents a nitrogen atom, and W represents an oxygen atom, a sulfur atom or —$NZ^{11}$—. After EAG receives an electron, the N—W bond is cleaved. $Z^{11}$ represents an alkyl or aryl group, and $Z^9$ and $Z^{10}$ each represent a single bonding hand, or a substituent other than a hydrogen atom. Solid lines each represent a bond, and at least one of dot lines is a bond.

Among the groups represented by the formula (Y-8), preferred is a group represented by the following formula (Y-9):

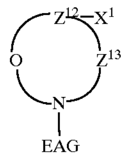

wherein O represents an oxygen atom (that is, W in the formula (Y-8) is an oxygen atom), and $Z^{12}$ represents a group of atoms having a nature of forming a heteroring containing a N—O bond and causing cleavage of the $Z^{12}$—$X^1$ bond after the cleavage of the N—O bond. $Z^{12}$ may have a substituent, and a saturated or unsaturated ring may be condensed to $Z^{12}$. $Z^{13}$ represents —CO— or —$SO_2$—.

Among the groups represented by the formula (Y-9), more preferred is a group represented by the following formula (Y-10):

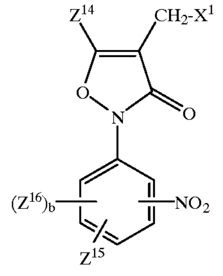

wherein $Z^{14}$ represents an alkyl, aryl or aralkyl group, $Z^{15}$ represents a carbamoyl or sulfamoyl group, $Z^{16}$ represents an alkyl, aryl, aralkyl, alkoxy, alkylthio, arylthio, arylthio, cyano or nitro group, or a halogen atom, b is an integer of 0 to 3, and the substituting position for the nitro group in the formula is ortho or para to the nitrogen atom. $Z^{15}$ is most preferably a carbamoyl or sulfamoyl group substituted with an alkyl group having 12–30 carbon atoms.

Specific examples of this type Y are described in JP-A-62-215270 and U.S. Pat. No. 4,783,396.

Different examples of the positive-acting releaser exhibiting a function by reduction include BEND compounds described in U.S. Pat. No. 4,139,379 and No. 4,139,389, Carquin compounds described in G.B. Patent No. 11,445, and releasers described in JP-A-54-126535 and JP-A-57-84453.

When such a releaser to be reduced, the typical example of which is represented by the formula (Y-8), is used, a reducing agent is used together with the releaser. LDA compounds which also have, in their molecule, a reducing group may be used. Examples thereof are described in U.S. Pat. No. 4,551,423.

As the positive-acting releaser, there is known a releaser which is incorporated, as a reductant, into a light-sensitive material and is inactivated by oxidization at the time of development processing. Examples of this type releaser include Fields compounds described in JP-A-51-63618 and U.S. Pat. No. 3,980,479, and Hinshaw compounds described in JP-A-49-111628, JP-A-52-4819, and U.S. Pat. No. 4,199,354.

Examples of this type Y may be represented by the following formula (Y-11):

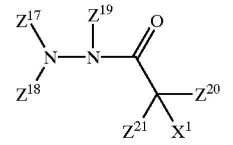

wherein $Z^{17}$ and $Z^{19}$ each represent a hydrogen atom or a substituted or unsubstituted acyl, alkoxycarbonyl, or aryloxycarbonyl group, $Z^{18}$ represents an alkyl, aryl, aralkyl, acyl, alkoxycarbonyl, aryloxycarbonyl, carbamoyl, sulfonyl, or sulfamoyl group, and $Z^{20}$ and $Z^{21}$ each represent a hydrogen atom, or a substituted or unsubstituted alkyl, aryl, or aralkyl group. Specific examples thereof are described in JP-A-62-245270 and JP-A-63-46450.

A positive-acting releaser having another mechanism is a thiazolizine type releaser. Specific examples thereof are described in U.S. Pat. No. 4,468,451 and JP-A-7-159962.

The following will show specific examples of the dye of the formula (2-1) used in the present invention, but the present invention is not limited to these examples.

First, specific examples of A in the formula (2-1) are shown.

(C-1)

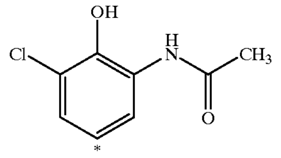

(C-2)

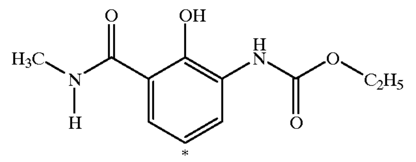

(C-3)

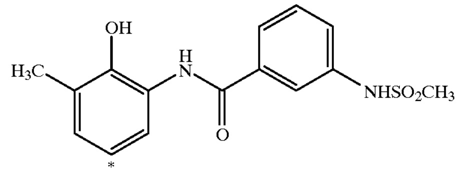

(C-4)

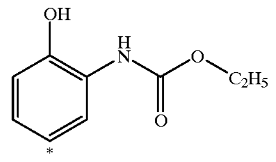

(C-5)

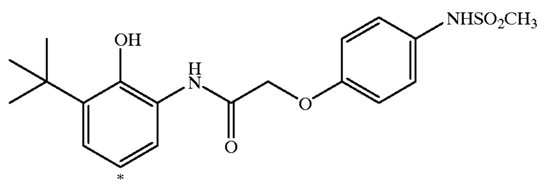

-continued
(C-6)
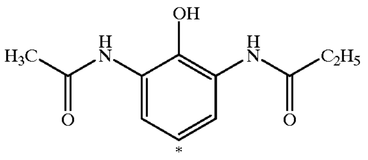
(C-7)
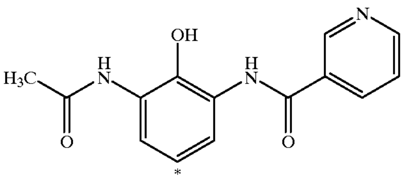
(C-8)
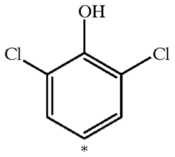
(C-9)
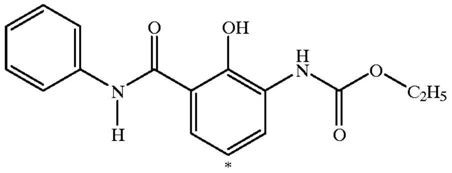
(C-10)
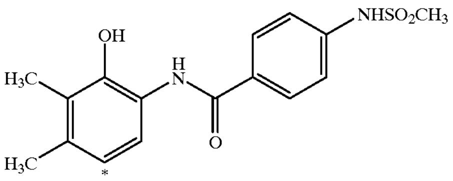
(C-11)
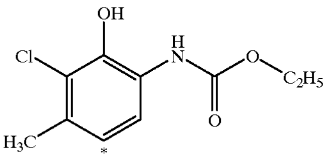
(C-12)
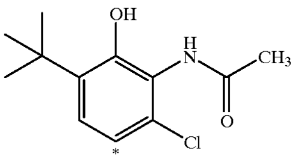
(C-13)
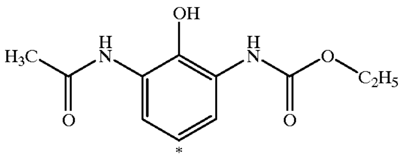
-continued
(C-14)
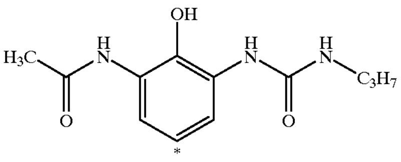
(C-15)
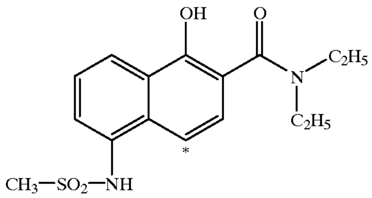
(C-16)
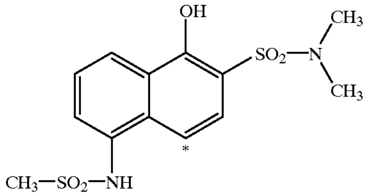
(C-17)
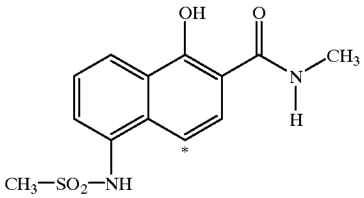
(C-18)
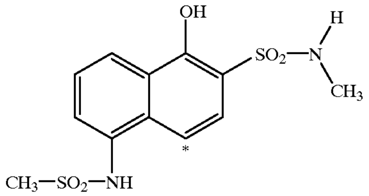
(C-19)
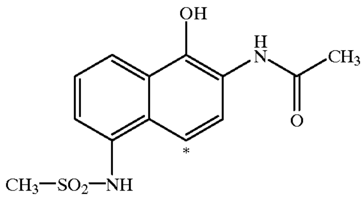
(C-20)
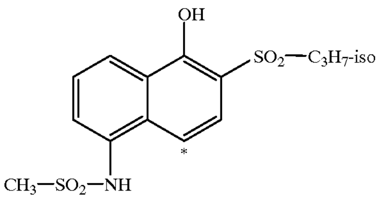

-continued
(C-21)
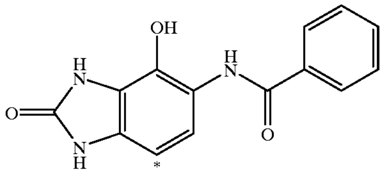
(C-22)
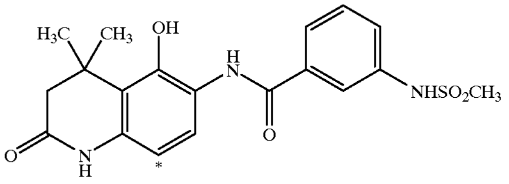
(C-23)
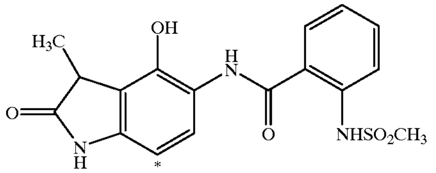
(C-24)
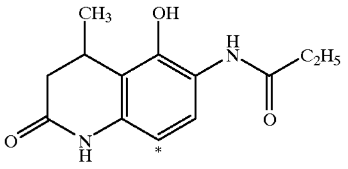
(C-25)
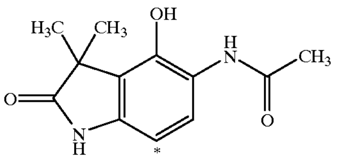
(C-26)
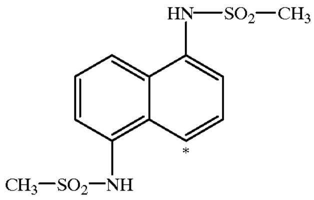
(C-27)
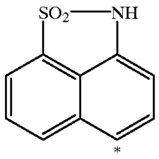
(C-28)
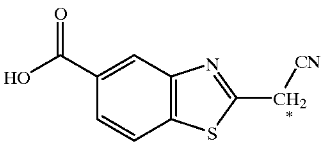
-continued
(C-29)
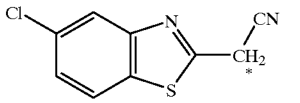
(C-30)
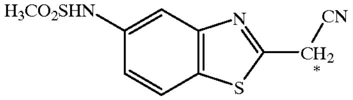
(C-31)
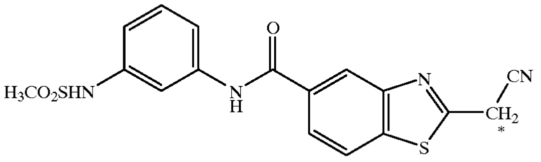
(C-32)
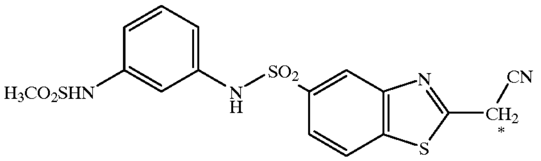
(C-33)
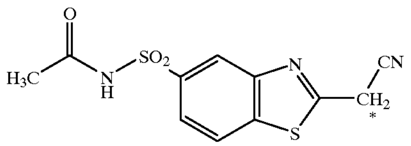
(C-34)
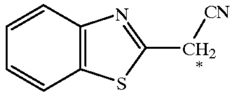
(C-35)
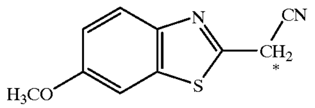
(C-36)
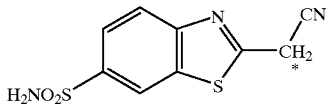
(C-37)
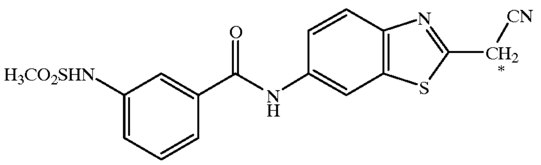

-continued
(C-38)
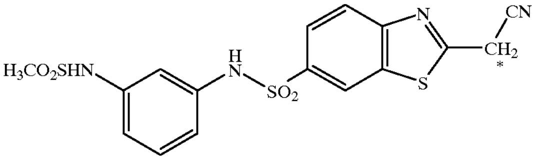
(C-39)
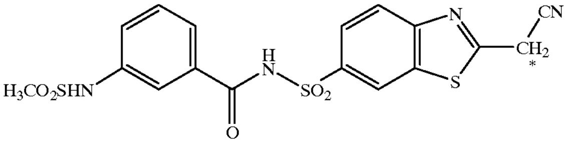
(C-40)
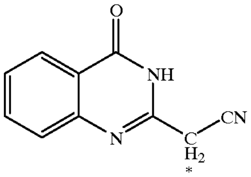
(C-41)
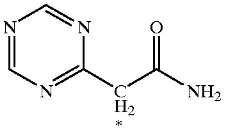
(C-42)
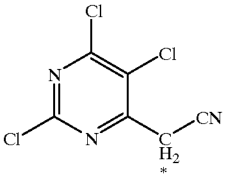
(C-43)
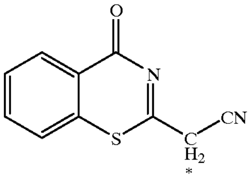
(C-44)
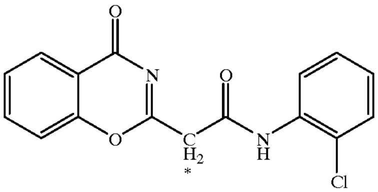
(C-45)
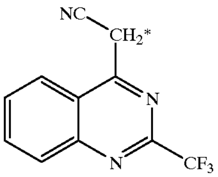
-continued
(C-46)
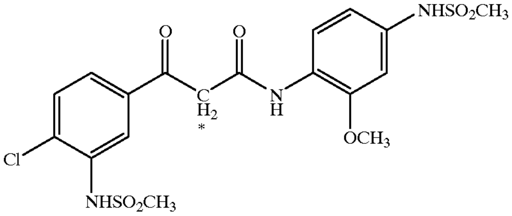
(C-47)
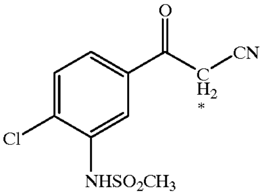
(C-48)
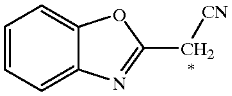
(C-49)
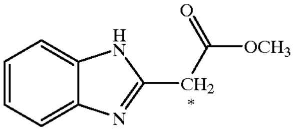
(C-50)
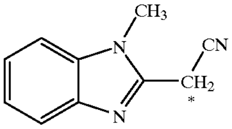
(C-51)
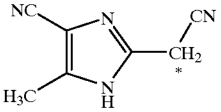
(C-52)
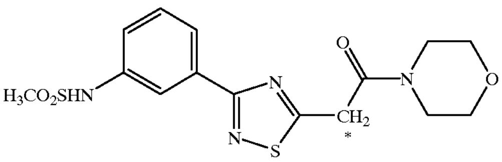
(C-53)
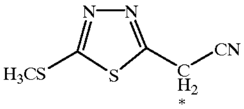
(C-54)
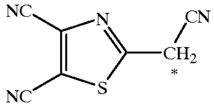

-continued
(C-55)
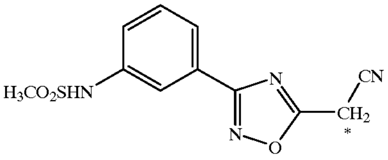
(C-56)
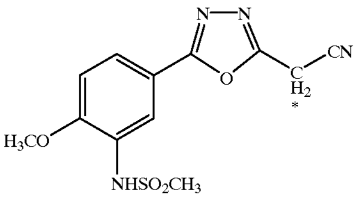
(C-57)
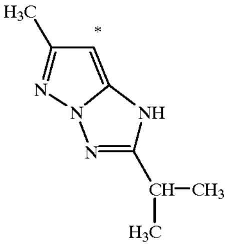
(C-58)
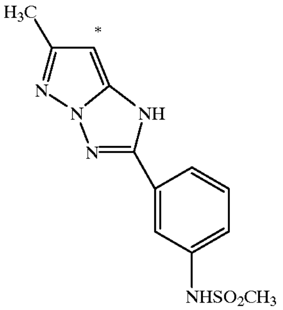
(C-59)
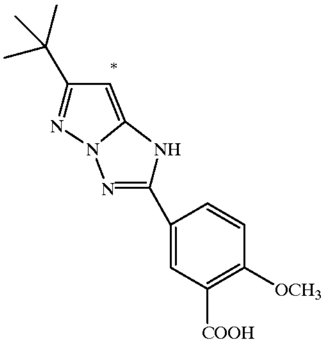
-continued
(C-60)
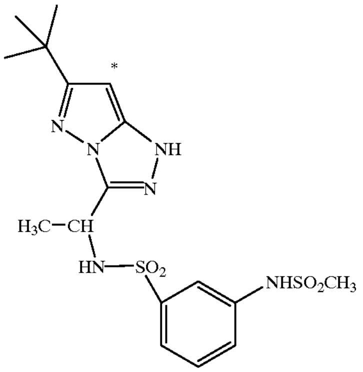
(C-61)
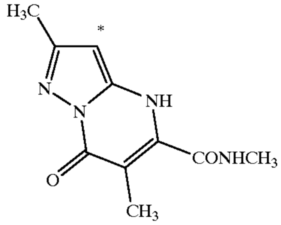
(C-62)
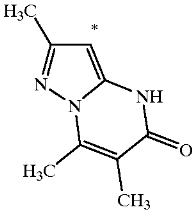
(C-63)
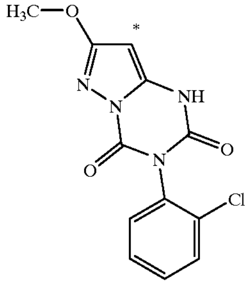
In the above formulas, * represents a position which is bonded to the nitrogen atom in the azo moiety. When a hydrogen atom is present at this position, the position is bonded to the nitrogen atom in the azo moiety after the hydrogen atom leaves off.
Next, specific examples of 1,2,4-oxadiazole azo moiety are shown.
(OXA-1)
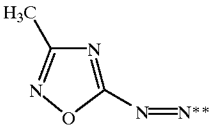

-continued
(OXA-2)
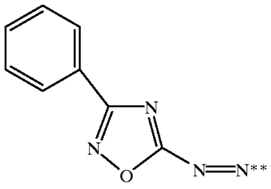
(OXA-3)
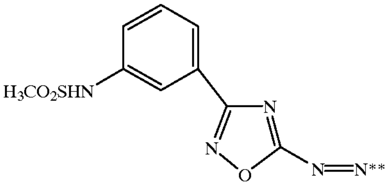
(OXA-4)
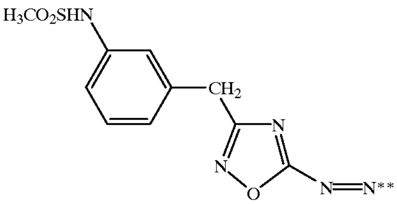
(OXA-5)
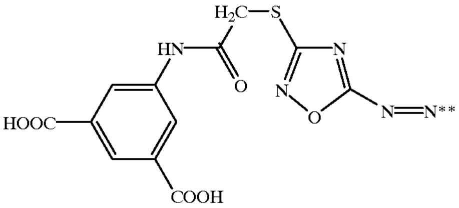
(OXA-6)
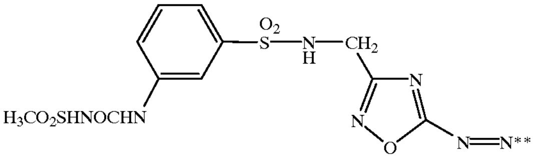
(OXA-7)
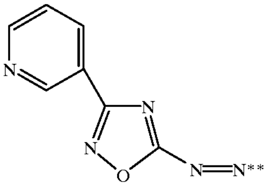
(OXA-8)
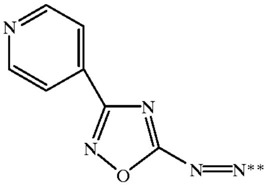
-continued
(OXA-9)
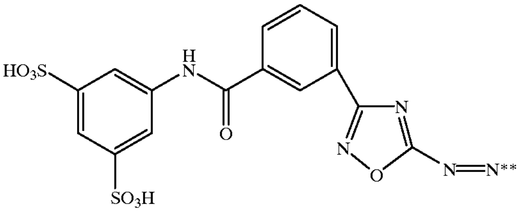
(OXA-10)
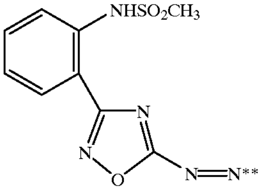
(OXA-11)
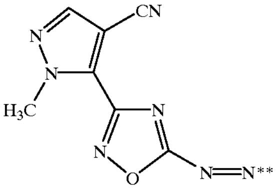
(OXA-12)
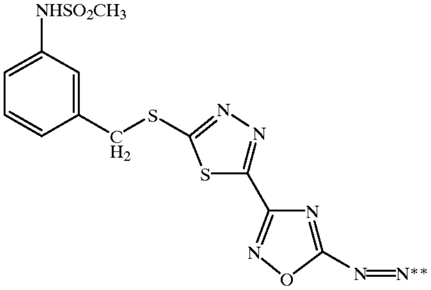
(OXA-13)
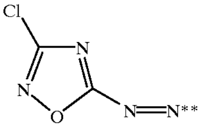
(OXA-14)
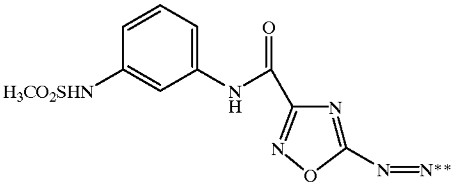
(OXA-15)
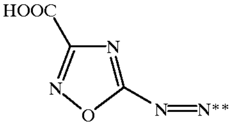
(OXA-16)
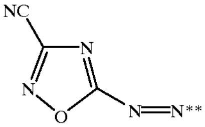

-continued (OXA-17)

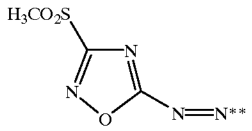

(OXA-18)

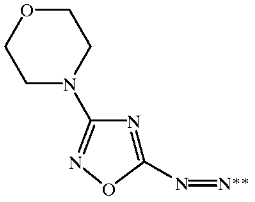

In the above formulas, ** represents a position which is bonded to A in the formula (2-1).

The groups shown above may be arbitrarily combined each other. The following will show preferred dye examples.

| Dye No. | C - No | P - No |
|---|---|---|
| DYE-1 | C-1 | OXA-14 |
| DYE-2 | C-2 | OXA-3 |
| DYE-3 | C-3 | OXA-13 |
| DYE-4 | C-4 | OXA-15 |
| DYE-5 | C-5 | OXA-2 |
| DYE-6 | C-6 | OXA-2 |
| DYE-7 | C-7 | OXA-3 |
| DYE-8 | C-8 | OXA-1 |
| DYE-9 | C-9 | OXA-4 |
| DYE-10 | C-10 | OXA-5 |
| DYE-11 | C-11 | OXA-6 |
| DYE-12 | C-12 | OXA-18 |
| DYE-13 | C-13 | OXA-7 |
| DYE-14 | C-14 | OXA-8 |
| DYE-15 | C-15 | OXA-4 |
| DYE-16 | C-16 | OXA-16 |
| DYE-17 | C-17 | OXA-13 |
| DYE-18 | C-18 | OXA-12 |
| DYE-19 | C-19 | OXA-9 |
| DYE-20 | C-20 | OXA-10 |
| DYE-21 | C-21 | OXA-11 |
| DYE-22 | C-22 | OXA-13 |
| DYE-23 | C-23 | OXA-14 |
| DYE-24 | C-24 | OXA-15 |
| DYE-25 | C-25 | OXA-4 |
| DYE-26 | C-26 | OXA-5 |
| DYE-27 | C-27 | OXA-6 |
| DYE-28 | C-28 | OXA-1 |
| DYE-29 | C-29 | OXA-1 |
| DYE-30 | C-30 | OXA-1 |
| DYE-31 | C-31 | OXA-2 |
| DYE-32 | C-32 | OXA-3 |
| DYE-33 | C-33 | OXA-3 |
| DYE-34 | C-34 | OXA-11 |
| DYE-35 | C-35 | OXA-13 |
| DYE-36 | C-36 | OXA-16 |
| DYE-37 | C-37 | OXA-18 |
| DYE-38 | C-38 | OXA-14 |
| DYE-39 | C-39 | OXA-1 |
| DYE-40 | C-40 | OXA-8 |
| DYE-41 | C-41 | OXA-5 |
| DYE-42 | C-42 | OXA-6 |
| DYE-43 | C-43 | OXA-1 |
| DYE-44 | C-44 | OXA-11 |
| DYE-45 | C-45 | OXA-12 |
| DYE-46 | C-46 | OXA-13 |
| DYE-47 | C-47 | OXA-14 |
| DYE-48 | C-48 | OXA-13 |
| DYE-49 | C-49 | OXA-14 |
| DYE-50 | C-50 | OXA-15 |

-continued

| Dye No. | C - No | P - No |
|---|---|---|
| DYE-51 | C-51 | OXA-16 |
| DYE-52 | C-52 | OXA-17 |
| DYE-53 | C-53 | OXA-18 |
| DYE-54 | C-54 | OXA-1 |
| DYE-55 | C-55 | OXA-9 |
| DYE-56 | C-56 | OXA-8 |
| DYE-57 | C-57 | OXA-2 |
| DYE-58 | C-58 | OXA-3 |
| DYE-59 | C-59 | OXA-14 |
| DYE-60 | C-60 | OXA-17 |
| DYE-61 | C-61 | OXA-7 |
| DYE-62 | C-62 | OXA-8 |
| DYE-63 | C-63 | OXA-11 |
| DYE-64 | C-1 | OXA-1 |
| DYE-65 | C-16 | OXA-1 |
| DYE-66 | C-6 | OXA-3 |
| DYE-67 | C-9 | OXA-3 |
| DYE-68 | C-30 | OXA-3 |
| DYE-69 | C-34 | OXA-3 |
| DYE-70 | C-14 | OXA-4 |
| DYE-71 | C-60 | OXA-4 |
| DYE-72 | C-58 | OXA-9 |
| DYE-73 | C-37 | OXA-10 |
| DYE-74 | C-59 | OXA-10 |
| DYE-75 | C-13 | OXA-14 |
| DYE-76 | C-39 | OXA-14 |
| DYE-77 | C-3 | OXA-17 |
| DYE-78 | C-37 | OXA-17 |
| DYE-79 | C-34 | OXA-3 |
| DYE-80 | C-37 | OXA-3 |

The following will show specific examples of the image-forming compound of the formula (2-5) used in the present invention, but the present invention is not limited to these examples.

| Compound No. | Y |
|---|---|
| 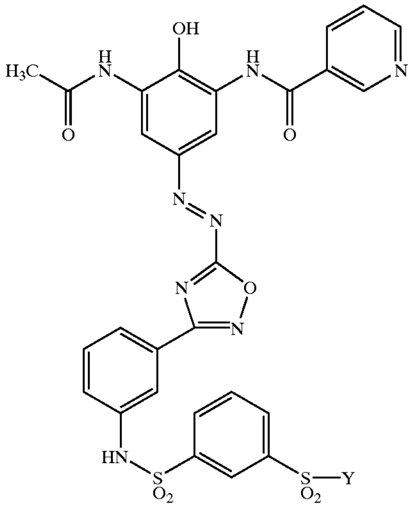 | |
| K-1 | Y-1 |
| K-2 | Y-2 |
| K-3 | Y-3 |

-continued

| Compound No. | Y |
|---|---|
| 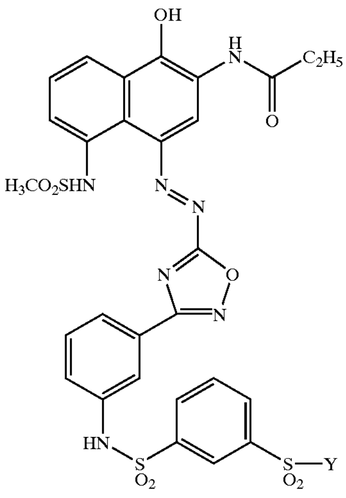 | |
| K-4 | Y-1 |
| K-5 | Y-2 |
| K-6 | Y-3 |
| 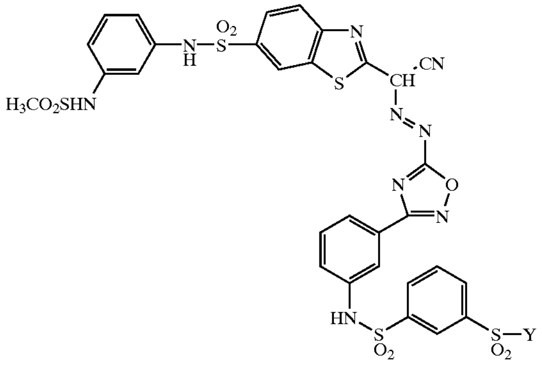 | |
| K-7 | Y-1 |
| K-8 | Y-2 |
| K-9 | Y-3 |
| 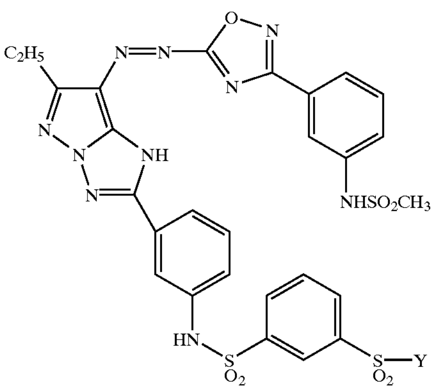 | |
| K-10 | Y-1 |

-continued

| Compound No. | Y |
|---|---|
| K-11 | Y-2 |
| K-12 | Y-3 |

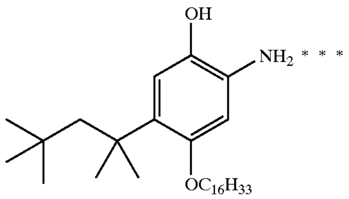

Y-1

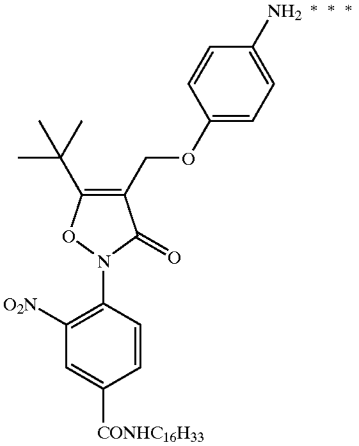

Y-2

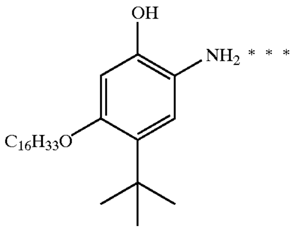

Y-3

In the above formulas, the group —Y represents a group of the above Y-1, Y-2 or Y-3 bonding at any position after the hydrogen atom on the position leaves off. Preferably, it is a group of the above Y-1, Y-2 or Y-3 bonding at the position shown with *** after the hydrogen atom thereon leaves off.

The dye of the present invention can be synthesized by diazo-coupling reaction of a coupler component with a diazo component.

The following will describe specific synthesis examples of the present invention, but the present invention is not limited to these examples.

The exemplified dye (DYE-7) was synthesized in accordance with the following route.

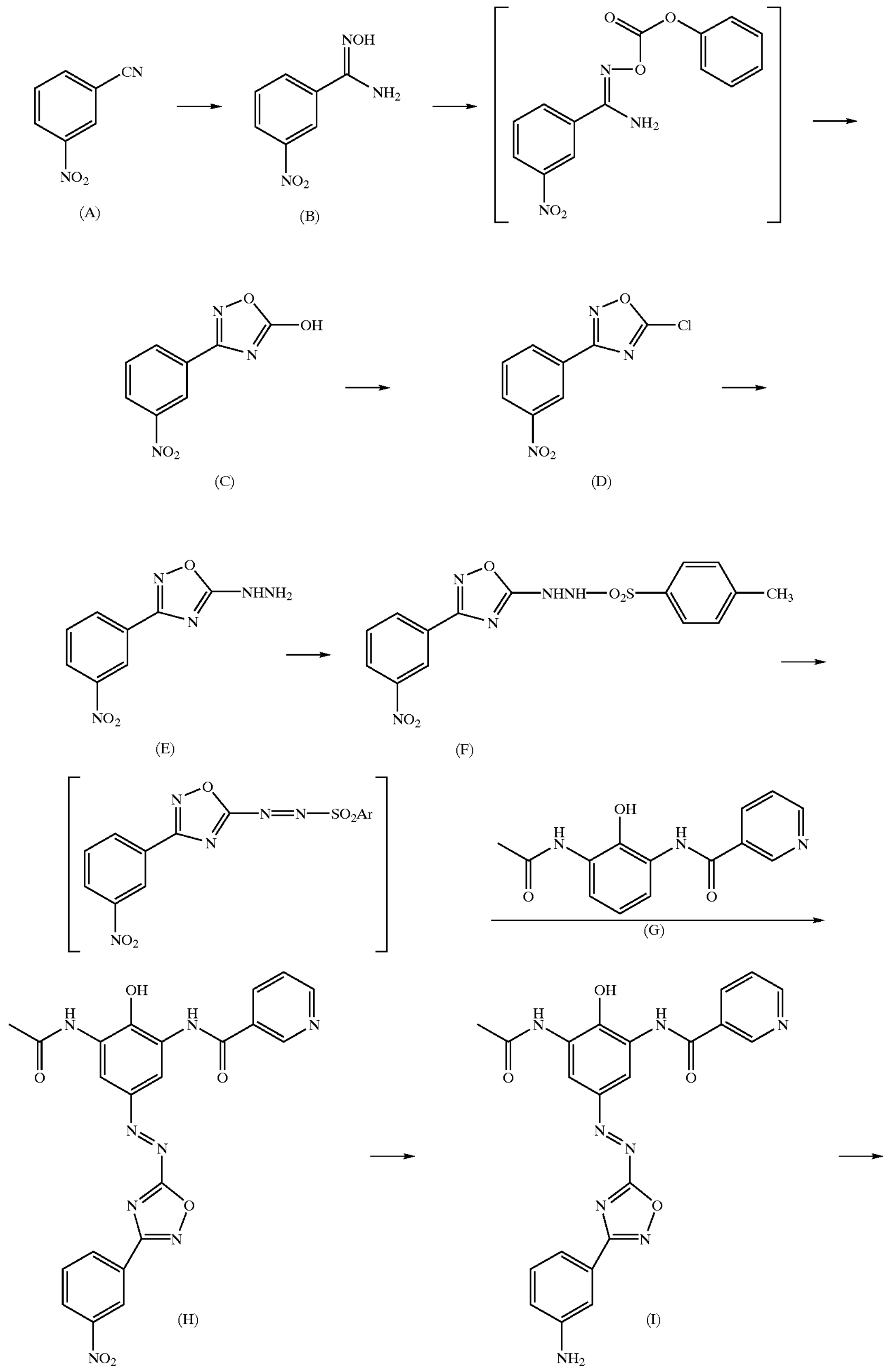
(A) (B) (C) (D) (E) (F) (G) (H) (I)

-continued

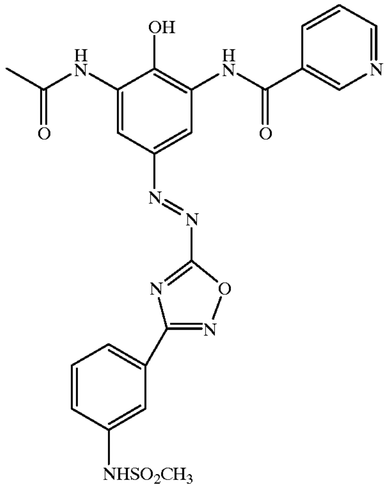

Exemplified Dye (DYE-7)

Synthesis of a Compound (B)

Into 1000 ml of ethanol was dissolved 148.12 g of a compound (A), and then 83.4 g of powder of hydroxylamine hydrochloride was added thereto at room temperature. Then, the temperature of the reaction system was raised. While the reaction system was heated under reflux, 246 ml of sodium methoxide (28% methanol solution) was dropwise added thereto over 30 minutes. Thereafter, the reaction system was heated and refluxed for 3 hours. After the reaction, the reaction solution was added to 2500 ml of ice water. Precipitated crystal was collected by filtration, and was then washed with 300 ml of water. The collected crystal was washed with 400 ml of cool isopropyl alcohol to obtain 121.5 g of the compound (B) as yellow powder.

Synthesis of a Compound (C)

Into 60 ml of N,N-dimethylacetoamide and 8.6 ml of pyridine was dissolved 18.1 g of the compound (B), and then 16.5 g of phenyl chloroformate was dropwise added thereto at room temperature over 20 minutes. During the addition, the reaction temperature rose from 24° C. to 32° C. After the addition, the temperature was raised to 60° C. and the solution was subjected to reaction for 5 hours. After the reaction, the solution was added to a mixed solution of 500 ml of water and 20 ml of concentrated hydrochloric acid. Precipitated crystal was collected by filtration, and was then washed with 300 ml of water to obtain 24.9 g of the compound (C) as pale yellow crystal.

The resultant crystal was crystal containing one molecule of N,N-dimethylacetoamide.

Synthesis of a Compound (D)

23.8 g of the compound (C) was mixed with 68.0 g of phosphorus oxychloride, and the mixture was heated. The compound (C) was completely dissolved at about 80° C. When the solution was heated to 100° C., 6.4 ml of pyridine was dropwise added thereto with sufficient attention. One hour was necessary for the addition. After the addition, the solution was subjected to reaction at 110° C. for 20 hours. After the reaction, the reaction system was cooled to room temperature, and was poured into 700 ml of ice water. Precipitated crystal was collected by filtration, and was then washed with 100 ml of water. The resultant crystal was suspended into a mixed solution of 50 ml of water and 50 ml of acetonitrile, and the suspension was stirred for 20 minutes. After the stirring, the crystal was collected by filtration, and was then washed with 20 ml of cool acetonitrile to obtain 10.4 g of the compound (D) as pale red crystal.

Synthesis of the Compound (E)

Under cooling with water, to a mixed solution of 100 ml of tetrahydrofuran and 6.5 g of water-saturated hydrazine was added 5.1 g of the compound (D) in 5 separate operations. At this time, the reaction temperature rose from 14° C. to 33° C. After the addition, the solution was subjected to further reaction for 30 minutes. After the reaction, the solution was poured into 300 ml of ice water. Precipitated crystal was collected by filtration, and was then washed with 100 ml of water to obtain 3.5 g of the compound (E) as pale red crystal.

Synthesis of the Compound (F)

Into 50 ml of N,N-dimethylacetoamide was dissolved 3.5 g of the compound (E), and under cooling with ice 3.3 g of tosyl chloride was added thereto in 7 separate operations. After the addition, the solution was subjected to further reaction for 2 hours. After the reaction, the solution was poured into a mixed solution of 200 ml of ice water and 10 ml of concentrated hydrochloric acid. Precipitated crystal was collected by filtration, and was then washed with 100 ml of water. The resultant crystal was recrystallized from acetonitrile to obtain 2.8 g of the compound (F) as white crystal.

Synthesis of the Compound (H)

Into 30 ml of ethyl acetate was dissolved 2.8 g of the compound (F), and thereto was added 6.5 g of manganese dioxide. After the addition, the solution was subjected to further reaction for 1 hour, and then the reaction solution was filtered. To the filtrate were added 50 ml of water, 20 ml of ethanol, 4.0 g of potassium carbonate and 2.2 g of the compound (G), and then the solution was vigorously stirred for 1 hour. After the reaction, the ethyl acetate phase was extracted. The organic phase was dried over anhydrous magnesium sulfate and then ethyl acetate was distilled off. The residue was subjected to silica gel chromatography to obtain 1.9 g of the compound (H) as red crystal.

Synthesis of the Compound (I)

Into 20 ml of water and 50 ml of ethanol was dissolved 1.5 g of the compound (H), and thereto was added 0.9 g of sodium hydrosulfide. The solution was heated and refluxed for 1 hour. Thereafter, the solution was poured into 100 ml of ice water. Precipitated crystal was collected by filtration, and was then washed with 30 ml of water to obtain 1.1 g of the compound (I) as red crystal.

Synthesis of the Exemplified Dye (DYE-7)

Into 20 ml of N,N-dimethylacetoamide was dissolved 1.1 g of the compound (I), and thereto was added 0.3 ml of pyridine. Thereto was added dropwise 0.25 ml of methanesulfonyl chloride at room temperature over 20 minutes. During the addition, the reaction temperature rose from 24° C. to 28° C. After the addition, the solution was subjected to further reaction for 2 hours. After the reaction, the solution was added to a mixed solution of 100 ml of water and 4 ml of concentrated hydrochloric acid. Precipitated crystal was collected by filtration, and was then washed with 50 ml of water. The resultant crystal was recrystallized from a mixed solvent of acetonitrile and methanol, to obtain 0.85 g of the exemplified dye (DYE-7) as red crystal.

The exemplified dye (DYE-69) was synthesized in accordance with the following route.

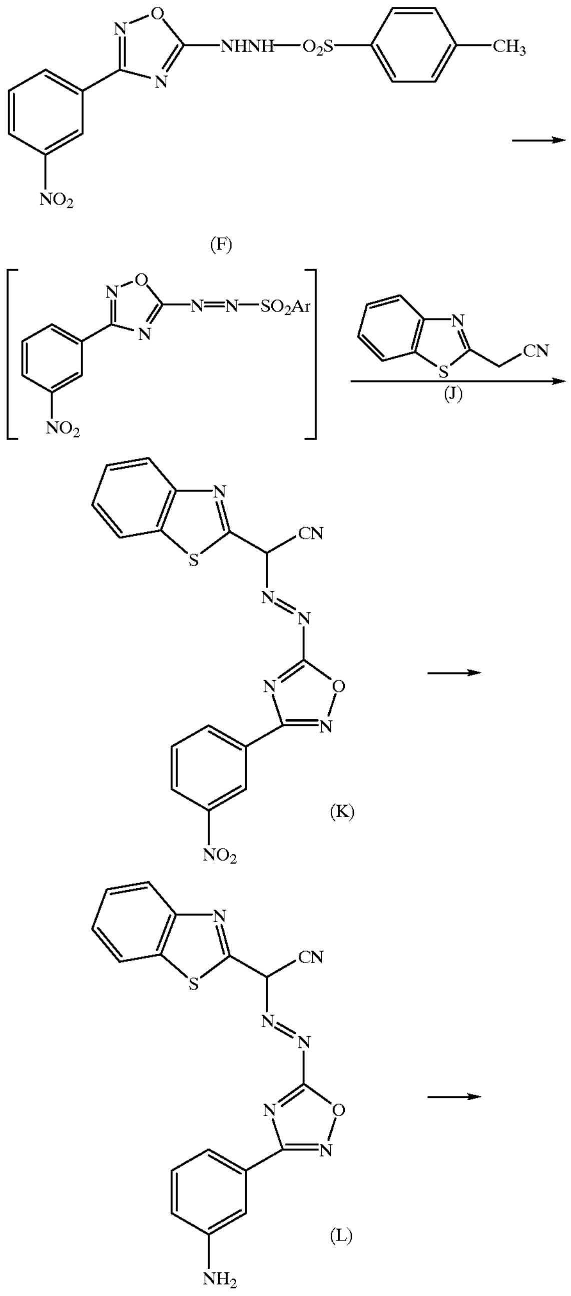

(F)

(J)

(K)

(L)

-continued

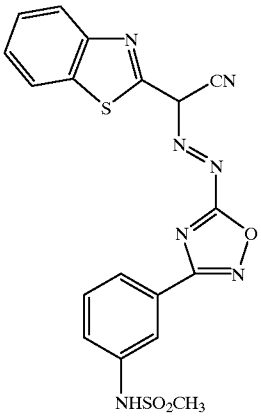

Exemplified Dye (DYE-69)

Synthesis of the Compound (K)

Into 30 ml of ethyl acetate was dissolved 2.8 g of the compound (F), and thereto was added 6.5 g of manganese dioxide. After the addition, the solution was subjected to further reaction for 1 hour, and then the reaction solution was filtered. To the filtrate were added 50 ml of water, 20 ml of ethanol, 4.0 g of potassium carbonate and 1.4 g of the compound (J), and then the solution was vigorously stirred for 1 hour. After the reaction, the ethyl acetate phase was extracted. The organic phase was dried over anhydrous magnesium sulfate and then ethyl acetate was distilled off. The residue was subjected to silica gel chromatography to obtain 2.2 g of the compound (K) as yellow crystal.

Synthesis of the Compound (L)

Into 20 ml of water and 50 ml of ethanol was dissolved 2.2 g of the compound (K), and thereto was added 1.6 g of sodium hydrosulfide. The solution was heated and refluxed for 1 hour. Thereafter, the solution was poured into 100 ml of ice water. Precipitated crystal was collected by filtration, and was then washed with 30 ml of water to obtain 1.6 g of the compound (L) as yellow crystal.

Synthesis of the Exemplified Dye (DYE-69)

Into 20 ml of N,N-dimethylacetoamide was dissolved 1.6 g of the compound (L), and thereto was added 0.4 ml of pyridine. Thereto was added dropwise 0.36 ml of methanesulfonyl chloride at room temperature over 20 minutes. During the addition, the reaction temperature rose from 24° C. to 27° C. After the addition, the solution was subjected to further reaction for 2 hours. After the reaction, the solution was added to a mixed solution of 100 ml of water and 4 ml of concentrated hydrochloric acid. Precipitated crystal was collected by filtration, and was then washed with 50 ml of water. The resultant crystal was recrystallized from acetonitrile, to obtain 1.1 g of the exemplified dye (DYE-69) as yellow crystal.

The following will describe a method of synthesizing the image-forming compound used in the present invention.

The image-forming compound to be used in the present invention can easily be synthesized with reference to synthesis methods described in the patent publications referred to to explain the formula (2-5).

Specific synthesis examples according to the present invention will be described hereinafter, but the present invention is not limited to these examples.

The exemplified compound (K-1) was synthesized in accordance with the following route.

The compound (M) was synthesized with reference to the synthesis example of the above-mentioned dye.

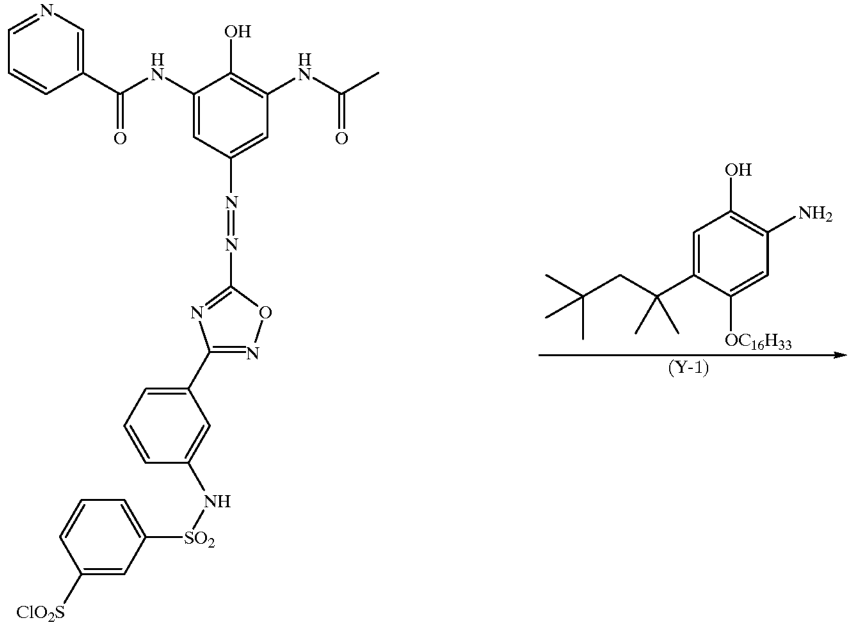

(M)

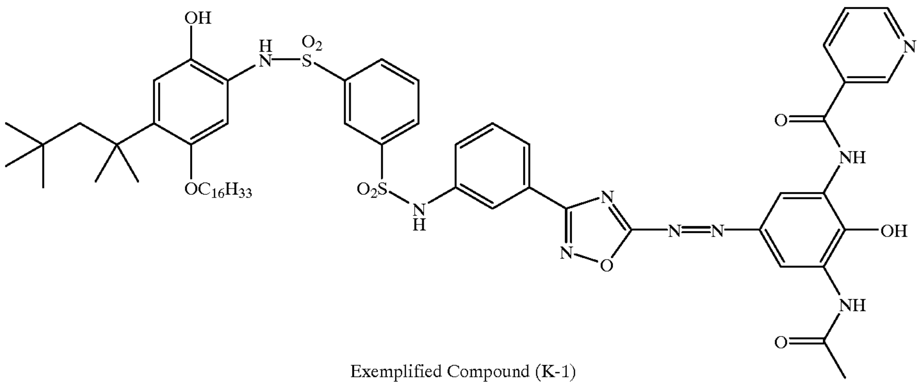

Exemplified Compound (K-1)

Synthesis of the Exemplified Compound (K-1)

Under the atmosphere of nitrogen, 2.81 g of the compound (Y-1) was dissolved in 50 ml of N,N-dimethylacetoamide, and then 1.0 ml of pyridine was added thereto. Then, 6.94 g of the compound (M) was added thereto under cooling with ice, and then the solution was stirred for 1 hour. After the reaction, 500 ml of ethyl acetate and 500 ml of water were added thereto, so as to perform extraction. The organic phase was dried over anhydrous magnesium sulfate, and subsequently ethyl acetate was distilled off. The residue was subjected to silica gel chromatography, to obtain 6.8 g of the exemplified compound (K-1) as red crystal.

The color-developing agent of the present invention is used together with a compound (a coupler) that can form a dye by oxidation coupling reaction. This coupler may be a so-called "four-equivalent coupler" or "two-equivalent coupler", which is used in a conventional system using a p-phenylenediamine-series developing agent. Specific examples of the coupler are described in detail, for example, in "Theory of The Photographic Process" (4th Ed., edited by T. H. James, Macmillan, 1977), pages 291 to 334 and 354 to 361, and in JP-A-58-12353, JP-A-58-149046, JP-A-58-149047, JP-A-59-11114, JP-A-59-124399, JP-A-59-174835, JP-A-59-231539, JP-A-59-231540, JP-A-60-2951, JP-A-60-14242, JP-A-60-23474, and JP-A-60-66249, and in Research Disclosure No. 37038 (February, 1995) on pages 80–83, and ibid. No. 40145 (September, 1997) on pages 614–617.

Examples of a coupler that is preferably used in the present invention include exemplified compounds (C-1) to (C-80) described in JP-A-8-286340, and couplers represented by formulae (1) to (12) and preferably exemplified compounds (C-1) to (C-50) described in JP-A-9-152705, but the present invention is not limited to them.

Further, the below-shown couplers (Cp-1) to (Cp-14) can also be mentioned as examples of the preferable coupler for use in the present invention.

(Cp-1)
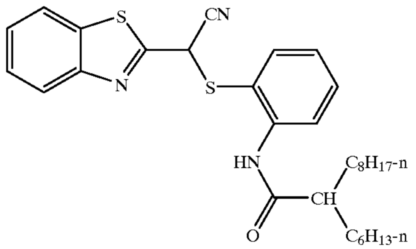
(Cp-2)
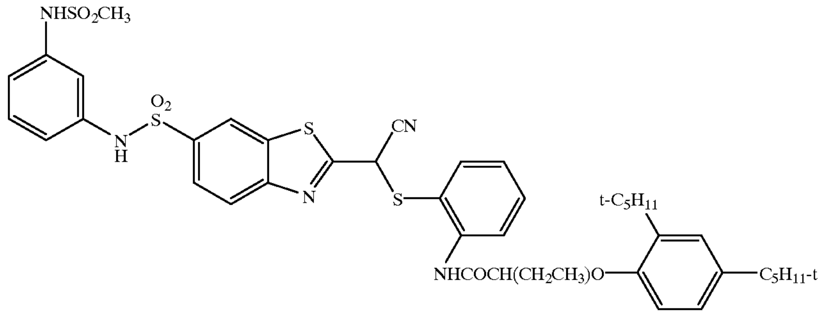
(Cp-3)
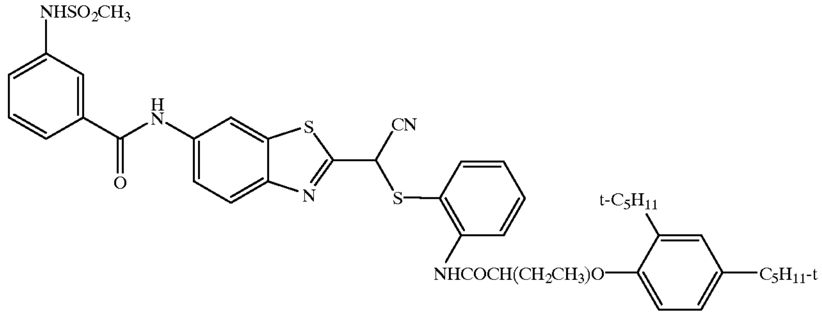
(Cp-4)
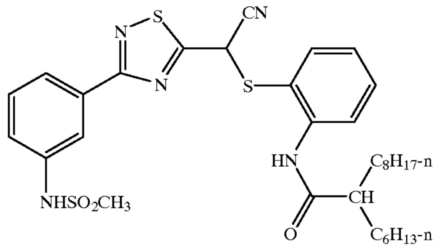
(Cp-5)
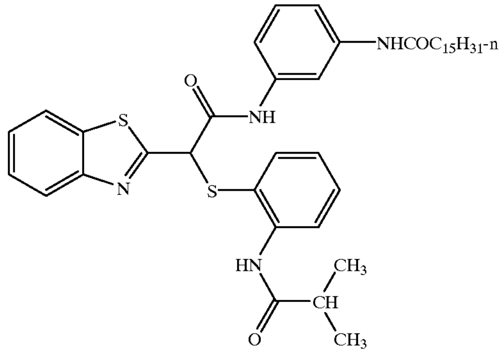

-continued
(Cp-6)
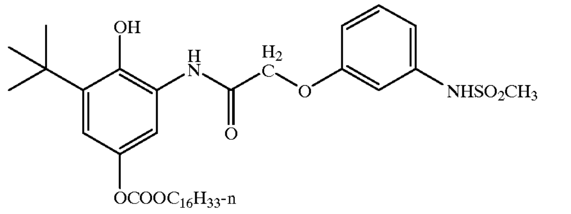
(Cp-7)
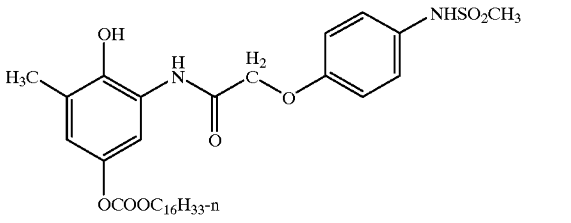
(Cp-8)
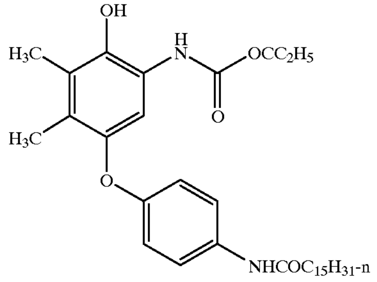
(Cp-9)
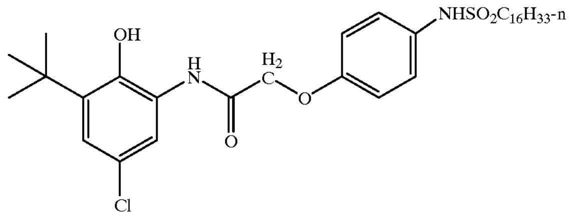
(Cp-10)
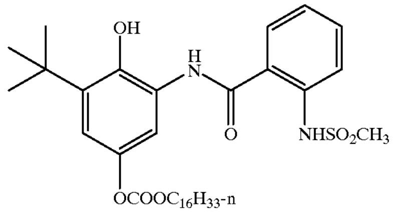
(Cp-11)
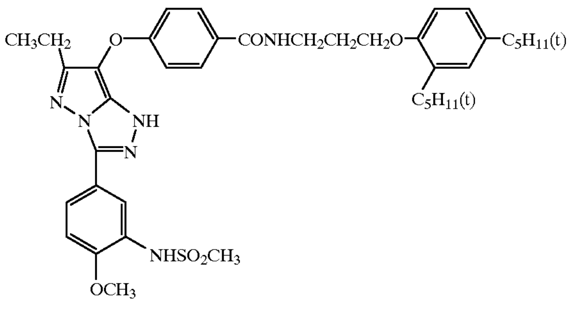

-continued (Cp-12)

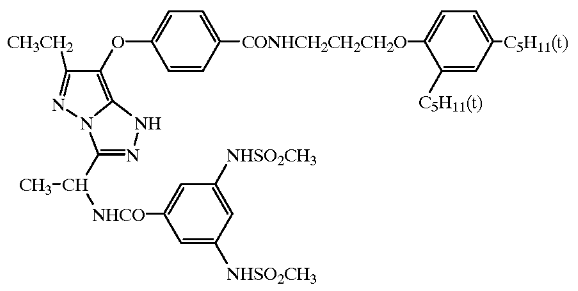

(Cp-13)

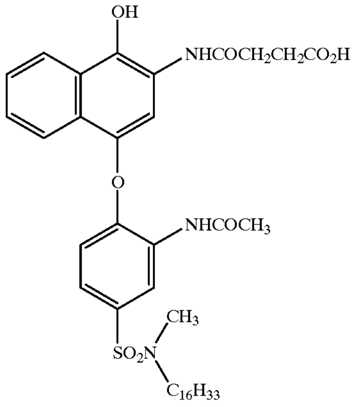

(Cp-14)

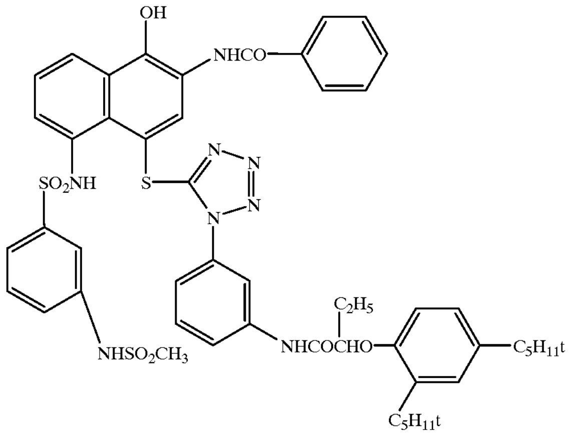

The amount to be added of the coupler that is used with the color-developing agent of the present invention, varies according to the molar extinction coefficient (ε) of a produced dye. In order to obtain an image density of 1.0 or more in terms of reflection density, in the case of a coupler wherein the ε of the dye that will be produced by coupling is of the order of 5,000 to 500,000, suitably the amount to be added of the coupler that is used in the present invention, is of the order of generally 0.01 to 10 mmol/$m^2$, and preferably 0.05 to 5 mmol/$m^2$, in terms of the coated amount.

In the case that the color-developing agent of the present invention is incorporated into a light-sensitive material, the developing agent may be added to any layer thereof (for example, a silver halide emulsion layer or an intermediate layer). Preferably, the developing agent is incorporated into a silver halide emulsion layer. In the case that plural silver halide emulsion layers are present, the developing agent is preferably incorporated into all thereof.

The amount of the color-developing agent of the present invention to be added is generally 0.01 to 100 times, preferably 0.2 to 5 times, the amount of the coupler in molar ratio.

The developing agent may be used by incorporating into a processing solution instead of a light-sensitive material. In this case, the developing agent is incorporated preferably in an amount of 0.1–100 g and more preferably in an amount of 1–20 g, per liter of the processing solution.

In the present invention, an auxiliary developing agent can be used. Herein the term "an auxiliary developing agent" means a substance that functions to accelerate the transfer of electrons from the color-developing agent to silver halides in the development process of the silver halide development; and the auxiliary developing agent is a compound capable of releasing electrons according to the Kendall-Pelz rule.

The auxiliary developing agent in the present invention is preferably any one of compounds represented by the formulae (B-1) and (B-2), described in JP-A-08-286340. Examples thereof include ETA-1 to ETA-36 described in JP-A-08-286340. Compounds represented by the formula (1) described in JP-A-09-146248 are also preferred. Examples thereof include exemplified compounds D-1 to D-35 described in JP-A-09-146248.

In the present invention, a blocked photographic reagent that will release a photographically useful group at the time of processing can be used. Examples of these are described in detail on pages 41 to 42 of JP-A-09-152704.

The light-sensitive material of the first embodiment of the present invention, preferably, has on a base, a photosensitive silver halide, at least one color-developing agent represented by the above formula (1-1), a coupler, and a binder, and, if required, an organometal salt oxidizing agent, and the like can be contained. In many cases, these components are added to the same layer, but they can be separately added to different layers if they are in reactive states.

The light-sensitive material, preferably heat-developable color light-sensitive material of the second embodiment of the present invention basically has on a base, a light-sensitive silver halide emulsion, and a binder, and, if required, an organometal salt oxidizing agent, a dye-providing compound (for example, the compound of formula (2-5); a reducing agent may have this function as described later), or the like can be contained.

These components are added to the same layer in many cases, but they may be added to separate layers. For example, when a colored dye-providing compound is allowed to present in a layer lower than a silver halide emulsion layer, the sensitivity can be prevented from lowering.

Further, a reducing agent is preferably built in the heat-developable light-sensitive material, but it may be supplied from the outside, for example, by a method wherein it is diffused from a dye-fixing element as described later.

Hydrophobic additives such as a coupler, a color-developing agent, a dye-providing compound, and a non-diffusion reducing agent, which are used in the present invention may be introduced into the layers of the light-sensitive material (i.e. photographic constitutional layers such as hydrophilic colloid layer) by a known method such as a method described in U.S. Pat. No. 2,322,027. When these compounds are to be introduced into the layers, a high-boiling point organic solvent as described in U.S. Pat. Nos. 4,555,470, 4,536,466, 4,536,467, 4,587,206, 4,555,476, 4,599,296, JP-B-3-62256 may be used, as required, together with a low-boiling point organic solvent having a boiling point as low as 50° C. to 160° C. Further, these dye-providing compounds such as a coupler and a color-developing agent, nondiffusion reducing agents, high-boiling organic solvents, and the like each can be used singly, or in the form of a combination of two or more. As the case of color-developing agents, the compound represented by formula (1-1) can be used in combination with another compound that is not included in the formula.

The amount of the high-boiling point organic solvent to be used is generally 10 g or less, preferably 5 g or less, and more preferably 1 g to 0.1 g, per g of a dye-providing compound to be used. The amount of the solvent is preferably 1 ml or less, more preferably 0.5 ml or less and particularly preferably 0.3 ml or less, per g of the binder.

A dispersion method that use a polymer, as described in JP-B-51-39853 and JP-A-51-59943, and a method wherein the addition is made with them in the form of a dispersion of fine particles, as described, for example, in JP-A-62-30242 and JP-A-63-271339, can also be used.

If the compounds are substantially insoluble in water, besides the above methods, a method can be used wherein the compounds may be made into fine particles to be dispersed and contained in a binder.

In dispersing the hydrophobic compound in a hydrophilic colloid, various surface-active agents can be used. For example, surface-active agents described in JP-A-59-157636, pages (37) to (38), and in the RD publications shown in a table below, can be used.

In the photographic material of the present invention, use can be made of a compound that can activate the development and make the image stable. Preferable specific compounds for use are described in U.S. Pat. No. 4,500,626, the 51st column to the 52nd column.

In order to obtain colors ranging widely on the chromaticity diagram by using three primary colors: yellow, magenta, and cyan, use is made of a combination of at least three silver halide emulsion layers photosensitive to respectively different spectral regions. For example, a combination of a blue-sensitive layer, a green-sensitive layer, and a red-sensitive layer, and a combination of a green-sensitive layer, a red-sensitive layer, and an infrared-sensitive layer, and a combination of a red-sensitive layer, an infrared-sensitive layer (1), and an infrared-sensitive layer (2), as described in JP-A-59-180550, JP-A-64-13546, JP-A-62-253159, and EP-A-479,167, can be mentioned. Each of the photosensitive layers can be arranged in various orders known generally for color photographic materials. Further, each of these photosensitive layers can be divided into two or more layers if necessary, as described in JP-A-1-252954. In the heat-developable light-sensitive material, various non-light-sensitive layers can be provided, such as a protective layer, an underlayer, an intermediate layer, a yellow filter layer, and an antihalation layer, between the above silver halide emulsion layers, or as an uppermost layer or a lowermost layer; and on the opposite side of the photographic support, various auxiliary layers can be provided, such as a backing layer. Specifically, for example, layer constitutions as described in the above-mentioned patent publications, undercoat layers as described in U.S. Pat. No. 5,051,335, intermediate layers containing a solid pigment, as described in JP-A-1-167,838 and JP-A-61-20,943, intermediate layers containing a reducing agent or a DIR compound, as described in JP-A-1-129,553, JP-A-5-34,884, and JP-A-2-64,634, intermediate layers containing an electron-transfer agent, as described in U.S. Pat. Nos. 5,017,454 and 5,139,919, and JP-A-2-235,044, protective layers containing a reducing agent, as described in JP-A-4-249,245, or combinations of these layers, can be provided. It is preferable to design a support so that it has antistatic function and the surface resistivity of $10^{12}$ Ω.cm or less. Further, in order to improve the color separation, various filter dyes can be added.

The silver halide grains used in the present invention are made of silver bromide, silver chloride, silver chlorobromide, silver chloroiodide, silver iodobromide, or silver chloroiodobromide. Other silver salts, such as silver rhodanate, silver sulfide, silver selenide, silver carbonate, silver phosphate, or a silver salt of an organic acid, may be contained in the form of independent grains or as part of silver halide grains. If it is desired to make the development/desilvering (bleaching, fixing, and bleach-fix) step rapid, silver halide grains having a high silver chloride content are desirable. Further, if the development is to be restrained moderately, it is preferable to contain silver iodide. The preferable silver iodide content varies depending on the intended photographic material. For example, in the case of X-ray photographic materials, the preferable silver iodide content is in the range of 0.1 to 15 mol %, and in the case of graphic art and micro photographic materials, the preferable silver iodide content is in the range of 0.1 to 5 mol %. In the case of photographic materials for shooting represented by color negatives, preferably silver halide contains 1 to 30 mol %, more preferably 5 to 20 mol %, and particularly preferably 8 to 15 mol %, of silver iodide. It is preferable to incorporate silver chloride in silver iodobromide grains, because the lattice strain can be made less intense.

The silver halide emulsion that is used in the present invention may be a surface-latent-image-type emulsion or an internal-latent-image-type emulsion. The internal-latent-image-type emulsion is used in combination with a nucleator or a light-fogging agent to be used as a direct reversal emulsion. When the silver halide grains contained in the silver halide emulsion for use in the present invention are composed of a mixed crystal of different silver halides, the grains having uniform composition in the individual grain can be used, but it is also preferably performed to make the grains have what is called a lamination layer structure, having multiple layers with different halogen compositions within the individual grain. Examples of the latter include a so-called core-shell emulsion having different compositions in the inner part and surface layer of the grain. Further, in addition to the lamination layer structure as mentioned above, a structure having a localized phase with a different halogen composition within the individual grain can also be preferably used. Preferable examples of the grains having such a structure include grains in which, on the surface, edge, or top of an individual silver halide grain as the mother body, a silver halide with different composition is joined by epitaxial joining. Further, it is also preferable to form the localized phase in the inner parts of the grain. The silver halide grains that constitute the silver halide emulsion may have a monodisperse or a polydisperse distribution of grain size. A technique is preferably used wherein the gradation is adjusted by mixing monodispersed emulsions having different grain size or sensitivity, as described in JP-A-1-167743 or JP-A-4-223463. The grain size is preferably 0.1 to 2 $\mu$m, and particularly preferably 0.2 to 1.5 $\mu$m. The crystal habit of the silver halide grains may be any of regular crystals, such as cubic crystals, octahedral crystals and tetradecahedral crystals; irregular crystals, such as spherical crystals and tabular crystals having a high aspect ratio; crystals having crystal defects, such as twin planes, composite crystals of these, or others.

The grains of the silver halide emulsion for use in the present invention preferably have a distribution or a structure with respect to the halogen composition. Typical examples thereof are grains having a double structure, or core-shell-type grains wherein the halogen composition is different in the surface layer and the inside part of the grains, as disclosed, respectively, in JP-B-43-13162, JP-A-61-215540, JP-A-60-222845, and JP-A-61-75337. Instead of a simple double structure, a triple structure, as described in JP-A-60-222844, an even larger-number multilayer structure, or a structure wherein the surface of grains having a core-shell double structure has a thin silver halide layer different in composition from that of the said surface, can be used.

In order to make the inside of grains have a structure, not only the enclosing structure, as mentioned above, but also a so-call Functioned structure can be used to form grains. Examples thereof are disclosed, for example, in JP-A-59-133540, JP-A-58-108526, European Patent No. 199 290 (A2), JP-B-58-24772, and JP-A-59-16254. Crystals to be Functioned have a composition different from that of host crystals, and they can be junctioned and formed at the edges, corners, or planes of the host crystals. Such Functioned crystals can be formed if host crystals have a uniform halogen composition or a core-shell-type structure.

In the case of a Functioned structure, not only a combination of silver halides but also a combination of a silver halide with a silver salt compound having no rock salt structure, such as silver rhodanate and silver carbonate, can be used for the Functioned structure. A non-silver salt compound, such as lead oxide, may be used if a junctioned structure is possible.

In the case of grains of silver iodobromide or the like having these structures, a preferable mode is that the core part is higher in silver iodide content than the shell part. Reversely, in some cases, grains having a lower silver iodide content in the core part than in the shell part are preferable. Similarly, in the case of grains having a Functioned structure, the silver iodide content of the host crystals is relatively higher than that of the junctioned crystals, or this may be reversed. The boundary part of the grains having these structures in which different halogen compositions are present, may be distinct or indistinct. Also preferable is a mode wherein the composition is continuously changed positively.

It is important that in the case of that two or more silver halides are present as mixed crystals, or as silver halide grains having structures, the halogen composition distribution amoung grains is controlled. The method of measuring the halogen composition distribution among grains is described in JP-A-60-254032. A desirable property is that the halogen distribution among grains is uniform. In particular, a highly uniform emulsion having a deviation coefficient of 20% or below is preferable. Another preferable mode is an emulsion in which the grain size and the halogen composition are correlated. An example correlation is a larger grain size with a larger iodine content, and vice versa (smaller grain size, lower iodine content). Depending on the purpose, the reversed correlation or a correlation using some other halogen composition can be used. For this purpose, it is preferable to mix two or more emulsions different in composition.

It is important to control the silver halide composition near the surface of grains. An increase in the silver iodide content or the silver chloride content at the part near the surface changes the adsorption of a dye or the developing speed. Therefore, the silver halide composition can be chosen in accordance with the purpose. To change the halogen composition at the part near the surface, either the structure enclosing the whole of a grain or the structure wherein only part of a grain is attached to another silver halide different in halogen composition, can be chosen. For example, in the case of a tetradecahedral grain having (100) and (111) planes, only one plane is changed in halogen composition, or in another case, one of the main face and the side face of a tabular grain is changed in halogen composition.

In the silver halide grains used in the present invention, in accordance with the purpose, any of regular crystals having no twin plane, and those described in "Shashin Kogyo no Kiso, Ginen Shashin-hen", edited by Nihon Shashin-gakkai (Corona Co.), page 163, such as single twins having one twin plane, parallel multiple twins having two or more parallel twin planes, and nonparallel multiple twins having two or more nonparallel twin planes, can be chosen and used. An example in which grains different in shape are mixed is disclosed in U.S. Pat. No. 4,865,964, and if necessary this method can be chosen. In the case of regular crystals, cubes having (100) planes, octahedrons having (111) planes, and dodecahedral grains having (110) planes, as disclosed in JP-B-55-42737 and JP-A-60-222842, can be used. Further, (h11) plane grains represented by (211), (hh1) plane grains represented by (331), (hk0) plane grains represented by (210) planes, and (hk1) plane grains represented by (321) planes, as reported in "Journal of Imaging Science", Vol. 30, page 247 (1986), can be chosen and used in accordance with the purpose, although the preparation is required to be adjusted. Grains having two or more planes in one grain, such as tetradecahedral grains having (100) and (111) planes in one grain, grains having (100) and (110) planes in one grain, or grains having (111) and (110) planes in one grain, can be chosen and used in accordance with the purpose.

The value obtained by dividing the diameter of the projected area, which is assumed to be a circle equivalent in area, by the thickness of the grain, is called an aspect ratio, which defines the shape of tabular grains. Tabular grains having an aspect ratio of more than 1 can be used in the present invention. Tabular grains can be prepared by methods described, for example, by Cleav in "Photography Theory and Practice" (1930), page 131; by Gutof in "Photographic Science and Engineering", Vol. 14, pages 248 to 257 (1970); and in U.S. Pat. Nos. 4,434,226, 4,414,310, 4,433,048, and 4,439,520, and British Patent No. 2 112 157. When tabular grains are used, such merits are obtained that the covering power is increased and the color sensitization efficiency due to a sensitizing dye is increased, as described in detail in the above-mentioned U.S. Pat. No. 4,434,226. The average aspect ratio of 80% or more of all the projected areas of grains is preferably 1 or more but less than 100, more preferably 2 or more but less than 20, and particularly preferably 3 or more but less than 10. As the shape of average grains, a triangle, a hexagon, a circle, and the like can be chosen. A regular hexagonal shape having six approximately equal sides, described in U.S. Pat. No. 4,798,354, is a preferable mode.

In many cases, the grain size of tabular grains is expressed by the diameter of the projected area assumed to be a circle, and grains having an average diameter of 0.6 $\mu$m or below, as described in U.S. Pat. No. 4,748,106, are preferable, because the quality of the image is made high. An emulsion having a narrow grain size distribution, as described in U.S. Pat. No. 4,775,617, is also preferable. It is preferable to restrict the shape of tabular grains so that the thickness of the grains may be 0.5 $\mu$m or below, and more preferably 0.3 $\mu$m or below, because the sharpness is increased. Further, an emulsion in which the grains are highly uniform in thickness, with the deviation coefficient of grain thickness being 30% or below, is also preferable. Grains in which the thickness of the grains and the plane distance between twin planes are defined, as described in JP-A-63-163451, are also preferable.

In the case of tabular grains, the dislocation lines can be observed by a transmission electron microscope. In accordance with the purpose, it is preferable to choose grains having no dislocation lines, grains having several dislocation lines, or grains having many dislocation lines. Dislocation introduced straight in a special direction in the crystal orientation of grains, or curved dislocation, can be chosen, and it is possible to choose from, for example, dislocation introduced throughout grains, dislocation introduced in a particular part of grains, and dislocation introduced limitedly to the fringes of grains. In addition to the case of introduction of dislocation lines into tabular grains, also preferable is the case of introduction of dislocation lines into regular crystalline grains or irregular grains, represented by potato grains. In this case, a preferable mode is that introduction is limited to a particular part of grains, such as vertexes and edges.

The silver halide emulsion used in the present invention may be subjected to a treatment for making grains round, as disclosed, for example, in European Patent No. 96 412(B1), or it may be improved in the surface, as disclosed in West Germany Patent No. 2 306 447(C2) and JP-A-60-221320.

Generally, the grain surface has a flat structure, but it is also preferable in some cases to make the grain surface uneven intentionally. Examples are a technique in which part of crystals, for example, vertexes and the centers of planes, are formed with holes, as described in JP-A-58-106532 and JP-A-60-221320, and ruffled grains, as described in U.S. Pat. No. 4,643,966.

The grain size of the emulsion used in the present invention is evaluated, for example, by the diameter of the projected area equivalent to a circle using an electron microscope; by the diameter of the grain volume equivalent to a sphere, calculated from the projected area and the grain thickness; or by the diameter of a volume equivalent to a sphere, using the Coulter Counter method. A selection can be made from ultrafine grains having a sphere-equivalent diameter of 0.05 $\mu$m or below, and coarse grains having a sphere-equivalent diameter of 10 $\mu$m or more. Preferably, grains of 0.1 $\mu$m or more but 3 $\mu$m or below are used as photosensitive silver halide grains.

As the emulsion used in the present invention, an emulsion having a wide grain size distribution, that is, a so-called polydisperse emulsion, or an emulsion having a narrow grain size distribution, that is, a so-called monodisperse emulsion, can be chosen and used in accordance with the purpose. As the scale for representing the size distribution, the diameter of the projected area of the grain equivalent to a circle, or the deviation coefficient of the sphere-equivalent diameters, is used. If a monodisperse emulsion is used, it is good to use an emulsion having such a size distribution that the deviation coefficient is preferably 25% or below, more preferably 20% or below, and further more preferably 15% or below.

In some cases, a monodisperse emulsion is defined by the average grain size distribution based on the weight or number of grains. Further, in order to allow the photographic material to satisfy the intended gradation, in an emulsion layer having substantially the same color sensitivity, two or more monodisperse silver halide emulsions different in grain size are mixed and applied to the same layer or are applied as overlaid layers. Further, two or more polydisperse silver halide emulsions can be used as a mixture; or they can be used to form overlaid layers; or a combination of a monodisperse emulsion and a polydisperse emulsion can be used as a mixture; or the combination can be used to form overlaid layers.

As an emulsion used in the present invention, use can be made of an emulsion containing the above grains. One mode of carrying out the present invention is that the color-developing agent of the present invention and the emulsion comprising tabular grains whose silver chloride content is 50 mol % or more, are not used in combination.

As the photographic emulsion used in the present invention, specifically, any of silver halide emulsions can be used that are prepared by methods described, for example, in U.S. Pat. No. 4,500,626, column 50; U.S. Pat. No. 4,628,021, Research Disclosure (hereinafter abbreviated to as RD) No. 17,029 (1978), RD No. 17,643 (December 1978), pages 22 to 23; RD No. 18,716 (November 1979), page 648; RD No. 307,105 (November 1989), pages 863 to 865; JP-A-62-253159, JP-A-64-13546, JP-A-2-236546, and JP-A-3-110555; and by P. Glafkides in "Chemie et Phisique Photographique," Paul Montel, 1967; by G. F. Duffin in "Photographic Emulsion Chemistry," Focal Press, 1966; or by V. L. Zelikman et al. in "Making and Coating Photographic Emulsion," Focal Press, 1964, can be used. That is, any of the acid process, the neutral process, the ammonia process, and the like can be used; and to react a soluble silver salt with a soluble halogen salt, any of the single-jet method, the double-jet method, a combination thereof, and the like can be used. In order to obtain a monodisperse emulsion, the double-jet method is preferably used. A method wherein grains are formed in the presence of excess silver ions (the so-called reverse precipitation process) can also be used. As one type of the double-jet method, a method wherein pAg in the liquid phase, in which a silver halide will be formed, is kept constant, that is, the so-called controlled double-jet method, can also be used. According to this method, a silver halide emulsion wherein the crystals are regular in shape and whose grain size is approximately uniform, can be obtained.

A method in which previously precipitated silver halide grains are added to a reaction vessel for the preparation of an emulsion, and the methods described, for example, in U.S. Pat. Nos. 4,334,012, 4,301,241, and 4,150,994, are preferable in some cases. These can be used as seed crystals, or they are effective when they are supplied as a silver halide for growth. In the latter case, it is preferable to add an emulsion whose grains are small in size, and as an addition method, one of the following can be chosen: all of the volume is added at one stroke, or the volume is separated and added in portions, or it is added continuously. Further, in some cases, it is also effective to add grains having different halogen compositions in order to modify the surface.

It is preferably performed that the light-sensitive silver halide emulsion for use in the present invention is made to contain an ion of a transition metal, such as titanium, iron, cobalt, ruthenium, rhodium, osmium, iridium, and platinum, or an ion of a typical metal, such as zinc, cadmium, thallium, and lead, in the inner part or surface of the grain, for the various purposes of high sensitivity, contrasting, improving reciprocity law failure, improving latent image stability, improving pressure durability, and the like. These metal ions can be introduced in the form of salts or complex salts. In particular, when the transition metal ion is contained, it is preferable to use it as complexes having ammonia, halogens, cyan, thiocyan, nitrosyl, and the like, as ligands, or complexes having organic ligands, such as imidazole, triazole, pyridine, bipyridine and the like, as ligands. These ligands can be used singly or in combination of multiple kinds of ligands. Moreover, it is also possible to use these compounds singly or in combination of two or more kinds. The amount to be added varies depending on the purpose of the application; but the amount is generally on the order of 10 to 10 mol per mol of the silver halide. When they are incorporated, they may be incorporated uniformly in the grains, or they may be localized in the grains or on the surface of the grains. Specifically, emulsions described, for example, in JP-A-2-236542, JP-A-1-116637, and JP-A-5-181246 are preferably used.

The method in which a large part or only a small part of the halogen composition of silver halide grains is converted by the halogen conversion method is disclosed, for example, in U.S. Pat. Nos. 3,477,852 and 4,142,900, European Patent Nos. 273 429 and 273 430, and West German Publication Patent No. 3 819 241, and it is an effective method for forming grains. To convert to a more hardly soluble silver salt, it is possible to add a solution of a soluble halogen or to add silver halide grains. Selection can be made from respective methods in which the conversion is made at one stroke, in several steps, and continuously.

In addition to the method in which the grain growth is made by adding a soluble silver salt and a halogen salt at constant concentrations and at constant flow rates, grain formation methods wherein the concentration is changed or the flow rate is changed, as described in British Patent No. 1 469 480 and U.S. Pat. Nos. 3,650,757 and 4,242,445, are preferable methods. By changing the concentration or increasing the flow rate, the amount of the silver halide to be supplied can be changed as a linear function, a quadratic function, or a more complex function, of the addition time. Further, if required, the amount of the silver halide to be supplied is decreased, which is preferable in some cases. Also effective is an addition method wherein, when several soluble silver salts different in solution composition are added, or when several soluble halogen salts different in solution composition are added, one of them is increased and the other is decreased.

Further, to quicken the growth of the grains, the concentrations, the amounts, and the speeds of the silver salt and the halide to be added may be increased (e.g. JP-A-55-142329, JP-A-55-158124, and U.S. Pat. No. 3,650,757).

As the method of stirring the reaction liquid, any of known stirring methods may be used. The temperature and the pH of the reaction liquid during the formation of the silver halide grains may be set arbitrarily to meet the purpose. Preferably the pH range is 2.3 to 8.5, and more preferably 2.5 to 7.5.

A mixing vessel that is used when a solution of a soluble silver salt and a solution of a soluble halogen salt are reacted can be selected for use from methods described in U.S. Pat. Nos. 2,996,287, 3,342,605, 3,415,650, and 3,785,777, and West German Publication Patent Nos. 2 556 885 and 2 555 364.

For the purpose of promoting the ripening, a silver halide solvent is useful. For example, it is known to allow an excess amount of halide ions to be present in the reaction vessel, to accelerate the ripening. Further, other ripening agent can be used. All of the amount of these ripening agents may be blended in the dispersion medium in the reaction vessel before silver and halide salts are added, or their introduction into the reaction vessel may be carried out together with the addition of a halide, a silver salt, or a peptitizer. As another modified mode, a method is possible wherein a ripening agent is added independently at the step of adding a halide salt and a silver salt.

In the step for forming grains of the light-sensitive silver halide emulsion for use in the present invention, as a silver halide solvent, a rhodanate, ammonia, a tetrasubstituted thioether compound, an organic thioether derivative described in JP-B-47-11386, or a sulfur-containing compound described in JP-A-53-144319 can be used.

For example, ammonia, thiocyanates (e.g. potassium rhodanate and ammonium rhodanate), organic thioether compounds (e.g. compounds described, for example, in U.S. Pat. Nos. 3,574,628, 3,021,215, 3,057,724, 3,038,805, 4,276,374, 4,297,439, 3,704,130, and 4,782,013, and JP-A-57-104926), thion compounds (e.g. tetra-substituted thioureas described, for example, in JP-A-53-82408 and JP-A-

55-77737, and U.S. Pat. No. 4,221,863; and compounds described in JP-A-53-144319), mercapto compounds capable of promoting the growth of silver halide grains, as described in JP-A-57-202531, and amine compounds (e.g. described in JP-A-54-100717), can be mentioned.

As a protective colloid used in the preparation of the emulsion for use in the present invention, and as another binder of the hydrophilic colloid layer (e.g. structural layers in the heat-developable light-sensitive material or the dye-fixation material) a hydrophilic binder is preferably used. Examples thereof include those described in the above Research Disclosures and on pages (71)–(75) of JP-A-64-13546. Specifically, a transparent or semitransparent hydrophilic binder is preferred, and gelatin is used advantageously, but another hydrophilic colloid can also be used.

Use can be made of, for example, a gelatin derivative, a graft polymer of gelatin with another polymer, a protein, such as albumin and casein; a cellulose derivative, such as hydroxycellulose, carboxymethylcellulose, and cellulose sulfate; sodium alginate, a starch derivative, acacia, a saccharide derivative of a natural compound, such as a polysaccharide, including dextran and pullulan; and many synthetic hydrophilic polymers, including homopolymers and copolymers, such as a polyvinyl alcohol, a polyvinyl alcohol partial acetal, a poly-N-vinylpyrrolidone, a polyacrylic acid, a polymethacrylic acid, a polyacrylamide, a polyvinylimidazole, and a polyvinylpyrazole. Further, use can be made of a high-water-absorptive polymer described, for example, in U.S. Pat. No. 4,960,681 and JP-A-62-245,260, that is, a copolymer of a vinyl monomer having —$COOM^1$ or —$SO_3M^1$ (wherein $M^1$ represents a hydrogen atom or an alkali metal), or a copolymer of these vinyl monomers, or a copolymer of this vinyl monomer with another vinyl monomer (e.g. sodium methacrylate, ammonium methacrylate, and Sumikagel L-5H (trade name; manufactured by Sumitomo Chemical Co., Ltd.)). Two or more of these binders can be used in combination. A combination of gelatin with any of these binders is also preferable.

As the gelatin, one of lime-processed gelatin, acid-processed gelatin, and so-called de-ashed gelatin wherein the content of calcium or the like is reduced, can be selected, or a combination of them is also preferable. Enzyme-processed gelatin described in Bull. Soc. Sci. Photo. Japan, No. 16, page 30 (1966), may also be used, and a hydrolyzate or enzymolyzate of gelatin can also be used. For the preparation of tabular grains, it is preferable to use a low-molecular-weight gelatin described in JP-A-1-158426.

In the case of adopting a system for conducting heat-development with the supply of a very small amount of water, water can be promptly absorbed by using the above-mentioned highly-water-absorbable polymer. In the case that the highly-water-absorbable polymer is used in the dye fixation layer or a protective layer thereof, it is possible to prevent the dye from being re-transferred from the dye fixation element to some other element after transfer.

In the present invention, the application amount of the binder is preferably 20 g or less, more preferably 10 g or less, and further preferably 7–0.5 g per $m^2$.

In the present invention, an organometal salt as an oxidizer may be used together with the light-sensitive silver halide emulsion. Among such organometal salts, an organosilver salt is particularly preferably used.

In the case of a heat-developable photographic material, an organosilver salt oxidizing agent may be used together with a photosensitive silver halide emulsion. As organic compounds capable of being used to form the oxidizing agent, there are benzotriazoles described in U.S. Pat. No. 4,500,626, columns 52 to 53, aliphatic acids, and other compounds. An acetylene silver described in U.S. Pat. No. 4,775,613 is also useful. It is possible to use the organosilver salts in the form of a combination of two or more.

These organosilver salts are used in an amount of generally 0.01 to 10 mol, and preferably 0.01 to 1 mol, per mol of the photosensitive silver halide. The total coating amount of the photosensitive silver halide emulsion and the organosilver salt is generally 0.05 to 10 g/$m^2$, and preferably 0.1 to 4 g/$m^2$, in terms of silver.

Preferably, the silver halide emulsion for use in the present invention is washed with water for desalting and is dispersed in a freshly prepared protective colloid. The temperature at which the washing with water is carried out can be selected in accordance with the purpose, and preferably the temperature is selected in the range of 5 to 20° C. The pH at which the washing is carried out can be selected in accordance with the purpose, and preferably the pH is selected in the range of 2 to 10, and more preferably in the range of 3 to 8. The pAg at which the washing is carried out can be selected in accordance with the purpose, and preferably the pAg is selected in the range of 5 to 10. As a method of washing with water, one can be selected from the noodle washing method, the dialysis method using a diaphragm, the centrifugation method, the coagulation settling method, and the ion exchange method. In the case of the coagulation settling method, selection can be made from, for example, the method wherein sulfuric acid salt is used, the method wherein an organic solvent is used, the method wherein a water-soluble polymer is used, and the method wherein a gelatin derivative is used. Further, the sedimentation method, in which inorganic salts composed of polyvalent anions (e.g. sodium sulfate), an anionic surfactant, an anionic polymer (e.g. polystyrenesulfonic acid sodium salt), or a gelatin derivative (e.g. an aliphatic-acylated gelatin, an aromatic-acylated gelatin, and an aromatic-carbamoylated gelatin) is employed, can be used, with the sedimentation method preferred.

The light-sensitive silver halide emulsion is generally a chemically-sensitized silver halide emulsion. To chemically sensitize the light-sensitive silver halide emulsion for use in the present invention, for example, a chalcogen sensitization method, such as a sulfur sensitization method, a selenium sensitization method, and a tellurium sensitization method; a noble metal sensitization method, wherein gold, platinum, or palladium is used; and a reduction sensitization method, each of which is known for silver halide emulsions in light-sensitive material, can be used alone or in combination (e.g. JP-A-3-110555 and JP-A-5-241267). These chemical sensitizations can be carried out in the presence of a nitrogen-containing heterocyclic compound (JP-A-62-253159). Further, the below-mentioned antifoggant can be added after the completion of the chemical sensitization. Specifically, methods described in JP-A-5-45833 and JP-A-62-40446 can be used.

At the time of the chemical sensitization, the pH is preferably 5.3 to 10.5, and more preferably 5.5 to 8.5, and the pAg is preferably 6.0 to 10.5, and more preferably 6.8 to 9.0.

The coating amount of the light-sensitive silver halide emulsion used in the present invention is generally in the range of 1 mg to 10 g/m in terms of silver, and preferably in the range of 10 mg to 10 g/$m^2$.

When the emulsion according to the present invention is prepared, in accordance with the purpose, it is preferable to allow a salt of a metal ion to be present, for example, at the time when grains are formed, in the step of desalting, at the time when the chemical sensitization is carried out, or before the application. When the grains are doped, the addition is preferably carried out at the time when the grains are formed; or after the formation of the grains, when the surface of the grains is modified or when the salt of a metal ion is used as a chemical sensitizer; or before the completion of the chemical sensitization. As to the doping of grains, selection can be made from a case in which the whole grains are doped, one in which only the core parts of the grains are doped, one in which only the shell parts of the grains are doped, one in which only the epitaxial parts of the grains are doped, and one in which only the substrate grains are doped. For example, Mg, Ca, Sr, Ba, Al, Sc, Y, La, Cr, Mn, Fe, Co, Ni, Cu, Zn, Ga, Ru, Rh, Pd, Re, Os, Ir, Pt, Au, Cd, Hg, Tl, In, Sn, Pb, and Bi can be used. These metals can be added if they are in the form of a salt that is soluble at the time when grains are formed, such as an ammonium salt, an acetate, a nitrate, a sulfate, a phosphate, a hydroxide, a six-coordinate complex, and a four-coordinate complex. Examples include $CdBr_2$, $CdCl_2$, $Cd(NO_3)_2$, $Pd(NO_3)_2$, $Pb(CH_3COO)_2$, $K_3[Fe(CN)_6]$, $(NH_4)_4[Fe(CN)_6]$, $K_3IrCl_6$, $(NH_4)_3RhCl_6$, and $K_4Ru(CN)_6$. As a ligand of the coordination compound, one can be selected from halo, aquo, cyano, cyanate, thiocyanate, nitrosyl, thionitrosyl, oxo, and carbonyl. With respect to these metal compounds, only one can be used, but two or more can also be used in combination.

In some cases, a method wherein a chalcogen compound is added during the preparation of the emulsion, as described in U.S. Pat. No. 3,772,031, is also useful. In addition to S, Se, and Te, a cyanate, a thiocyanate, a selenocyanate, a carbonate, a phosphate, or an acetate may be present.

The silver halide grains according to the present invention can be subjected to at least one of sulfur sensitization, selenium sensitization, tellurium sensitization (these three are called chalcogen sensitization, collectively), noble metal sensitization, and reduction sensitization, in any step of the production for the silver halide emulsion. A combination of two or more sensitizations is preferable. Various types of emulsions can be produced, depending on the steps in which the chemical sensitization is carried out. There are a type wherein chemical sensitizing nuclei are embedded in grains, a type wherein chemical sensitizing nuclei are embedded at parts near the surface of grains, and a type wherein chemical sensitizing nuclei are formed on the surface. In the emulsion according to the present invention, the location at which chemical sensitizing nuclei are situated can be selected in accordance with the purpose, and generally preferably at least one type of chemical sensitizing nucleus is formed near the surface.

Chemical sensitizations that can be carried out preferably in the present invention are chalcogen sensitization and noble metal sensitization, which may be used singly or in combination; and the chemical sensitization can be carried out by using active gelatin as described by T. H. James in "The Photographic Process," 4th edition, Macmillan, 1997, pages 67 to 76, or by using sulfur, selenium, tellurium, gold, platinum, palladium, or iridium, or a combination of these sensitizing agents, at a pAg of 5 to 10, a pH of 5 to 8, and a temperature of 30 to 80° C., as described in Research Disclosure, Item 12008 (April 1974); Research Disclosure, Item 13452 (June 1975); Research Disclosure, Item 307105 (November 1989); U.S. Pat. Nos. 2,642,361, 3,297,446, 3,772,031, 3,857,711, 3,901,714, 4,266,018, and 3,904,415, and British Patent No. 1 315 755.

In the sulfur sensitization, an unstable sulfur compound is used, and specifically, thiosulfates (e.g. hypo), thioureas (e.g. diphenylthiourea, triethylthiourea, and allylthiourea), rhodanines, mercaptos, thioamides, thiohydantoins, 4-oxooxazolidin-2-thions, di- or poly-sulfides, polythionic acids, and elemental sulfur, and known sulfur-containing compounds described in U.S. Pat. Nos. 3,857,711, 4,266,018, and 4,054,457, can be used. In many cases, sulfur sensitization is used in combination with noble metal sensitization.

A preferable amount of a sulfur sensitizing agent used for the silver halide grains according to the present invention is $1\times10^{-7}$ to $1\times10^{-3}$ mol, and more preferably $5\times10^{-7}$ to $1\times10^{-4}$ mol, per mol of the silver halide.

In the selenium sensitization, known unstable selenium compounds are used, such as those described, for example, in U.S. Pat. Nos. 3,297,446 and 3,297,447, specific such selenium compounds are colloidal metal selenium, selenoureas (e.g. N,N-dimethylselenourea and tetramethylselenourea), selenoketones (e.g. selenoacetone), selenoamides (e.g. selenoacetamide), selenocarboxylic acids and esters, isoselenocyanates, selenides (e.g. diethylselenides and triphenylphosphine selenide), and selenophosphates (e.g. tri-p-tolylselenophosphate). In some cases, preferably the selenium sensitization is used in combination with one or both of sulfur sensitization and noble metal sensitization.

The amount of the selenium sensitizing agent to be used varies depending on the selenium compound, the silver halide grains, the chemical ripening conditions, and the like that are used, and the amount is generally of the order of $10^{-8}$ to $10^{-4}$ mol, and preferably $10^{-7}$ to $10^{-5}$ mol, per mol of the silver halide.

As the tellurium sensitizing agent used in the present invention, compounds described in Canadian Patent No. 800 958, British Patent Nos. 1 295 462 and 1 396 696, JP-A-4-204640 and JP-A-4-333043 can be used, and specific tellurium sensitizing agents include colloidal tellurium, telluroureas (e.g. tetramethyltellurourea, N-carboxylethyl-N',N'-dimethyltellurourea, and N,N'-dimethylethylenetellurourea), isotellurocyanates, telluroketones, telluroamides, tellurohydrazides, telluroesters, phosphine tellurides (e.g. tributylphosphine telluride and butylisopropylphosphine telluride), and other tellurium compounds (e.g. potassium tellurocyanate and sodium telluropentathionate).

The amount of the tellurium sensitizing agent to be used is of the order of generally $10^{-7}$ to $5\times10^{-2}$ mol, and preferably $5\times10^{-7}$ to $10^{-3}$ mol, per mol of the silver halide.

In the noble metal sensitization, a salt of a noble metal, such as platinum, gold, palladium, and iridium, can be used, and specifically gold sensitization, palladium sensitization, and a combination thereof are particularly preferable. In the case of gold sensitization, a known compound, such as chloroauric acid, potassium chloroaurate, potassium auriothiocyanate, gold sulfide, and gold selenide, can be used. The palladium compound means a salt of divalent or tetravalent palladium salt. A preferable palladium compound is represented by $R^{11}{}_2PdX^3{}_6$ or $R^{11}{}_2PdX^3{}_4$, wherein $R^{11}$ represents a hydrogen atom, an alkali metal atom, or an ammonium group; and $X^3$ represents a halogen atom, i.e. a chlorine atom, a bromine atom, or an iodine atom.

Specifically, $K_2PdCl_4$, $(NH_4)_2PdCl_6$, $NaPdCl_4$, $(NH_4)_2PdCl_4$, $Li_2PdCl_4$, $Na_2PdCl_6$, or $K_2PdBr_4$ is preferable. Preferably a gold compound and a palladium compound are used in combination with a thiocyanate or a selenocyanate.

Preferably the emulsion according to the present invention is used in combination with gold sensitization. A preferable amount of the gold sensitizing agent is $1\times10^{-7}$ to $1\times10^{-3}$ mol, and more preferably $5\times10^{-7}$ to $5\times10^{-4}$ mol, per mol of the silver halide. A preferable amount of the palladium compound is in the range of $5\times10^{-7}$ to $1\times10^{-3}$ mol. A preferable amount of the thiocyan compound and the selenocyan compound is in the range of $1\times10^{-6}$ to $5\times10^{-2}$ mol.

Preferably that the silver halide emulsion according to the present invention is subjected to reduction sensitization during the formation of the grains, after the formation of the grains but before the chemical sensitization, or during or after the chemical sensitization.

Herein, the reduction sensitization can be selected from a method wherein a reduction sensitizer is added to a silver halide emulsion; a method called silver ripening, wherein the growth or ripening is made in an atmosphere having a pAg as low as 1 to 7; and a method called high-pH ripening, wherein the growth or ripening is made in an atmosphere having a pH as high as 8 to 11. Two or more methods can also be used in combination.

The method wherein a reduction sensitizer is added is preferable, because the level of reduction sensitization can be adjusted subtly.

As the reduction sensitizer, known reduction sensitizers can be selected and used, such as stannous salts, ascorbic acid and its derivatives, amines and polyamines, hydrazine and its derivatives, formamidinesufinic acid, silane compounds, and boran compounds; and two or more compounds can be used in combination. As the reduction sensitizer, preferable compounds are stannous chloride, aminoiminomethanesulfinic acid (popularly called thiourea dioxide), dimethylamineboran, and ascorbic acid and its derivatives. Since the amount of the reduction sensitizer to be added depends on the conditions of the production of the emulsion, the amount must be selected, but preferably it is in the range of $10^{-7}$ to $10^{-3}$ mol per mol of the silver halide.

The chemical sensitization can be carried out in the presence of a so-called chemical sensitization auxiliary. As a useful chemical sensitization auxiliary, a compound is used that is known to suppress fogging and to increase the sensitivity in the process of chemical sensitization, such as azaindene, azapyridazine, and azapyrimidine. Examples of chemical sensitization auxiliary improvers are described in U.S. Pat. Nos. 2,131,038, 3,411,914, and 3,554,757, JP-A-58-126526, and by G. F. Duffin in "Photographic Emulsion Chemistry" mentioned above, pages 138 to 143.

Preferably, an oxidizing agent for silver is added during the process of the production of the emulsion according to the present invention. The oxidizing agent for silver refers to a compound that acts on metal silver to convert it to silver ions. Particularly useful is a compound that converts quite fine silver grains, which are concomitantly produced during the formation of silver halide grains and during the chemical sensitization, to silver ions. The thus produced silver ions may form a silver salt that is hardly soluble in water, such as a silver halide, silver sulfide, and silver selenide, or they may form a silver salt that is readily soluble in water, such as silver nitrate. The oxidizing agent for silver may be inorganic or organic. Example inorganic oxidizing agents include ozone, hydrogen peroxide and its adducts (e.g. $NaBO_2$, $H_2O_2.H_2O$, $2NaCO_3.H_2O_2$, $Na_4P_2O_7.H_2O_2$, and $2NaSO_4.H_2O_2.2H_2O$); oxygen acid salts, such as peroxyacid salts (e.g. $K_2S_2O_8$, $K_2C_2O_6$, and $K_2P_2O_8$), peroxycomplex compounds (e.g. $K_2[Ti(O_2)C_2O_4].3H_2O$, $4K_2SO_4.Ti(O_2)OH.SO_4.2H_2O$, and $Na_3[VO(O_2)(C_2O_4)_2].6H_2O$), permanganates (e.g. $KMnO_4$), and chromates (e.g. $K_2CrO_7$); halogen elements, such as iodine and bromine; perhalates (e.g. potassium periodate), salts of metals having higher valences (e.g. potassium hexacyanoferrate(III), and thiosulfonates.

Examples of the organic oxidizing agents include quinones, such as p-quinone; organic peroxides, such as peracetic acid and perbenzoic acid; and compounds that can release active halogen (e.g. N-bromosuccinimido, chloramine T, and chloramine B).

Preferable oxidizing agents used in the present invention are such inorganic oxidizing agents as ozone, hydrogen peroxide and its adducts, halogen elements, and thiosulfonates, and such organic oxidizing agents as quinones. Use of a combination of the above reduction sensitization with the oxidizing agent for silver is a preferable mode. Use is made of one selected from a method wherein after an oxidizing agent is used, reduction sensitization is carried out; a method wherein after reduction sensitization is carried out, an oxidizing agent is used; and a method wherein an oxidizing agent and a reduction sensitizer are present simultaneously. These methods can be used in the step of forming grains or in the step of chemical sensitization, which step will be chosen.

In the photographic emulsion used in the present invention, various compounds can be incorporated for the purpose of preventing fogging during the process of the production of the photographic material, during the storage of the photographic material, or during the photographic processing, or for the purpose of stabilizing the photographic performance. That is, various compounds known as antifoggants or stabilizers can be added, such as thiazoles including benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (particularly 1-phenyl-5-mercaptotetrazole), mercaptopyrimidine, mercaptotriazine; thioketo compounds, such as oxazolinthione; and azaindenes, such as triazaindenes; tetraazaindenes (particularly 4-hydroxy-6-methyl-1,3,3a,7-tetraazaindenes), and pentaazaindenes. For examples, those described in U.S. Pat. Nos. 3,954,474 and 3,982,947, and JP-B-62-28660, can be used. A preferable compound is a compound described in JP-A-63-212932. In accordance with the purpose, the antifoggant and the stabilizer can be added at various times, for example, before the formation of the grains, during the formation of the grains, after the formation of the grains, in the step of washing with water, at the time of dispersion after the washing with water, before the chemical sensitization, during the chemical sensitization, after the chemical sensitization, and before the application. In addition to the case wherein the antifoggant and the stabilizer are added during the preparation of the emulsion, so that the antifogging effect and the stabilizing effect, which are their essential effects, may be achieved, they can be used for various other purposes, for example, for controlling the habit of the crystals of the grains, for making the grain size small, for reducing the solubility of the-grains, for controlling the chemical sensitization, and for controlling the arrangement of the dyes.

When the photosensitive silver halide used in the present invention is made to have color sensitivities of green sensitivity, red sensitivity, and infrared sensitivity, the photosensitive silver halide emulsion is generally spectrally sensitized with methine dyes or the like. If required, the blue-sensitive emulsion may be spectrally sensitized in the blue region.

Dyes that can be used include a cyanine dye, a merocyanine dye, a composite cyanin dye, a composite merocyanine dye, a halopolar cyanine dye, a hemicyanine dye, a styryl dye, and a hemioxonol dye. Particularly useful dyes are those belonging to a cyanine dye, a merocyanine dye, and a composite merocyanine dye. In these dyes, any of nuclei generally used in cyanine dyes as basic heterocycle nuclei can be applied. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, and a pyridine nucleus; and a nucleus formed by fusing an cycloaliphatic hydrocarbon ring or an aromatic hydrocarbon ring to these nuclei, that is, 5- to 6-heterocycle nuclei, such as an indolenine nucleus, a benzindolenine nucleus, an indole nucleus, a benzoxazole nucleus, a naphthooxazole nucleus, a benzothiazole nucleus, a naphthothiazole nucleus, a benzoselenazole nucleus, a benzimidazole nucleus, a rhodanine nucleus, and a thiobarbituric acid nucleus, can be applied. These nuclei may be substituted on the carbon atom. Specifically, sensitizing dyes described, for example, in U.S. Pat. No. 4,617,257 and JP-A-59-180550, JP-A-64-13546, JP-A-5-45828, and JP-A-5-45834 can be mentioned.

In the merocyanine dye or the composite merocyanine dye, as a nucleus having a ketomethylene structure, a 5- to 6-membered heterocycle nucleus, such as a pyrazolin-5-one nucleus, a thiohydantoine nucleus, a 2-thiooxazolidin-2,4-dione nucleus, a thiazolidin-2,4-dione nucleus, a rhodanine nucleus, and a thiobarbituric acid nucleus, can be applied.

These dyes can be used singly or in combination, and a combination of these sensitizing dyes is often used, particularly for the purpose of adjusting the wavelength of the spectral sensitivity, and for the purpose of supersensitization. Typical examples thereof are described in U.S. Pat. Nos. 2,688,545, 3,397,060, 2,977,229, 3,522,052, 3,527,64, 3,617,293, 3,628,964, 3,672,989, 3,679,428, 3,703,377, 3,769,301, 3,814,609, 3,837,862, and 4,026,707, British Patent Nos. 1 344 218 and 1 507 803, JP-B-43-4936, JP-B-53-12375, JP-A-52-110618 and JP-A-52-109925.

Together with the sensitizing dye, a dye having no spectral sensitizing action itself, or a compound that does not substantially absorb visible light and that exhibits supersensitization, may be included in the emulsion (e.g. those described, for example, in U.S. Pat. No. 3,615,641 and JP-A-63-23145).

The time when these sensitizing dyes are added to the emulsion may be at any stage of the preparation of the emulsion that is known to be useful, for example, at chemical ripening, or before or after chemical ripening.

Most usually, the sensitizing dye is added at a time after the completion of chemical sensitization but before the application, but the sensitizing dye may be added at the same time as the addition of the chemical sensitizer, to carry out spectral sensitization and chemical sensitization simultaneously, as described in U.S. Pat. Nos. 3,628,969 and 4,225,666, or the sensitizing dye may be added before the chemical sensitization, as described in JP-A-58-113928. Further, the sensitizing dye may be added before the completion of the precipitation of the silver halide grains, to start the spectral sensitization. Further, the sensitizing dye may be added before or after the formation of nuclei of the silver halide grains, in accordance with U.S. Pat. Nos. 4,183,756 and 4,225,666, or it may be added in portions, such that part of the sensitizing dye is added before the chemical sensitization, and the rest is added after the chemical sensitization.

Further, these sensitizing dyes and supersensitizing dyes may be added in the form of a solution of an organic solvent, such as methanol, or in the form of a dispersion of gelatin or in the form of a solution of a surface-active agent.

Generally the amount of the sensitizing dye to be added is of the order of $4\times10^{-6}$ to $8\times10^{-3}$ mol per mol of the silver halide, but when the silver halide grain size is 0.2 to 1.2 $\mu$m, which is more preferable, the amount of the sensitizing dye to be added is more effectively about $5\times10^{-5}$ to $2\times10^{-3}$ mol per mol of the silver halide.

As the reducing agent that can be used in the present invention, a reducing agent known in the field of heat-developable light-sensitive material may be used. The known reducing agent may be a dye-providing compound having a reducing ability, which will be described later. In this case, some other reducing agent may also be used at the same time. A reducing agent precursor, which exhibits no reducing ability by itself, but exhibits reducing ability by the action of a nucleophilic agent or heat during the step of development may be used.

Examples of the reducing agent or the precursor thereof for use in the present invention include those described in U.S. Pat. No. 4,500,626, col. 49–50, No. 4,839,272, No. 4,330,617, No. 4,590,152, No. 5,017,454 and No. 5,139,919, JP-A-60-140335, pages (17)–(18), JP-A-57-40245, JP-A-56-138736, JP-A-59-178458, JP-A-59-53831, JP-A-59-182449, JP-A-59-182450, JP-A-60-119555, JP-A-60-128436, JP-A-60-128439, JP-A-60-198540, JP-A-60-181742, JP-A-61-259253, JP-A-62-201434, JP-A-62-244044, JP-A-62-131253, JP-A-62-131256, JP-A-63-10151, JP-A-64-13546, pages (40)–(57), JP-A-1-120553, JP-A-2-32338, JP-A-2-35451, JP-A-2-234158 and JP-A-3-160443, and EP Patent No. 220,746, pages 78–96.

Combinations of various reducing agents can also be used, as disclosed in U.S. Pat. No. 3,039,869.

In the case that a reducing agent having nondiffusibility is used, a combination of an electron-transferring agent and/or an electron-transferring agent precursor with the nondiffusion reducing agent may be optionally used, to accelerate electron-movement between the nondiffusion reducing agent and silver halide that is developable. It is particularly preferred to use the electron-transferring agent or the precursor described in the U.S. Pat. No. 5,139,919, EP-A-418,743, JP-A-1-138556 and JP-A-3-102345. It is preferred to use a method of introducing the agent or the precursor stably into a given layer, as described in JP-A-2-230143 and JP-A-2-235044.

The electron-transferring agent or the precursor thereof can be selected among the above-mentioned reducing agents or the precursors thereof. The electron-transferring agent or the precursor thereof preferably has a larger mobility than the nondiffusion reducing agent (electron-providing material). A particularly useful electron-transferring agent is any one of 1-phenyl-3-pyrazolidones and aminophenols.

The nondiffusion reducing agent (electron-donating material), which is combined with the electron-transferring agent so as to be used, may be any one of the above-mentioned reducing agents which do not move substantially in layers of the light-sensitive material. Preferred examples thereof include hydroquinones; sulfoneamidephenols; sulfoneamidenaphthols; compounds described as electron donating materials in JP-A-53-110827, U.S. Pat. No. 5,032,487, No. 5,026,634 and No. 4,839,272; and dye-providing compounds having nondiffusibility and reducing ability, which will be described later.

It is also preferred to use an electron-providing material precursor as described in JP-A-3-160443.

The above-mentioned reducing agent can be used in the intermediate layer and the protective layer for various purposes, such as prevention of color mixture, improvement in color reproduction and whiteness, prevention of silver-transfer to the dye fixation material. Specifically, it is preferred to use a reducing agent described in EP-A-524,649 and 357,040, JP-A-4-249245, JP-A-2-64633, JP-A-2-46450 and JP-A-63-186240. It is also possible to use a development restrainer releasing, reducible compound as described in JP-B-3-63733, JP-A-1-150135, JP-A-2-110557, JP-A-2-64634 and JP-A-3-43735, and EP-A-451,833.

In the present invention, the total addition amount of the reducing agent is generally 0.01–20 moles and particularly preferably 0.1–10 moles per mole of silver.

To the photographic material related to the present technique, may be added the above-mentioned various additives, and also other various additives in accordance with the purpose.

These additives and conventionally known additives for photography that can be used in dye-fixing materials and heat-developable light-sensitive materials of the present invention, are described in more detail in Research Disclosure, Item 17643 (December 1978); Research Disclosure, Item 18176 (November 1979); and Research Disclosure, Item 307105 (November 1989), and the particular parts are given below in a table.

| Additive | RD 17643 | RD 18716 | RD 307105 |
|---|---|---|---|
| 1 Chemical sensitizers | p. 23 | p. 648 (right column) | p. 996 |
| 2 Sensitivity-enhancing agents | — | p. 648 (right column) | — |
| 3 Spectral sensitizers and Supersensitizers | pp. 23–24 | pp. 648 (right column)-649 (right column) | pp. 996–998 |
| 4 Brightening agents | p. 24 | pp. 647 (right column | p. 998 |
| 5 Light absorbers, Filter dyes, and UV Absorbers | pp. 25–26 | pp. 649 (right column)-650 (left column) | p. 1003 |
| 6 Binders | p. 26 | p. 651 | pp. 1003–1004 |
| 7 Plasticizers and Lubricants | p. 27 | p. 650 | p. 1006 |
| 8 Coating aids and Surfactants | pp. 26–27 | p. 650 | pp. 1005 (left)-1006 (right) |
| 9 Antistatic agents | p. 27 | p. 650 (right column) | pp. 1006–1007 |
| 10 Antifogging agents and Stabilizers | pp. 24–25 | p. 649 | pp. 998–1000 |
| 11 Anti-staining agents | p. 25 (right column) | p. 650 (left to right) | |
| 12 Image-dye stabilizers | p. 25 | p. 650 (left column) | p. 872 |
| 13 Hardeners | p. 26 | p. 651 (left column) | pp. 1004 (right)-1005 (left) |
| 14 Matt agent | — | — | pp. 878–879 |

In addition to the above hardeners, other hardeners described, for example, in U.S. Pat. No. 4,678,739, 41st column; U.S. Pat. No. 4,791,042, and JP-A-59-116655, JP-A-62-245261, JP-A-61-18942, and JP-A-4-218044, can be mentioned. More specifically, aldehyde hardeners (e.g. formaldehyde), aziridine hardeners, epoxy hardeners, vinyl sulfone hardeners (e.g. N,N'-ethylene-bis (vinylsulfonylacetamide)ethane), N-methylol hardeners (e.g. dimethylol urea), or polymer hardeners (e.g. compounds described, for example, in JP-A-62-234157) can be mentioned.

These hardeners are used in an amount of generally 0.001 to 1 g, and preferably 0.005 to 0.5 g, per g of the coated gelatin. The layer into which the hardener(s) is added may be any of layers that constitute the photographic material (another name, a photographic element) or the dye-fixing material (another name, a dye-fixing element or an image-receiving element), or the hardener may be divided into two or more parts, which are added into two or more layers.

In the dye-fixing material and the photographic material of the present invention, a matting agent can be used for the purpose of adhesion prevention, improvement of slipping property, matting, and the like. Example matting agents icnclude silicon dioxide, polyolefins, polymethacrylates, and the like described in JP-A-61-88256, page (29), as well as compounds, including benzoguanamine resin beads, polycarbonate resin beads, ABS resin beads, and the like, described in JP-A-63-274944 and JP-A-63-274952. Other matting agents described in the above RDs can be used. These matting agents are added into the uppermost layer (protective layer), and also into a lower layer if required.

Further, the constitutional layers of a heat-developable photographic material and dye-fixing material may contain a heat solvent, an antifoaming agent, an anti-bacterial agent, a mildew-proofing agent, colloidal silica, and the like. Specific examples of these additives are described, for example, in JP-A-61-88256, pages (26) to (32); JP-A-3-11338, and JP-B-2-51496.

In the constitutional layers of the dye-fixing material and the photographic material of the present invention, use can be made of various surface-active agents for various purposes of, for example, serving as a coating aid, improving releasability and slipping property, preventing electrification (static), or accelerating development. Specific examples of the surface-active agents are described, for example, in the above Research Disclosures and JP-A-62-173463 and JP-A-62-183457. In the case of a heat-developable photographic material and a dye-fixing material, also preferably an organofluoro-compound is contained in the constitutional layer, for example, for the purposes of improving slipping properties, preventing electrification, and improving releasability. Typical examples of the organofluoro compound are hydrophobic fluorine-containing compounds, including solid fluoro compound resins, such as ethylene tetrafluoride resins; oily fluoro compounds, including fluoro oils; or fluorine-containing surface-active agents described, for example, in JP-B-57-9053, 8th column to the 17th column, and JP-A-61-20944 and JP-A-62-135836.

In the photographic material of the present invention, known antifading agents can be used. Example organic antifading agents include hydroquinones, 5-hydroxychromans, 5-hydroxycoumarans, paraalkoxyphenols, hindered phenols, including bisphenols; gallic acid derivatives, methylenedioxybenzenes, aminophenols, hindered amines, and ether or ester derivatives produced by silylating or alkylating the phenolic hydroxyl group of these compounds. Further, metal complexes, represented by (bissalicylaldoximato)nickel complex and (bis-N,N-dialyldithiocarbamato)nickel complex, can also be used.

To prevent a yellow dye image from being deteriorated by heat, humidity, and light, the addition of a compound having both the structures of a hindered amine and a hindered phenol in the same molecule, as described in U.S. Pat. No. 4,268,593, gives a good result. Further, to prevent a magenta dye image from being deteriorated particularly by light, spiroindanes described in JP-A-56-159644, and chromans substituted with a hydroquinone diether or monoether, described in JP-A-55-89835, give a good result.

In the constitutional layers of the dye-fixing material and the photographic material of the present invention, various antifoggants or photographic stabilizers and their precursors can be used. Specific examples thereof include compounds described, for example, in the above-mentioned Research Disclosures, U.S. Pat. Nos. 5,089,378, 4,500,627, and 4,614, 702, JP-A-64-13546 (pages (7) to (9), (57) to (71), and (81) to (97)), U.S. Pat. Nos. 4,775,610, 4,626,500, and 4,983,494, JP-A-62-174747, JP-A-62-239148, JP-A-63-264747, JP-A-1-150135, JP-A-2-110557, and JP-A-2-178650, and Research Disclosure No. 17 643 (1978), pages (24) to (25).

These compounds are preferably used in an amount of $5\times10^{-6}$ to $1\times10^{-1}$ mol, and more preferably $1\times10^{-5}\times1\times10^{-2}$ mol, per mol of silver.

Suitable support (base) that can be used in the present invention include a synthetic plastic film, for example, made of polyolefins, such as polyethylene and polypropylene, polycarbonates, cellulose acetates, polyethylene terephthalates, polyethylene naphthalates, and polyvinyl chlorides; a paper support, for example, made of photographic raw paper, printing paper, baryta paper, and resin-coated paper; a support formed by providing the above plastic film with a reflective layer; and a support described in JP-A-62-253159, pages 29 to 31.

Those described in the above Research Disclosure No. 17643, page 28; Research Disclosure No. 18716, page 647, right column, to page 648, left column; and Research Disclosure No. 307105, page 879, are also preferably used. These supports may be subjected to heat treatment at or below Tg, as described in U.S. Pat. No. 4,141,735, so that they may be hardly core-set. The surface of the support may be surface-treated, to improve the adhesion between the support and the emulsion undercoat layer. In the present invention, the surface treatment can be carried out by glow discharge treatment, ultraviolet-ray-irradiation treatment, corona treatment, or flame treatment.

Further, supports described in Kochi Gijutsu No. 5 (published by Azutekku Yugen-kaisha, Mar. 22, 1991), pages 44 to 149, can also be used.

Transparent supports made, for example, of polyethylenenaphthalene dicarboxylates, and supports produced by coating these transparent supports with a transparent magnetic substance, can also be used.

In a heat-developable photographic material, in order to obtain a constant image all the time against changes in the processing temperature and the processing time at the time of development, various development inhibitors can be used. Herein, the term "a development inhibitor" means a compound that neutralizes bases quickly or reacts quickly with bases after suitable development, to lower the base concentration in the film, to stop the development; or a compound that interacts with silver and silver salts, to inhibit the development. Specific examples include acid precursors that release an acid when heated, electrophilic compounds that undergo a substitution reaction with coexisting bases when heated; and nitrogen-containing heterocyclic compounds, mercapto compounds, and their precursors. Details are described in JP-A-62-253159, pages (31) to (32).

When the photographic material of the present invention is used as a heat-developable photographic material, to supply a base, a method wherein a base is generated from a base precursor, is preferable.

Preferable base precursors that can be used in the present invention include a salt of a base with an organic acid that is decarboxylated when heated; a compound that is decomposed by such a reaction as an intramolecular nucleophilic substitution reaction, Lossen rearrangement, or Beckmann rearrangement, to release amines; a compound that undergoes some reaction when heated, to release a base; and a compound that undergoes hydrolysis or a complex formation reaction, to generate a base. Examples of the above base precursor that generates a base when heated include salts of trichloroacetic acid described, for example, in British Patent No. 998 959; salts of α-sulfonylacetic acid that are further improved in stability, as described in U.S. Pat. No. 4,060, 420; salts of propiolic acid described in JP-A-59-180537; 2-carboxycarboamide derivatives described in U.S. Pat. No. 4,088,496; salts of heat-decomposable acids that are formed using, in addition to an organic base, an alkali metal or an alkali earth metal as a base component (JP-A-59-195237); hydroxamcarbamates that use Lossen rearrangement, as described in JP-A-59-168440; and aldoximecarbamates that produce nitrile when heated, as described in JP-A-59-157637.

Also useful are base precursors described, for example, in British Patent Nos. 998 945 and 2 079 480, JP-A-50-226225, U.S. Pat. Nos. 3,220,846, 4,514,493, and 4,657,848, and Kochi Gijutsu No. 5 (published by Azutekku Yugen-kaisha, Mar. 22, 1991), pages 55 to 86.

Examples of the method of exposing the photographic material of the present invention with light and recording the image, include a method wherein a landscape, a man, or the like is directly photographed by a camera or the like; a method wherein a reversal film or a negative film is exposed to light using, for example, a printer, or an enlarging apparatus; a method wherein an original picture is subjected to scanning exposure through a slit by using an exposure system of a copying machine or the like; a method wherein light-emitting diodes and various lasers (e.g. laser diodes and gas lasers) are allowed to emit light, to carry out scanning exposure through image information and electrical signals (methods described, for example, in JP-A-2-129625, JP-A-5-176144, JP-A-5-199372, and JP-A-6-127021); and a method wherein image information is outputted to an image display device, such as a CRT, a liquid crystal display, an electroluminescence display, and a plasma display, and exposure is carried out directly or through an optical system.

Light sources that can be used for recording an image on the photographic material, as mentioned above, include natural light and light sources and exposure methods described in U.S. Pat. No. 4,500,626, 56th column, and JP-A-2-53378 and JP-A-2-54672, such as a tungsten lamp, a light-emitting diode, a laser light source, and a CRT light source.

Image-wise exposure can be carried out by using a wavelength-converting element that uses a nonlinear optical material and a coherent light source, such as laser rays, in combination. Herein the term "nonlinear optical material" refers to a material that can develop nonlinearity of the electric field and the polarization that appears when subjected to a strong photoelectric field, such as laser rays, and inorganic compounds, represented by lithium niobate, potassium dihydrogenphosphate (KDP), lithium iodate, and $BaB_2O_4$; urea derivatives, nitroaniline derivatives, nitropyridine-N-oxide derivatives, such as 3-methyl-4-nitropyridine-N-oxide (POM); and compounds described in JP-A-61-53462 and JP-A-62-210432 can be preferably used. As the form of the wavelength-converting element, for example, a single crystal optical waveguide type and a fiber type are known, both of which are useful.

The above image information can employ, for example, image signals obtained from video cameras, electronic still cameras, and the like; television signals, represented by Nippon Television Singo Kikaku (NTSC); image signals obtained by dividing an original picture into a number of picture elements by a scanner or the like; and an image produced by a computer, represented by CG or CAD.

The color-developing agent of the present invention can be used for all silver halide photographic materials, including color negatives, color papers, X-ray photographic materials and photomechanical reproduction materials for color instant photography and color reversal, and X-ray photographic materials and reproduction photographic materials for forming color images. Further, the color-developing agent of the present invention can be added into a silver halide photographic material, and also into a processing solution. The color-developing agent of the present invention can be preferably contained in at least one hydrophilic colloid layer provided on a support, when it is used in a silver halide light-sensitive material. As a silver halide light-sensitive material containing the color-developing agent of the present invention, a color diffusion transfer silver halide photographic light-sensitive material is preferable.

When the color-developing agent of the present invention is added into a silver halide photographic material, the development can be carried out by heating treatment or activator treatment.

The heating treatment of photographic materials is known in the art, and heat-developable photographic materials and the process thereof are described, for example, in "Shashin Kogaku no Kiso" (published by Coronasha, 1979), pages 553 to 555; "Eizo Joho" (published on April 1978), page 40; "Nebletts Handbook of Photography and Reprography," 7th edition (Van Nostrand and Reinhold Company), pages 32 to 33; U.S. Pat. Nos. 3,152,904, 3,301,678, 3,392,020, and 3,457,075, British Patent Nos. 1 131 108 and 1 167 777, and Research Disclosure (June 1978), pages 9 to 15 (RD-17029).

The activator treatment refers to a treatment wherein a color-developing agent is built in a photographic material and the photographic material is subjected to development with a processing solution free from any color-developing agent. In this case, the processing solution is characterized in that it does not contain any color-developing agent, which is usually contained as a development processing solution component, but the processing solution may contain other components (e.g. an alkali and an auxiliary developing agent). Examples of the activator treatment are shown in known publications, such as European Patent Nos. 545 491(A1) and 565 165(A1).

In the present invention, the term "a developing solution" means a processing solution containing a color-developing agent or a processing solution not containing a developing agent (for activator).

The processing temperature of the developing solution to be applied to the present invention is generally 20 to 50° C., and preferably 30 to 45° C. The processing time is generally 5 sec to 2 min, and preferably 10 sec to 1 min. With respect to the replenishing rate, although a small amount is preferable, the replenishing rate is generally 15 to 600 ml, preferably 25 to 200 ml, and more preferably 35 to 100 ml, per $m^2$ of the photographic material to be processed.

The photographic material of the present invention may be in a form having an electro-conductive heat-generating element layer, which serves as a heating means for heat processing. In this case, as the heat-generating element, those described, for example, in JP-A-61-145544 can be employed.

The heating temperature in the heat development step is generally about 65 to 180° C., preferably 70 to 180° C., more preferably 75 to 180° C., further more preferably 80 to 150° C., and particularly preferably 80 to 135° C. The heating time is preferably 0.1 to 120 sec, more preferably 0.1 to 60 sec, and particularly preferably 0.1 to 30 sec.

Example heating methods in the development step and/or transferring step include one wherein the photographic material is brought in contact with a heated block or plate; a method wherein the photographic material is brought in contact with a hot plate, a hot presser, a hot roller, a hot drum, a halogen lamp heater, an infrared lamp heater, or a far-infrared lamp heater; and a method wherein the photographic material is passed through a high-temperature atmosphere. As a method wherein the heat-developable photographic material and a dye-fixing material are placed one upon the other, methods described in JP-A-62-253159 and JP-A-61-147244, on page (27) can be applied.

After the development, a desilvering process can be carried out. The desilvering process comprises a fixing process, or both bleaching process and a fixing process. When both bleaching and fixing are carried out, the bleaching process and the fixing process may be carried out separately or simultaneously (bleach-fixing process). Also, according to the purpose, the processing may be carried out in a bleach-fixing bath having two successive tanks; or the fixing process may be carried out before the bleach-fixing process; or the bleach-fixing may be carried out after the bleach-fixing process. As the processing solutions to be used in bleaching/fixing, use can be made of those usually used.

In some cases, it is preferable to carry out the stabilizing process, to stabilize silver salts and dye images, without carrying out the desilvering process, after the development.

A combination of the color-developing agent of the present invention and a coupler with a known dye-providing compound, such as a dye developing agent or a compound capable of releasing a diffusible dye by redox reaction explained later, may be used in the same photographical element. For example, it is possible to use a method in which an image in yellow and an image in cyan can be formed by the color-developing agent of the present invention and a coupler and an image in magenta can be formed by another dye image-forming compound.

An example of the dye image-forming compound that may be simultaneously used in the present invention is a combination of a known developing agent with a coupler capable of reacting with this agent. The manner of using this coupler is a manner in which an oxidized product of the developing agent, which is produced by redox reaction of a silver salt with the developing agent, reacts with the coupler, to form a dye, which manner is described in many literatures. This coupler may be a four-equivalent coupler or a two-equivalent coupler. Preferred is also a two-equivalnt coupler which has a nondiffusible group as a split-off group and generates a diffusible dye by reaction with the oxidized product of the developing agent. Specific examples of the developing agent and the coupler are described in detail, for example, in "The Theory of the Photographic Process" (4th edition, by T. H. James, Macmillian, 1977), on pages 291–334 and pages 354–361, and in JP-A-58-123533, JP-A-58-149046, JP-A-58-149047, JP-A-59-111148, JP-A-59-124399, JP-A-59-174835, JP-A-59-231539, JP-A-59-231540, JP-A-60-2950, JP-A-60-2951, JP-A-60-14242, JP-A-60-23474, and JP-A-60-66249.

In addition, as dye-image-forming compounds, for example, dye silver compounds formed by combining an organosilver salt with a dye can be mentioned. Specific examples of the dye silver compound are described in, for example, Research Disclosure, May, 1978, pages 54 to 58 (RD-16966).

Further, azo dyes used in the heat-developable silver dye bleach process can be mentioned as another example of the dye-image-forming compound. Specific examples of azo dyes and bleaching methods are described in, for example, U.S. Pat. No. 4,235,957 and Research Disclosure, April, 1976, pages 30 to 32 (RD-14433). In addition, leuco dyes described in, for example, U.S. Pat. No. 3,985,565 and U.S. Pat. No. 4,022,617 can be mentioned as another example of the dye-providing substance. As the azo dye, the azo dye represented by the formula (2-1) itself and the dye-forming compound represented by the formula (2-5) of the second embodiment of the present invention can be also preferably used.

Further, as another example of the dye-image forming compound, compounds having a function of releasing or diffusing a diffusion dye imagewise can be mentioned.

The compounds of this type can be represented by the following formula (LI):

$$(Dye^1\text{-}X^2)_n\text{—}Y^1 \qquad \text{(LI)}$$

Wherein $Dye^1$ represents a group to give a known dye, a group to give a dye whose wavelength is temporarily shortened, or a group to give a dye precursor; $X^2$ represents a single bond or a linking group; $Y^1$ represents a group which has such a property that produces a difference in diffusibility of the compound represented by $(Dye^1\text{-}X^2)_n$—$Y^1$ correspondingly or inversely-correspondingly to the light-sensitive silver salt having a latent image imagewise, or that releases $Dye^1$, to produce a difference in diffusibility between $Dye^1$ released and $(Dye^1\text{-}X^2)_n$—$Y^1$; n is 1 or 2, and when n is 2, two $Dye^1\text{-}X^2$'s may be the same or different.

As specific examples of the dye-providing substance represented by the formula (LI), dye developers in which a hydroquinon-series developer is combined with a dye component, are described in U.S. Pat. No. 3,134,764, No. 3,362,819, No. 3,597,200, No. 3,544,545 and No. 3,482,972. Also, substances releasing a diffusible dye by an intermolecular nucleophilic substitution reaction are described in JP-A-51-63618, and substances releasing a diffusible dye by an intermolecular rollback reaction of isoxazolone ring are described in JP-A-49-111628. In all of these methods, a diffusible dye is released or diffused in undeveloped portions, but neither released nor diffused in developed portions.

A further method has been proposed, in which a dye-releasing compound is made to be an oxidized product type incapable of releasing a dye and to coexist together with a reducing agent or its precursor, and after being subjected to development, the dye-releasing compound is reduced by the reducing agent left non-oxidized, to thereby release a diffusible dye. Specific examples of the dye image-forming compound used in this method are described in JP-A-53-110,827, JP-A-54-130,927, JP-A-56-164,342 and JP-A-53-35,533.

As substances releasing a dye in developed portions, substances releasing a diffusible dye by a reaction between a coupler having a diffusible dye in a split-off group and an oxidized product of a developing agent, are described in U.K. Patent No. 1,330,524, JP-B-48-39,165 and U.S. Pat. No. 3,443,940.

In the system using these color-developing agents, image contamination with oxidation-decomposed products of the developing agent causes a serious problem. A dye-releasing compound which needs no developing agent and the compound itself has reducibility, has been proposed to solve the problem. Typical examples of the dye-releasing compound include dye image-forming compounds described in U.S. Pat. No. 3,928,312, No. 4,053,312, No. 4,055,428 and No. 4,336,322, JP-A-59-65839, JP-A-59-69839, JP-A-51-104,343, Journal of Research & Disclosure No. 17465, U.S. Pat. No. 3,725,062, No. 3,728,113 and No. 3,443,939, JP-A-58-116537, JP-A-57-179840 and U.S. Pat. No. 4,500,626.

To form an color image in the present invention, it is possible to use a compound which releases, when silver ions are reduced to silver atoms under a high temperature condition, a diffusible dye corresponding to this reaction, that is, dye-providing compound.

Examples of the dye-providing compound include compounds having a function of releasing a diffusible dye imagewise. Compounds of this type can be represented by the following formula (LI-1):

$$((Dye^2)m\text{-}Y^2)n^1\text{-}Z^{31} \qquad \text{(LI-1)}$$

wherein Dye represents a group to give a dye or a dye precursor, or a group to give a dye whose absorption region is temporarily changed to a short wave or a precursor thereof; $Y^2$ represents a single bond or a connecting group; $Z^{31}$ represents a group which has a nature of generating a difference in diffusibility of the compound represented by the $((Dye^2)m\text{-}Y^2)n^1\text{-}Z^{31}$ in correspondence to a light-sensitive silver salt having a latent image imagewise, or a nature of releasing $(Dye^2)m\text{-}Y^2$ and generating a difference in diffusibility between released $(Dye^2)m\text{-}Y^2$ and the $((Dye^2)m\text{-}Y^2)n^1\text{-}Z^{31}$; m is an integer of 1-5, $n^1$ is 1 or 2, and when either of m or $n^1$ is not 1, $Dye^2$'s may be the same or different. More specifically, the compounds of this type are the following compounds ① and ③.

① A compound which exhibits non-diffusibility by itself and which is a coupler having a diffusible dye as a split-off group and releasing the diffusible dye by reaction with an oxidized product of a reducing agent (DDR coupler). Specific examples thereof are described in, for example, G.B. Patent No. 1,330,524, JP-B-48-39165, U.S. Pat. No. 3,443,940, No. 4,474,867 and No. 4,483,914.

② A compound which exhibits non-diffusibility by itself and which has ability to reduce a silver halide or an organosilver salt and releases a diffusible dye at the time of reducing the opponent (DRR compound). Typical examples thereof are described in U.S. Pat. No. 3,928,312, No. 4,053,312, No. 4,055,428 and No. 4,336,322, JP-A-56-65839, JP-A-59-69839, JP-A-53-3819 and JP-A-51-104343, RD No. 17,465, U.S. Pat. No. 3,725,062, No. 3,728,113 and No. 3,443,939, JP-A-58-116537 and JP-A-57-179840, and U.S. Pat. No. 4,500,626. Specific examples of the DRR compound include compounds described in the above-mentioned U.S. Pat. No. 4,500,626, col. 22–44. Compounds (1)–(3), (10)–(13), (16)–(19), (28)–(30), (33)–(35), (38)–(40) and (42)–(64) in this U.S. Patent are particularly preferred. Compounds described in U.S. Pat. No. 4,639,408, col. 37–39 are also useful. As dye-providing compounds other than the above-mentioned couplers and the compounds of the formula (LI-1), the following may be used: dye silver compounds wherein an organosilver salt is combined with a dye (e.g. Research Disclosure, May 1978, pages 54–58), azo dyes used in heat-development silver dye bleach process (e.g. U.S. Pat. No. 4,235,957, Research Disclosure, April 1976, pages 30–32), and leuco dyes (e.g. U.S. Pat. No. 3,985,565, No. 4,022,617).

As other dye-forming methods applicable to the present invention, there are known methods of producing a diffusible dye by coupling reaction of an incorporated-type developing agent with a coupler, as described in JP-A-8-286340, JP-A-10-142764 and JP-A-10-254111. In the present invention, it is particularly preferred to use a dye-forming method by such a coupling, or to use a dye-forming method by a DRR compound. As the incorporated-type developing agent, the color-developing agent represented by the formula (1-1) of the first embodiment of the present invention can also be preferably used.

The color diffusion transfer method is described hereafter.

In the system forming an image by diffusion transfer of a dye by using the light-sensitive material of the present invention, the light-sensitive materials are generally divided into two types: one mode in which a light-sensitive element and an image-receiving element (dye-fixing element) are formed separately by application on two supports (these may be referred to a light-sensitive material and dye-fixing material, respectively), and the other mode in which both of the elements are formed by application on the same support.

The mutual relations of the light-sensitive element to the dye-fixing element, to the supports and to a white reflecting layer, which are described in the specification of JP-A-61-147244, pp58–59 and U.S. Pat. No. 4,500,626, 57th column, may be applied to the light-sensitive material of the present invention.

A typical mode of film unit in which a light-sensitive element and an image receiving element are formed on the same support, is one in which the image-receiving element and the light-sensitive element are laminated on one transparent support and which eliminates the necessity of peeling the light-sensitive element from the image-receiving element after a transferred image is completed. To state in more detail, the image-receiving element comprises at least one mordant layer (also called to as an image-receiving layer or a dye-fixing layer). Also, the light-sensitive element, in preferred embodiments, comprises a combination of a blue-sensitive emulsion layer, a green-sensitive emulsion layer and a red-sensitive emulsion layer, a combination of a green-sensitive emulsion layer, a red-sensitive emulsion layer and an infrared-light-sensitive emulsion layer, or a combination of a blue-sensitive emulsion layer, a red-sensitive emulsion layer and an infrared-light-sensitive emulsion layer. Moreover, a yellow dye image-forming compound (a dye image-forming compound containing the color-developing agent of the present invention and a coupler; also referred to as a dye-providing substance), a magenta dye image-forming compound (a dye image-forming compound containing the color-developing agent of the present invention and a coupler), and a cyan dye image-forming compound (a dye image-forming compound containing the color-developing agent of the present invention and a coupler) are respectively combined with the above emulsion layers. Thus, the above mode of image-forming system according to the present invention is structured. (Here, the "infrared-light-sensitive emulsion layer" means an emulsion layer possessing sensitivity to light of 700 nm or more and especially 740 nm or more). Each of these light-sensitive emulsion layers may be divided into two or more layers as required. In addition, a white reflecting layer containing a solid dye, e.g., titanium oxide, may be formed between the mordant layer and the light-sensitive layer or the layer containing the dye image-forming compound (the dye image-forming compound containing the color-developing agent of the present invention and a coupler), so as to appreciate the transferred image through the transparent support.

A shading layer may be further provided between the white reflecting layer and the light-sensitive layer so as to allow development processing completed under light. Also, as desired, a peelable layer may be formed at a proper position to peel all or a part of the light-sensitive element from the image-receiving element (embodiments like this are described, for example, in JP-A-56-67840 and Canadian Patent No. 674,082).

Another form of a lamination type which requires peeling, is a color diffusion transfer photographic film unit disclosed in JP-A-63-226649. That is, the color diffusion transfer photographic film unit comprises: a light-sensitive element having (a) a layer having a neutralizing function, (b) a dye receiving layer, (c) an peeling layer, and (d) at least one silver halide emulsion layer combined with a dye image forming substance, successively, in this order, on a white support; an alkaline processing composition containing a light-shielding agent; and a transparent cover sheet, and further comprises a layer having light-shielding function on the side opposite to the side of the emulsion layer on which the processing composition is applied (expanded).

In another mode which does not need peeling, the light-sensitive element is formed by application on one transparent support, a white reflecting layer is formed by application on the light-sensitive element, and an image-receiving layer is further laminated on the white reflecting layer. The mode in which an image-receiving element, a white reflecting layer, a peelable layer and a light-sensitive element are laminated on the same support, and the light-sensitive element is intentionally peeled from the image-receiving element, is described in U.S. Pat. No. 3,730,718.

On the other hand, the typical modes in which the light-sensitive element and the image-receiving element are separately formed by application on two supports are generally divided into two categories: one is a peelable type and the other is a peeling-needless type. To mention these types in detail, in a preferred embodiment of the peelable film unit, a light-reflecting layer is provided on the back-surface of a support and at least one image-receiving layer is formed by application on the surface of the support. Also, the light-sensitive element is formed by application on a support provided with a shading layer. This embodiment is devised such that the surface of the side applied the light-sensitive layer does not face the surface of the side applied the mordant layer until the exposure is finished, but the surface of the side applied the light-sensitive layer is overturned so that it faces and overlaps the surface of the side applied the mordant layer after the exposure was finished (for example, during development processing). The light-sensitive element is peeled from the image-receiving element immediately after the transferred image is completed in the mordant layer.

In a preferred embodiment of the peeling-needless film unit, at least one mordant layer is formed on a transparent support, and a light-sensitive element is formed by application on a support transparent or provided with a shading layer, and the surface of the side applied the light-sensitive layer and the surface of the side applied the mordant layer are facing and are overlapped on each other.

The aforementioned modes may be applied to both of a system of development using an alkaline processing solution which is developed (expanded) on a light-sensitive material, and a heat development system. Particularly, in the former system, a container (processing or treating element) which contains the alkaline processing solution and can be burst by pressure, may be combined. Among these systems, in the peeling-needless film unit in which an image-receiving element and a light-sensitive element are laminated on one support, the processing element is preferably disposed between the light-sensitive element and a cover sheet which is overlapped on the light-sensitive element. Also, in the mode in which a light-sensitive element and an image-receiving element are separately formed by application on two supports, the processing element is preferably disposed between the light-sensitive element and the image-receiving element during the developing time at the latest. Preferably the processing element contains a shading agent (e.g., carbon black and dyes which are changed in color depending upon pH) and/or a white pigment (e.g. titanium oxide) according to the mode of film unit. In a film unit of the type which carries out development using the alkaline processing solution, preferably a neutralization-timing mechanism composed of a combination of a neutralization layer and a neutralization timing layer is incorporated into the cover sheet, the image-receiving element or the light-sensitive element.

As the mordant used in the aforementioned image-receiving element or the dye-fixing element explained later, a polymer mordant is preferable. Here, the polymer mordant includes, for example, polymers containing a tertiary amino group, polymers containing a nitrogen-containing heterocyclic moiety, and polymers containing a quaternary cationic group.

Specific examples of these polymer mordants are described in JP-A-61-147244, pp98–100 and U.S. Pat. No. 4,500,626, 57th–60th columns.

The following will describe the image-receiving element for the color diffusion transfer method in more detail. This image-receiving element in color diffusion transfer method preferably comprises at least one layer containing a mordant (a mordanting layer). As the mordant, any one of mordants known in the field of photography may be used. Specific examples thereof are described in G.B. Patents No. 2,011,912, No. 2,056,101 and 2,093,041, U.S. Pat. No. 4,115,124, No. 4,273,853 and 4,282,305, JP-A-59-232340, JP-A-60-118834, JP-A-60-128443, JP-A-60-122940, JP-A-60-122921 and JP-A-60-235134.

Various other additives may be appropriately used in the image-receiving element for the color diffusion transfer method. These will be described in the item of a dye fixation element (image-receiving element) for the color diffusion transfer method for heat-development.

The following will describe light-sensitive elements for the color diffusion transfer method. The contents described in the right lower column, line 8 on page (17) of JP-A-2-32335 to the right lower column, line 19 on page (20) thereof can be applied to a silver halide emulsion, a spectral sensitizing dye, an emulsion layer, a multilayer structures for full colors, a processing composition, a film unit for the color diffusion transfer method, and its constituting layers, which are used in the color diffusion transfer method.

The light-sensitive element used in the present invention may comprise, as required, various additives which are known as materials used in a heat-developable light-sensitive element, and layers other than the light-sensitive layer, such as a protective layer, intermediate layer, antistatic layer, antihalation layer, peelable layer which makes peeling from a dye-fixing element easy, and a matted layer. These various additives include plasticizers, matt agents, sharpness-improving dyes, antihalation dyes, surfactants, fluorescent brighteners, antislip agents, antioxidizing agents, anti-fading agents, and diffusible dye-trapping agent, which are described in Journal of Research & Disclosure, the June issue, pp9–15 (1978) and JP-A-61-88256.

Especially the protective layer is generally made to contain organic or inorganic matt agents to prevent adhesion. This protective layer may also include a mordant and a UV-ray absorber. The protective layer and the intermediate layer may be respectively structured of two or more layers.

Also, the intermediate layer may include a reducing agent, a UV-ray absorber and a white pigment, e.g., titanium dioxide, to prevent color-fading and color mixing. The white pigment may be added not only to the intermediate layer but also to the emulsion layer, to improve the sensitivity.

The dye-fixing element may be provided with an auxiliary layer(s), such as a protective layer, peelable layer and curling-preventive layer, as required. Particularly it is useful to provide the protective layer. One or more of the aforementioned layers may include hydrophilic heat solvents, plasticizers, anti-fading agents, UV-ray absorbers, anti-slip agents, matt agents, antioxidizing agents, dispersed vinyl compounds for increasing dimentional stability, surfactants, luminescent whiteners, and the like. Further, particularly, in the system wherein heat development and diffusion transfer of a dye are carried out simultaneously in the presence of a small amount of water, a base and/or base precursor, which is described later, is preferably contained in the dye-fixing element, with a viewpoint of increasing the preservability of the light-sensitive element. Specific examples of these additives are described in JP-A-61-88256, pages 101 to 120.

A peeling layer for the color diffusion transfer method will be described. The peeling layer used in the present invention can be provided on an arbitrary position of a light-sensitive sheet inside the unit after processing. Examples of the material of the peeling layer that can be used include those described in for example, JP-A-47-8237, JP-A-59-220727, JP-A-49-4653, JP-A-49-4334, JP-A-50-65133 and JP-A-45-24075, U.S. Pat. Nos. 3,220,835, 4,359,518, 3,227,550, 2,759,825, 4,401,746 and 4,366,227. Specifically, a water-soluble (or alkali-soluble) cellulose derivative may be used. Examples thereof include hydroxyethylcellulose, cellulose acetate phthalate, elasticized methylcellulose, ethylcellulose, cellulose nitride, and carboxymethylcellulose. The following may be used: various natural polymers, such as alginic acid, pectin and Arabian gum; various modified gelatins, such as acetylated gelatin and phthalated gelatin; polyvinyl alcohol; polyacrylate; polymethyl methacrylate; and copolymers thereof. Among these compounds, a cellulose derivative is preferred and hydroxyethylcellulose is particularly preferred as the material for peeling.

Besides the water-soluble cellulose derivative, a particulate substance of an organic polymer or the like may be used as the material for peeling. Examples of the organic polymer which can be used in the present invention include polymer latexes made, for example, of polyethylene, polystyrene, polymethyl methacrylate, polyvinyl pyrrolidone and butyl acrylate, each of which has an average particle size of 0.01–10 $\mu$m. It is preferred to use a light-reflective hollow polymer latex composed of a material whose inside contains air and whose outside is made of an organic polymer, as will be described below. This light-reflective hollow polymer latex may be synthesized by the method described in JP-A-61-151646.

In the light-sensitive element and/or the dye-fixing element according to the present invention, an image-forming accelerator may be used. The image-forming accelerator has an ability to accelerate a redox reaction between a silver salt oxidizing agent and a reducing agent, an ability to accelerate reactions to form a dye from the dye image-forming compound (dye-providing substance) containing the coupler and the color-developing agent of the present invention, to decompose the dye or to release a diffusible dye, and an ability to accelerate the transfer of the dye from the structural layer of the light-sensitive element to the dye-fixing layer. From the physicochemical abilities, the image-forming accelerators are classified into bases or base precursors, nucleophilic compounds, high boiling point organic solvents (oils), heat solvents, surfactants, compounds which interact with silver or silver ions, and the like. It is to be noted that these material groups usually have duplex abilities and possess some of the above accelerating effects in general. The details of these materials are described in JP-A-61-93451, pp67–71.

There are various methods for the production of a base. Compounds used in these methods are all useful as a base precursor.

The base precursor is, for example, a salt of a base and an organic acid which is decarboxylated by heat, or a compound which releases an amine by intermolecular nucleophile substitution reaction, Lossen rearrangement or Beckman rearrangement. Specific examples thereof are described in U.S. Pat. No. 4,514,493, No. 4,657,848, and the like.

In the system for performing heat development and transfer of a dye simultaneously in the presence of a small amount of water, the method of incorporating the base and/or the base precursor into the dye fixation material is preferred for making the stability of the heat-developable light-sensitive material high.

In addition to the above, there are, for example, a method described in E.P. Patent No. 0210660A2 and U.S. Pat. No. 4,740,445, in which a base is generated by mixing a metal compound (e.g., a metal salt), which is sparingly soluble in water, with a compound (a complex-forming compound or complexing agent) which can react with the metal ion constituting the metal compound, which is sparingly soluble in water, to form a complex; and a method described in JP-A-61-232451 in which a base is generated by electrolysis. Especially, the former method is effective.

Given as examples of the metal compound which is sparingly soluble in water include carbonates, hydroxides or oxides of zinc, aluminum, calcium or barium. The complex-forming compounds are explained in detail, for example, in "Critical Stability Constants" written jointly by "A. E. Martell, R. M. Smith, Vol No. 4 and Vol. No. 5, Plenum Press. Specific examples include salts of aminocarboxylic acids, iminodiacetic acids, pyridinecarboxylic acids, aminophosphoric acids, carboxylic acids (mono-, di-, tri-, tetracarboxylic acids and compounds having any of substituents, e.g., a phosphono, hydroxy, oxo, ester, amide, alkoxy, mercapto, alkylthio or phosphino group), hydroxam acids, polyacrylates or polyphosphoric acids and alkali metals, guanidines, amidines or quaternary ammonium salts.

It is advantageous to add these metal compound which is sparing soluble in water and complex-forming compound to each of the light-sensitive element and dye-fixing element.

In the light-sensitive element and/or the dye-fixing element for use in the present invention, in order to obtain a constant image all the time, against fluctuation of the processing temperature and the processing time at the time of development, various development-stopping agents can be used.

Herein, the term "a development-stopping agent" means a compound that neutralizes bases quickly or reacts quickly with bases after proper development, to lower the base concentration in the film, to stop the development; or a compound that interacts with silver and silver salts, to inhibit the development. Specific examples include acid precursors that release an acid when heated, electrophilic compounds that undergo a substitution reaction with coexisting bases when heated, nitrogen-containing heterocyclic compounds, mercapto compounds, and their precursors (for example, compounds described in JP-A-60-108837, JP-A-60-192939, JP-A-60-230133, JP-A-60-230134, and JP-A-62-253159, pages (31)–(32)).

Also, compounds which release a mercapto compound by heating are also useful. These compounds are described in, for example, JP-A-61-67851, JP-A-61-147244, JP-A-61-124941, JP-A-61-185743, JP-A-61-182039, JP-A-61-185744, JP-A-61-184539, JP-A-61-188540 and JP-A-61-53632.

As the binder of light-sensitive element and/or dye-fixing element of the present invention, a hydrophilic binder can be used. Typically, the hydrophilic binder is a transparent or semitranparent hydrophilic binder. Specifically, examples include natural compounds such as proteins including gelatin, gelatin derivatives and the like, or polysaccharides including cellulose derivatives, starches, gum-arabic, dextrans, and the like; and synthetic polymer compounds such as water soluble polyvinyl compounds including polyvinyl pyrrolidones, and acrylamide polymers. A disperse vinyl compound which is used in the form of a latex and increase the dimentional stability of photographic materials may also be used. These binders may be used either singly or in combinations.

It is preferable that the amount of the binder to be applied in the present invention is 20 g or less, more preferably 10 g or less and further preferably 7 g or less per 1 $M^2$.

A ratio of a high-boiling point organic solvent, which is dispersed in the binder together with hydrophobic compounds such as the color-developing agent of the present invention and the coupler, to the binder is as follows: the amount of the solvent is generally 1 ml or less, preferably 0.5 ml or less and more preferably 0.3 ml or less, per g of the binder.

The structural layer (e.g., a photographic emulsion layer and a dye-fixing layer) of the dye-fixing element and/or the light-sensitive element of the present invention may contain an inorganic or organic hardener.

Specific examples of the hardener include those described in the specification of JP-A-61-147244, pp94–95 and in the specification of JP-A-59-157636, pp38. These compounds may be used either singly or in combination.

To accelerate the dye transfer, a hydrophilic heat solvent that is solid at normal temperatures and melts at a higher temperature can be built in the light-sensitive element and/or the dye-fixing element. The hydrophilic heat solvent can be built in any of the light-sensitive element and the dye-fixing element, and it may be built in both elements. Further, the layer wherein the hydrophilic heat solvent is built in may be any of the light-sensitive silevr halide emulsion layer, the intermediate layer, the protective layer, and the dye-fixing layer, but preferably it is built-in the dye-fixing layer and/or the layer adjacent thereto. Examples of the hydrophilic heat solvent include ureas, pyridines, amides, sulfonamides, imides, alcohols, oximes, and other heterocyclic compounds. Further, to accelerate the dye transfer, high-boiling organic solvent can be contained in a light-sensitive element and/or dye-fixing element.

The support to be used in the light-sensitive element and/or the dye-fixing element of the present invention can stand against treating temperature. As a usual support, glasses, papers, polymer films, metals or similar materials may be used and also those described as supports in the specification of JP-A-61-147244, pp95–96 may be used.

The support is generally a support for photography, such as paper described in "Basis of Photographic Engineering—Silver Salt Photography Version—", pages (223)–(224), edited by the Society of Photographic Society and Technology of Japan, and published by Corona Publishing Co., Ltd. (1979), or a synthetic polymer (film). Specific examples thereof include polyethylene terephthalate, polyethylene naphthalate, polycarbonate, polyvinyl chloride, polystyrene, polypropylene, polyimide, and cellulose (for example, triacetylcellulose) films, films wherein a pigment such as titanium oxide is incorporated into any one of these films, synthetic paper made from polypropylene, mixed paper made from synthetic resin pulp such as polyethylene and natural pulp, Yankee paper, baryta paper, coated paper (particularly, cast-coated paper), metal, cloth, and glass.

These supports may be used alone, or may be used as a support wherein one surface or two surfaces of any one of these supports is laminated with synthetic polymer such as polyethylene. If necessary, a pigment or a dye such as titanium oxide, ultramarine blue or carbon black may be incorporated into the laminating layer.

Besides, it is possible to use supports described in JP-A-62-253159, pages (29)–(31), JP-A-1-161236, pages (14)–(17), JP-A-63-316848, JP-A-2-22651 and JP-A-3-56955, U.S. Pat. No. 5,001,033, and the like.

An antistatic agent including carbon black, a hydrophilic binder and a semi-conductive metal oxide such as alumina sol or tin oxide may be applied to the back surface of the above-mentioned support. Specifically, supports described in JP-A-63-220246 and the like may be used.

In order to improve adhesiveness between the surface of the support and the hydrophilic binder, it is preferred to subject the surface to various surface treatments or undercoating.

The light-sensitive material and/or the dye fixation material of the present invention may be in the form having an electrically conductive heating layer as heating means for heat development and dye-diffusion/transfer. As the heating element in this case, a heating element described in JP-A-61-145544 may be used.

A transparent or opaque exothermic element in this case may be made as a resistive exothermic body by making use of conventionally known techniques. As the method of producing the resistive exothermic body, there are a method which makes use of a thin film of an inorganic material exhibiting semiconductivity and a method which makes use of an organic thin film in which electroconductive fine grains are dispersed in a binder. As materials used in these methods, compounds described in the specification of JP-A-61-29835 may be used.

In the system for forming an image by diffusion transfer of a dye, various compounds may be added to layers constituting the heat-developable light-sensitive material of the present invention, in order to fix unnecessary dyes or colorants or make them colorless to improve the white background of resultant images.

Specifically, it is possible to use compounds described in EP-A-353,741 and EP-A-461,416, and JP-A-63-163345 and JP-A-62-203158.

Various pigments or dyes may be used in layers constituting the heat-developable light-sensitive material of the present invention to improve color differentiation property and sensitization.

Specifically, it is possible to use compounds described in the above-mentioned Research Disclosure or compounds and layer-structures described in EP-A-479,167 and EP-A-502,508, JP-A-1-167838, JP-A-4-343355, JP-A-2-168252 and JP-A-61-20943, and EP-A-479,167 and EP-A-502,508.

In the system for forming an image by diffusion transfer of a dye, a dye fixation material is used together with the heat-developable light-sensitive material. The dye fixation material may be in the form in which it is applied to a support different from a support to which the light-sensitive material is applied, or may be in the form in which it is applied to the same support to which the light-sensitive material is applied. With respect to the mutual relationship between the light-sensitive material and the dye fixation material, the relationship to the support, and the relationship to a white reflection layer, relationships described in U.S. Pat. No. 4,500,626, col. 57 can be applied to the present invention.

The dye fixation material which is preferably used in the present invention has at least one layer comprising a mordant and a binder. As the mordant, a mordant known in the photographic field can be used. Specific examples thereof include those described in U.S. Pat. No. 4,500,626, col. 58–59, JP-A-88256, pages (32)–(41), JP-A-1-161236, pages (4)–(7), and U.S. Pat. No. 4,774,162, No. 4,619,883 and No. 4,594,308. A dye acceptable polymer compound as described in U.S. Pat. No. 4,463,079 may be used.

The binder which is used in the dye fixation material of the present invention is preferably the above-mentioned hydrophilic binder. It is preferred to use this binder together with any one of carraghenane as described in EP-A-443,529 and latexes having a glass-transition temperature of 40° C. or less as described in JP-B-3-74820.

If necessary, auxiliary layers such as a protective layer, a peeling layer, an undercoat layer, an intermediate layer, a backing layer and a curl-inhibiting layer may be formed in the dye fixation material. The formation of the protective layer is particularly useful.

In layers constituting the heat-developable light-sensitive material and the dye fixation material, a plasticizer, a lubricant or a high boiling point organic solvent as an improver of capability of peeling of the light-sensitive material from the dye fixation material may be used. Specific examples thereof are described in the above-mentioned Research Disclosures, JP-A-62-245253, and the like.

For the above-mentioned purposes, various silicone oils (all silicone oils including dimethylsilicone oil and modified silicone oils in which various organic groups are introduced into dimethylsiloxane) may be used. Useful examples thereof include various modified silicone oils described in a technical material "Modified Silicone Oils" pages 6–18B, published by Shin-Etsu Chemical Co., Ltd. Carboxy-modified silicone (trade name: X-22-3710) and the like are particularly useful.

Silicone oils described in JP-A-62-215953 and JP-A-63-46449 are also useful.

A fading inhibitor (anti-fading agent) may be used in the heat-developable light-sensitive material or the dye fixation material. Examples of the fading inhibitor are an antioxidant, an ultraviolet absorber, and some kinds of metal complexes. Dye image stabilizers, ultraviolet absorbers and the like described in the above-mentioned Research Disclosures are also useful.

Examples of the antioxidant include chroman compounds, coumarane compounds, phenol compounds (for example, hindered phenols), hydroquinone derivatives, hindered amine derivatives, and spiroindane compounds. Compounds described in JP-A-61-159644 are also useful.

Examples of the ultraviolet absorber include benzotriazole compounds (for example, U.S. Pat. No. 3,533,794), 4-thiazolidone compounds (for example, U.S. Pat. No. 3,352,681), benzophenone compounds (for example, JP-A-46-2784), and compounds described in, for example, JP-A-54-48535, JP-A-62-136641 and JP-A-61-88256. An ultraviolet absorbing polymer described in JP-A-62-260152 is also useful.

Examples of the metal complexes include compounds described in U.S. Pat. No. 4,241,155, No. 4,245,018, col. 3–36, and No. 4,254,195, col. 3–8, JP-A-62-174741, JP-A-61-88256, pages (27)–(29), JP-A-63-199248, JP-A-1-75568 and JP-A-1-74272, and the like.

The fading inhibitor for preventing the color of the dye transferred to the dye fixation material from fading out may be beforehand contained in the dye fixation material, or it may be supplied from the outside, for example, from the heat-developable light-sensitive material or a transferring solvent, which will be described alter, to the dye fixation material.

Any combination of two or more selected from the antioxidants, the ultraviolet absorbers and the metal complexes may be used.

A fluorescent bleaching agent may be used in the heat-developable light-sensitive material or the dye fixation material. It is particularly preferred to incorporate the fluorescent bleaching agent into the dye fixation material or supply the agent from the outside, for example, from the heat-developable material or the transferring solvent. Examples thereof include compounds described in "The Chemistry of Synthetic Dyes", Vol. 5, Chapter 8, edited by K. Veenkataraman, and JP-A-61-143752. Specific examples thereof include stylbene compounds, coumarin compounds, biphenyl compounds, benzoxazolyl compounds, naphthalimide compounds, pyrazoline compounds, and carbostyryl compounds.

The fluorescent bleaching agent may be combined with the fading inhibitor or the ultraviolet absorber and the combination may be used. Specific examples of the fading inhibitor, the ultraviolet absorber, and the fluorescent bleaching agent are described in JP-A-62-215272, pages (125)–(137) and JP-A-1-161236, pages (17)–(43).

In the present invention, to apply a heat developing light-sensitive layer, protective layer, intermediate layer, undercoat layer, backing layer, dye-fixing layer and other layers, a method described in U.S. Pat. No. 4,500,626, 55th–56th columns can be used.

As a light source for image exposure used to record an image in the light-sensitive element, radiation rays including visible light may be used. In general, light sources used in usual color printing, for example, a tungsten lamp, mercury lamp, halogen lamps such as an iodine lamp, xenon lamp, laser light source, CRT light source or light emitting diode (LED), which are all described in JP-A-61-147244, p100 and U.S. Pat. No. 4,500,626, 56th column, may be used.

In the image-forming method involving a heating step to which the present invention is applied, for example, a heat developing step and a dye-transfer step are carried out either separately or simultaneously. Also, both steps may be successive in the meaning of the fact that a transfer operation is carried out in succession to a developing operation in one step.

For example, there are (1) a method in which an image is formed on the light-sensitive element by exposure, followed by heating, thereafter a dye-fixing element is overlapped on the light-sensitive element and, as required, heated to transfer a movable dye to the dye-fixing element, and (2) a method in which an image is formed on the light-sensitive element by exposure and a dye-fixing element is overlapped on the light-sensitive element, followed by heating. The aforementioned methods (1) and (2) may be applied either in substantially the absence of water or in the presence of minute water.

The development can be made at about 50° C. to about 250° C., but the heating temperature in the heat developing step is preferably 60° C. to 180° C., more preferably 70° C. to 180° C. and particularly preferably 75° C. to 150° C. In the case of heating in the presence of minute water, the upper limit of the heating temperature is below the boiling temperature. The step of diffusion transfer of a dye may be carried out simultaneously with heat development, or it may be carried out after the completion of the heat-development step. When the transfer step is performed after the heat developing step is finished, although the transfer can be made in a temperature range between the temperature in the heat developing step and room temperature, the heating temperature in the transfer step is more preferably 50° C. or higher, but equal to or lower than the temperature that is lower by 10° C. than the temperature in the heat developing step.

In a preferred image-forming method according to the present invention, an image is exposed or heating is performed in the presence of minute water and a base and/or a base precursor when an image is exposed, and a diffusible dye generated in the portions corresponding or reversely corresponding to a silver image at the same time of developing is transferred to the dye-fixing layer. This method ensures that the production and releasing reactions of the diffusible dye run very quickly, and hence the diffusible dye is transferred to the dye-fixing layer rapidly, thereby to obtain a high density color image in a short period of time.

The amount of water to be used in this embodiment can be as small as 0.1 times and preferably more than 0.1 times the weight of the total applied film of the light-sensitive element and dye-fixing layer, and equal to or less than the weight (specifically, equal to or less than the amount calculated by subtracting the weight of the total applied film from the weight of the solvent corresponding to the maximum swelled volume of the total applied film) of the solvent corresponding to the maximum swelled volume of the total applied film.

The state of the film during swelling is unstable and local bleeding is likely caused depending upon the conditions. In order to evade this phenomenon, the amount of water is preferably equal to or smaller than the amount corresponding to the volume of the total applied film of the light-sensitive element and dye-fixing element when the film reaches a maximum swelling. Concretely, the amount of water is preferably in a range between 1 and 50 g, more preferably 2 and 35 g and further preferably 3 and 25 g per total $m^2$ of the sum of the light-sensitive element and dye-fixing element.

A base and/or base precursor used in this embodiment may be incorporated into any of the light-sensitive element and the dye-fixing element. The base and/or base precursor may also be supplied after it is dissolved in water.

In the above embodiment, it is preferable that the image-forming reaction system be made to contain a metal compound (e.g., a basic metal compound which is sparingly soluble in water), which is sparingly soluble in water, as a base precursor, and a compound (a complexing agent) that can react with the metal ion constituting the metal compound, which is sparing soluble in water, by using water as a medium to form a complex; and an alkali be generated by the reaction of those two compounds during heating, to raise the pH of the system. Here, the image reaction system means the region where an image-forming reaction is caused. Given as specific example of the region are layers belonging to both of the light-sensitive element and dye-fixing element. In the case where two or more layers are present, the reaction system may be included in any of these layers.

It is necessary to add the metal compound that is sparingly soluble in water and the complex-forming compound to at least separate layers to prevent the both from reacting with each other by the time of development processing. For example, in a so-called monosheet material in which the light-sensitive element and the dye-fixing element are formed on the same support, it is preferable that both of the elements are incorporated into layers separately, and that one or more layers are interposed between these separate layers.

In a more preferred embodiment, the metal compound that is sparingly soluble in water and the complex-forming compound are respectively contained in each layer formed on separate supports. For example, it is preferable that the metal compound which is sparingly soluble in water be contained in the light-sensitive element and the complex-forming compound be contained in the dye-fixing element having a support different from that of the light-sensitive element. The complex-forming compound may be supplied after it is dissolved in water allowed to coexist. Preferably the metal compound which is sparingly soluble in water is contained in the form of a fine grain dispersion prepared according to the methods described in, for example, JP-A-56-17480 and JP-A-53-102733. Preferably the average grain size of the fine grain dispersion is 50 μm or less and particularly preferably 5 μm or less. The metal compound which is sparingly soluble in water may be added to any one of the light-sensitive layer, intermediate layer and protective layer of the light-sensitive element and may be added separately to two or more layers.

When the metal compound which is sparingly soluble in water or the complex-forming compound is to be contained in a layer on a support, the amount of the compound(s) to be added depends on the type of compound, the grain size of the metal compound which is insoluble in water and the rate of reaction for forming a complex. The metal compound or the complex-forming compound is used preferably in an amount of 50% by weight or less, and more preferably in an amount ranging from 0.01% by weight to 40% by weight, in term of weight of the coated film. When the complex-forming compound is supplied after it is dissolved in water, its concentration is in a range preferably from 0.005 mols to 5 mols and particularly preferably from 0.05 mols to 2 mols, per 1 liter of the solution. In the present invention, the content of the complex-forming compound in the reaction system is preferably 1/100 times to 100 times and particularly preferably 1/10 times to 20 times the content of the compound, which is sparingly soluble in water, in terms of molar ratio.

A method of supplying water to the light-sensitive layer or the dye-fixing layer includes, for example, one described in JP-A-61-147244, from p101, line 9 to p102, line 4.

As heating means in the developing step and/or transfer step, there are means described in JP-A-61-147244, from p102, line 14 to p103, line 11, for example, a heating plate, iron and heat roller. A method may be adopted in which layers of conductive materials such as graphite, carbon black and metals are overlapped on the light-sensitive element and/or dye-fixing element and current is allowed to flow through the conductive layer to heat directly.

As pressure conditions and a method of applying pressure when the light-sensitive element and the dye-fixing element are overlapped on each other and stuck to each other, a method described in JP-A-61-147244, pp103 to 104 may be used.

To process the photographic elements for use in the present invention, any of various heat development apparatuses can be used. For example, apparatuses described, for example, in JP-A-59-75247, JP-A-59-177547, JP-A-59-181353, and JP-A-60-18951, unexamined published Japanese Utility Model Application (JU-A) No. 62-25944 can be preferably used.

The transfer of a dye is caused only by heat. A solvent for accelerating the dye-transfer may be used. The solvent is described in U.S. Pat. No. 4,704,345 and No. 4,740,445, JP-A-61-238056 and the like. A method of carrying out heating in the presence of a small amount of a solvent (particularly, water) and then performing development and transfer simultaneously or continuously is also useful. In this method, the heating temperature is preferably from 50° C. to the boiling point of the solvent. When the solvent is, for example, water, the heating temperature is preferably 50–100° C.

Examples of the solvent used to accelerate development and/or diffuse and transfer a dye include water, aqueous basic solutions containing an inorganic alkali metal salt or an organic base (materials described in the item of the image-forming accelerator can be used as the base), low boiling point solvents, and mixed solutions of a low boiling solvent and water or the above-mentioned aqueous basic solution. It is possible to incorporate a surfactant, an antifoggant, a compound which is combined with a slightly soluble metal salt to form a complex, an antifungal agent, or an anti-bacterial agent, into the solvent.

The solvent used in the steps of heat development and diffusion/transfer is preferably water. The water may be any water which is generally used. Specific examples thereof include distilled water, city water, well water and mineral water. In a heat developing apparatus in which the heat-developable light-sensitive material and the dye fixation material of the present invention are used, water may be used in a batch form or circulating form. In the latter case, water containing components eluted from the material is used. Apparatuses and water described in JP-A-63-144354, JP-A-63-144355, JP-A-62-38460 and JP-A-3-210555 may be used.

The above-mentioned solvent may be supplied to the heat-developable light-sensitive material, the dye fixation material, or both of the two. The amount to be used thereof is equal to or less than the mass of the solvent corresponding to the maximum swelling volume of all of the applied films.

As the method of supplying water, for example, the method described in JP-A-62-253159, page (5) and JP-A-63-85544 is preferably used. The solvent may be confined in microcapsules, or may be beforehand incorporated, in the form of hydrate, into the heat-developable light-sensitive material, the dye fixation material, or both of the two.

The temperature of the supplied water may be 30–60° C. as described in the above-mentioned JP-A-63-85544. Particularly in order to prevent propagation of unwanted bacteria in water, it is useful to set the temperature to 45° C. or higher.

The dye of the present invention when used as an azo dye itself, may be used in ink-jet recording system.

The ink-jet recording system can be classified to a manner using oily ink, a manner using aqueous ink and a manner using solid ink (at room temperature). These manners are specifically described in JP-A-3-239175, JP-A-7-118584, and JP-A-7-70490.

The dye of the present invention is also useful as a thermally-transferring dye.

A thermally-transferring dye releasing material using the thermally-transferring dye may be used in the form of a sheet, a continuous roll or a ribbon. The dye of the present invention can be applied to the methods described in JP-B-4-15760 and JP-A-1-188391 and JP-A-3-83685.

By using the color-developing agent of the present invention, good color forming property can be obtained in a short time, and further a color developed image excellent in stability against light, heat, humidity and the like can be obtained.

According to the silver halide photographic light-sensitive material and image-forming method using the novel color-developing agent of the present invention, good developed color can be obtained at the time of development, and an image excellent in image quality and image-stability can be formed.

According to the azo dye and silver halide color photographic light-sensitive material of the present invention, an image having a good hue and a high developed color density can be obtained, and further stability thereof against light, heat, air, chemicals and the like is improved.

The azo dye of the present invention is preferable as a yellow dye or a magenta dye, it exhibits excellent absorption characteristics, and it is improved in stability against light, humidity, heat, air, chemicals and the like. The silver halide photographic light-sensitive material of the present invention that contains a dye-image-forming compound preferable as a yellow or magenta dye-image-forming compound, exhibits excellent absorption characteristics, and it is improved in stability against light, humidity, heat, air, chemicals and the like. The silver halide photographic light-sensitive material of the present invention that contains the azo dye, exhibits excellent absorption characteristics, and it is improved in stability against light, humidity, heat, air, chemicals and the like.

The present invention is described in more detail with reference to the following examples, but the present invention is not limited thereto.

EXAMPLES

Example 1-1

A dye fixation material R101 was formed by the following method.

On a surface of a support (thickness: 152 μm), the core material of which was made of pulp, a surface PE layer (thickness: 36.0 μm) and a surface undercoat layer (thickness: 0.1 μm) were successively formed in this order from the side of the support. On the back surface thereof, a back PE layer (thickness: 27.0 μm) and a back undercoat layer (thickness: 0.5 μm) were successively formed in this order from the side of the support. Components of the respective layers are shown in Table 1.

TABLE 1

Constitution of Support

| Name of layer | Composition | Film thickness (μm) |
|---|---|---|
| Surface undercoat layer | Gelatin | 0.1 |
| Surface PE layer (Glossy) | Low-density polyethylene (Density 0.923): 90.2 parts<br>Surface-processed titanium oxide: 9.8 parts<br>Ultramarine: 0.001 parts | 36.0 |
| Pulp layer | Fine quality paper (LBPK/NBSR = 6/4, Density 1.053) | 152 |
| Back-surface PE layer (Matt) | High-density polyethylene (Density 0.955) | 27 |
| Back-surface undercoat layer | Styrene/acrylate copolymer<br>Colloidal silica<br>Polystyrenesulfonic acid sodium salt | 0.1 |
| | | 215.2 |

Then, coating solutions for forming six (6) layers were applied by multilayer coating to the surface of the surface undercoat layer to form the six layers on the support. Thus, the dye fixation material R101 was formed. Constituting components of the respective layers are shown in Tables 2 and 3.

TABLE 2

Constitution of dye-fixing material R101

| Number of layer | Additive | Coated amount ($mg/m^2$) |
|---|---|---|
| Sixth layer | Water-soluble polymer (1) | 130 |
| | Water-soluble polymer (2) | 35 |
| | Water-soluble polymer (3) | 45 |
| | Potassium nitrate | 20 |
| | Anionic surfactant (1) | 6 |
| | Anionic surfactant (2) | 6 |
| | Amphoteric surfactant (1) | 50 |
| | Stain-preventing agent (1) | 7 |
| | Stain-preventing agent (2) | 12 |
| | Matting agent (1) | 7 |
| Fifth layer | Gelatin | 250 |
| | Water-soluble polymer (1) | 25 |
| | Anionic surfactant (3) | 9 |
| | Hardener (1) | 185 |
| Forth layer | Mordant (2) | 1850 |
| | Water-soluble polymer (2) | 260 |
| | Water-soluble polymer (4) | 1400 |
| | Dispersion of latex (1) | 600 |
| | Anionic surfactant (3) | 25 |
| | Nonionic surfactant (1) | 18 |
| | Citric acid | 15 |
| | Guanidine picolinate | 2550 |
| | Sodium quinolinate | 350 |
| Third layer | Gelatin | 370 |
| | Mordant (1) | 300 |
| | Anionic surfactant (3) | 12 |
| | Table 3 (continued from Table 2) | |
| Second layer | Gelatin | 700 |
| | Mordant (1) | 290 |
| | Water-soluble polymer (1) | 55 |
| | Water-soluble polymer (2) | 330 |
| | Anionic surfactant (3) | 30 |
| | Anionic surfactant (4) | 7 |
| | High-boiling organic solvent (1) | 700 |
| | Brightening agent (1) | 30 |
| | Stain-preventing agent (3) | 32 |
| | Guanidine picolinate | 360 |
| | Potassium quinolinate | 45 |
| First layer | Gelatin | 280 |
| | Water-soluble polymer (1) | 12 |
| | Anionic surfactant (1) | 14 |
| | Sodium metaborate | 35 |
| | Hardener (1) | 185 |

Base (1) Polyethylene-Laminated Paper Support (thickness 215 μm)
The coated amount of dispersion of latex is in terms of the coated amount of solid content of latex.

Anionic surfactant (1)

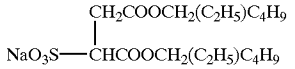

Anionic surfactant (2)

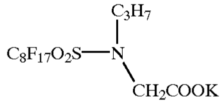

Anionic surfactant (3)

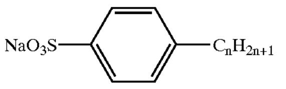

n = 12.6

-continued

Anionic surfactant (4)

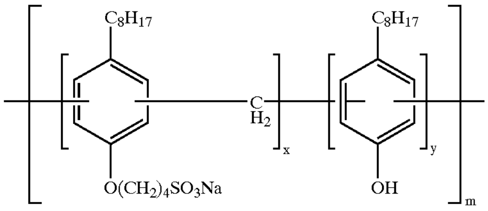

x:y = 4:6 m = 6.8

Nonionic surfactant (1)

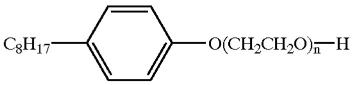

n = 85

Amphoteric surfactant (1)

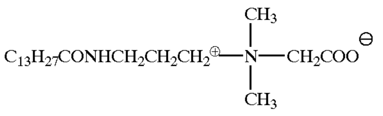

Brightening agent (1)

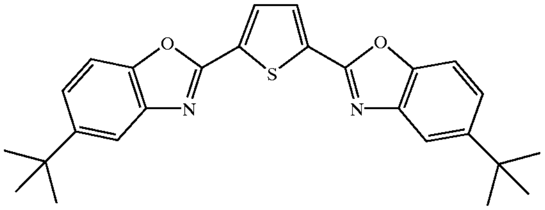

Mordant (1)

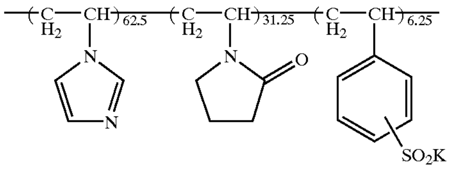

High-boiling organic solvent (1)

$C_{26}H_{46.9}Cl_{7.1}$ EMPARA 40 (trade name: manufactured by Ajinomoto K.K.)

Stain-preventing agent (1)

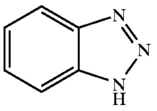

Stain-preventing agent (2)

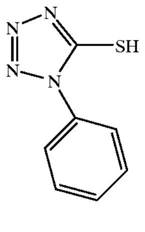

Stain-preventing agent (3)

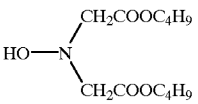

Water-soluble polymer (1)

Sumikagel L5-H (trade name: manufactured by Sumitomo Kagaku Co., Ltd.)

-continued

Water-soluble polymer (2)

Dextran (molecular weight 70,000)

Water-soluble polymer (3)

κ(kappa)-Carrageenan (trade name: manufactured by Taito Co.)

Water-soluble polymer (4)

MP Polymer MP-102 (trade name: manufactured by by Kuraray Co.

Dispersion of latex (1)

LX-438 (trade name: manufactured by Nippon Zeon Co.)

Matt agent (1)

SYLOID 79 (trade name: manufactured by Fuji Davisson Kagaku Co.

Hardener (1)

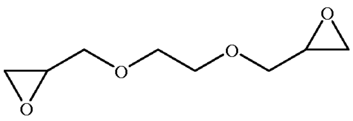

Mordant (2)

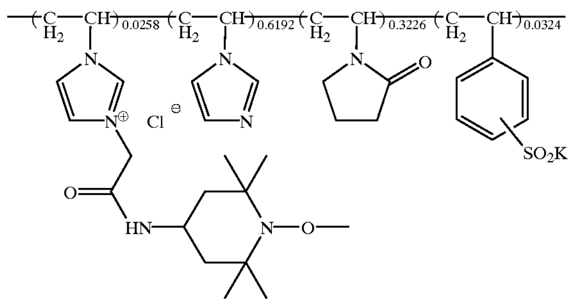

Then, a light-sensitive material for heat-development was produced by the following method.

First, the manner of forming a light-sensitive silver halide emulsion will be described. Light-sensitive silver halide emulsion (1) (emulsion for the fifth layer (680 nm light-sensitive layer))

A (I) solution and a (II) solution having compositions shown in Table 5 were simultaneously added to a vigorously-stirred aqueous solution having a composition shown in Table 4 over 19 minutes. After 5 minutes from the addition, a (III) solution having a composition shown in Table 5 was added thereto over 33 minutes, and a (IV) solution having a composition shown in Table 5 was added thereto over 33 minutes 30 seconds.

TABLE 4

| Composition | |
|---|---|
| $H_2O$ | 620 ml |
| Lime-processed gelatin | 20 g |
| KBr | 0.3 g |
| NaCl | 2 g |
| Silver halide solvent ① | 0.03 g |
| Sulfuric acid (0.5 mol/l) | 16 ml |
| Temperature | 45° C. |

TABLE 5

| | Solution (I) | Solution (II) | Solution (III) | Solution (IV) |
|---|---|---|---|---|
| $AgNO_3$ | 30 g | none | 70 g | none |
| $NH_4NO_3$ | 0.125 g | none | 0.375 g | none |
| KBr | none | 13.7 g | none | 44.1 g |
| NaCl | none | 3.6 g | none | 2.4 g |
| $K_2IrCl_6$ | none | none | none | 0.039 mg |
| Total volume | water to make 126 ml | water to make 132 ml | water to make 254 ml | water to make 252 ml |

Silver halide solvent 1

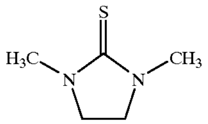

Further, after 15 min from the start of addition of solution (III), 150 ml of an aqueous solution containing 0.350% of sensitizing dye ① was added over 27 min.

Sensitizing dye 1

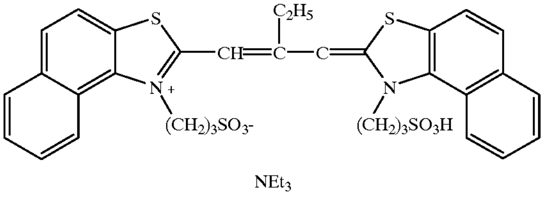

After washing with water and desalting (that was carried out using Settling Agent a, at a pH of 3.7 to 4.1) in a usual manner, 22 g of lime-processed ossein gelatin was added, and after adjusting the pH and pAg to 6.0 and 7.9 respectively, the chemical sensitization was carried out at 60° C. The compounds used in the chemical sensitization are shown in Table 6. In this way, 630 g of a monodisperse cubic silver chlorobromide emulsion having a deviation coefficient of 10.2% and an average grain size of 0.20 μm was obtained.

TABLE 6

| Chemicals used in chemical sensitization | Added amount |
|---|---|
| 4-hydroxy-6-methyl-1,3,3a,7--tetrazaindene | 0.36 g |
| Sodium thiosulfate | 6.75 mg |
| Antifoggant ① | 0.11 g |
| Antiseptic ① | 0.07 g |
| Antiseptic ② | 3.13 g |

Settling agent a

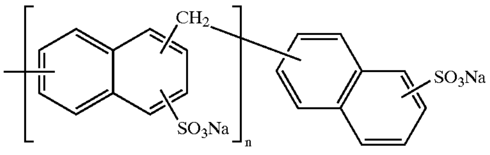

n < 10

TABLE 6-continued

| Chemicals used in chemical sensitization | Added amount |
|---|---|
| Antifoggant ① | |
| 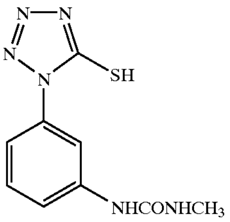 | |
| Antiseptic ① | |
| 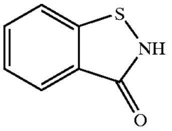 | |
| Antiseptic ② | |
| 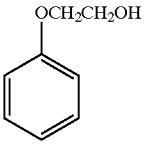 | |

Light-Sensitive Silver Halide Emulsion (2) (Emulsion for the Third Layer (750 nm Light-Sensitive Layer))

A (I) solution and a (II) solution having compositions shown in Table 8 were simultaneously added to a vigorously-stirred aqueous solution having a composition shown in Table 7 over 18 minutes. After 5 minutes from the addition, a (III) solution having a composition shown in Table 8 was added thereto over 24 minutes, and a (IV) solution having a composition shown in Table 8 was added thereto over 24 minutes 30 seconds.

TABLE 7

| Composition | |
|---|---|
| $H_2O$ | 620 ml |
| Lime-processed gelatin | 20 g |
| KBr | 0.3 g |
| NaCl | 2 g |
| Silver halide solvent ① | 0.03 g |
| Sulfuric acid (0.5 mol/l) | 16 ml |
| Temperature | 46° C. |

TABLE 8

| | Solution (I) | Solution (II) | Solution (III) | Solution (IV) |
|---|---|---|---|---|
| $AgNO_3$ | 30 g | none | 70 g | none |
| $NH_4NO_3$ | 0.125 g | none | 0.375 g | none |
| KBr | none | 13.7 g | none | 44.1 g |
| NaCl | none | 3.6 g | none | 2.4 g |
| $K_4[Fe(CN)_6]$ | none | none | none | 0.065 g |
| $K_2IrCl_6$ | none | none | none | 0.04 mg |
| Total volume | water to make 126 ml | water to make 131 ml | water to make 280 ml | water to make 289 ml |

After washing with water and desalting (that was carried out using Settling Agent b at a pH of 3.9) in a usual manner, 22 g of lime-processed ossein gelatin from which calcium had been removed (the calcium content: 150 ppm or less) was added, re-dispersing was made at 40° C., 0.39 g of 4-hydroxy-6-methyl-1,3,3a,7-tetrazaindene was added, and the pH and pAg were adjusted to 5.9 and 7.8 respectively. Thereafter the chemical sensitization was carried out at 70° C. using the chemicals shown in Table 9. At the end of the chemical sensitization, Sensitizing Dye ② in the form of a methanol solution (the solution having the composition shown in Table 10) was added. After the chemical sensitization, the temperature was lowered to 40° C. and then 200 g of a gelatin dispersion of the later-described Stabilizer ① was added, followed by stirring well, and kept in a casing. In this way, 938 g of a monodisperse cubic silver chlorobromide emulsion having a deviation coefficient of 12.6% and an average grain size of 0.25 μm was obtained. In this connection, the emulsion for a 750 nm light-sensitive layer had spectral sensitivity of the J-band type.

Settling agent b

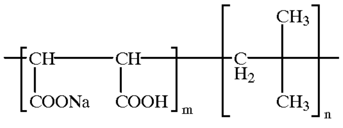

m + n = 1

TABLE 9

| Chemicals used in chemical sensitization | Added amount |
|---|---|
| 4-hydroxy-6-methyl-1,3,3a,7-tetrazaindene | 0.39 g |
| Triethylthiourea | 3.3 mg |
| Nucleic acid decomposition product | 0.39 mg |
| NaCl | 0.15 g |
| KI | 0.12 g |
| Antifoggant ② | 0.10 g |
| Antiseptic ① | 0.07 g |

TABLE 10

| Composition of dye solution | Added amount |
|---|---|
| Sensitizing dye ② | 0.19 g |
| Methanol | 18.7 ml |

Stabilizer ①

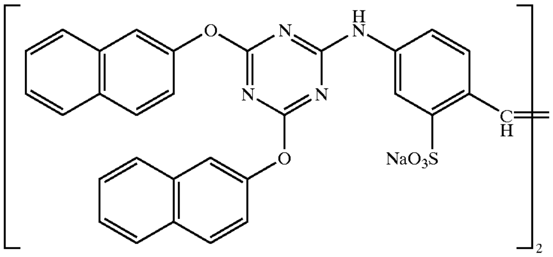

TABLE 10-continued

| Composition of dye solution | Added amount |
|---|---|

Sensitizing dye ②

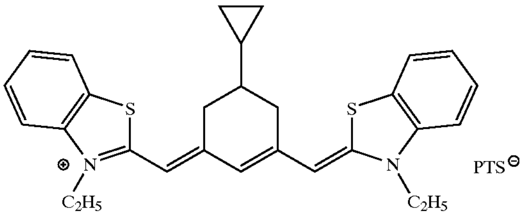

PTS = para-toluenesulfonic acid

Antifoggant ②

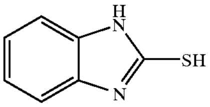

Light-Sensitive Silver Halide Emulsion (3) (Emulsion for the First Layer (810 nm Light-Sensitive Layer))

A (I) solution and a (II) solution having compositions shown in Table 12 were simultaneously added to a vigorously-stirred aqueous solution having a composition shown in Table 11 over 18 minutes. After 5 minutes from the addition, a (III) solution having a composition shown in Table 12 was added thereto over 24 minutes, and a (IV) solution having a composition shown in Table 12 was added thereto over 24 minutes 30 seconds.

TABLE 11

| Composition | |
|---|---|
| $H_2O$ | 620 ml |
| Lime-processed gelatin | 20 g |
| KBr | 0.3 g |
| NaCl | 2 g |
| Silver halide solvent ① | 0.03 g |
| Sulfuric acid (0.5 mol/l) | 16 ml |
| Temperature | 50° C. |

TABLE 12

| | Solution (I) | Solution (II) | Solution (III) | Solution (IV) |
|---|---|---|---|---|
| $AgNO_3$ | 30 g | none | 70.0 g | none |
| KBr | none | 13.7 g | none | 44.1 g |
| NaCl | none | 3.6 g | none | 2.4 g |
| $K_4[Fe(CN)_6]$ | none | none | none | 0.04 g |
| $K_2IrCl_6$ | none | none | none | 0.02 mg |
| Total volume | water to make 180 ml | water to make 181 ml | water to make 242 ml | water to make 250 ml |

After washing with water and desalting (that was carried out using settling Agent a, at a pH of 3.8) in a usual manner, 22 g of lime-processed ossein gelatin was added, and after adjusting the pH and pAg to 7.4 and 7.8 respectively, the chemical sensitization was carried out at 60° C. The compounds used in the chemical sensitization are shown in Table 13. Further, in the last of chemical sensitization, a solution of a sensitizing dye ③ in methanol was added (in the same way as the sensitizing dye ② shown in Table 10). The yield of the resulting emulsion was 683 g. The emulsion was a monodispersion cubic silver chlorobromide emulsion of which the coefficient of variation was 9.7% and the average grain size was 0.32 μm.

TABLE 13

| Chemicals used in chemical sensiization | Added amount |
|---|---|
| 4-hydroxy-6-methyl-1,3,3a,7-tetrazaindene | 0.38 g |
| Triethylthiorea | 3.1 mg |
| Antifoggant ② | 0.19 g |
| Antiseptic ① | 0.07 g |
| Antiseptic ② | 3.13 g |

Sensitizing dye ③

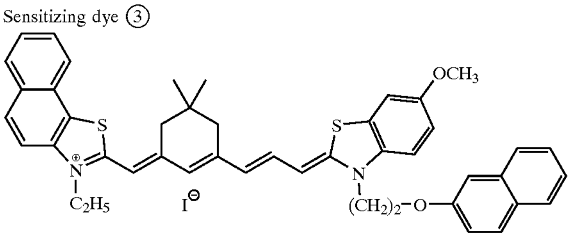

Preparation of Silver Chloride Fine-Grain Emulsion (Added to the First Layer (810 nm Light-Sensitive Layer))

A (I) solution and a (II) solution having compositions shown in Table 15 were simultaneously added to a vigorously-stirred aqueous solution having a composition shown in Table 14 over 4 minutes. After 3 minutes from the addition, a (III) solution and a (IV) solution having compositions shown in Table 15 were added thereto over 8 minutes.

TABLE 14

| Composition | |
|---|---|
| $H_2O$ | 3770 ml |
| Lime-processed gelatin | 60 g |
| NaCl | 0.8 g |
| Temperature | 38° C. |

TABLE 15

| | Solution (I) | Solution (II) | Solution (III) | Solution (IV) |
|---|---|---|---|---|
| $AgNO_3$ | 300 g | none | 300 g | none |
| $NH_4NO_3$ | 10 g | none | 10 g | none |
| NaCl | none | 108 g | none | 104 g |
| Total volume | water to make 940 ml | water to make 940 ml | water to make 1170 ml | water to make 1080 ml |

After washing with water and desalting (that was carried out using the above-shown Settling Agent a at a pH of 3.9) in a usual manner, 132 g of lime-processed ossein gelatin was added, re-dispersing was made at 35° C., 0.39 g of 4-hydroxy-6-methyl-1,3,3a,7-tetrazaindene was added, and the pH was adjusted to 5.7, to obtain silver chloride fine-grain emulsion. The yield of the resulting silver chloride fine-grain emulsion was 3,200 g, whose average grain size was 0.10 μm.

The preparation method of a gelatin dispersion of colloidal silver is described below.

To a well-stirred aqueous solution having the composition shown in Table 16, was added a Solution having the composition shown in Table 17, over 24 min. Thereafter, the washing with water using the above-shown Settling Agent a was carried out, then 43 g of lime-processed ossein gelatin was added, and the pH was adjusted to 6.3. In this way, 512 g of a dispersion having average grain size of 0.02 μm, and containing silver 2% and gelatin 6.8% was obtained.

TABLE 16

| Composition | |
|---|---|
| $H_2O$ | 620 ml |
| Dextrin | 16 g |
| NaOH (5 mol/l) | 41 ml |
| Temperature | 30° C. |

TABLE 17

| Composition | |
|---|---|
| $H_2O$ | 135 ml |
| $AgNO_3$ | 17 g |

The preparation methods of gelatin dispersions of hydrophobic additives are described below.

Gelatin dispersions of a yellow coupler and a built-in developing agent, a magenta coupler and a built-in developing agent, and, a cyan coupler and a built-in developing agent, whose formulations are shown in Table 18, were prepared, respectively. That is, the oil phase components were dissolved by heating to about 70° C., to form a uniform solution, and to the resultant solution, were added the aqueous phase components that had been heated to about 60° C., followed by stirring to mix and dispersing by a homogenizer for 10 min at 10,000 rpm. To the resultant dispersion, was added additional water, followed by stirring, to obtain a uniform dispersion.

TABLE 18

| | | Composition of dispersion | | |
|---|---|---|---|---|
| | | Yellow | Magenta | Cyan |
| Oil phase | Yellow coupler ① | 6.97 g | none | none |
| | Cyan coupler ① | none | none | 6.63 g |
| | Magenta coupler ① | none | 7.14 g | none |
| | Developing agent ① | 5.58 g | 5.71 g | 5.30 g |
| | Auxiliary developing agent ① | 0.51 g | 0.51 g | 0.51 g |
| | Antifoggant ③ | none | 0.03 g | 0.03 g |
| | Antifoggant ④ | 0.64 g | 0.08 g | none |
| | Antifoggant ⑤ | 0.30 g | none | none |
| | Surfactant ① | 0.2 g | 0.2 g | 0.2 g |
| | High-boiling solvent ① | 7.0 g | 7.0 g | 7.0 g |
| | Dye (a) | 0.59 g | none | 0.14 g |
| | Water | 0.2 ml | none | 0.3 ml |
| | Ethyl acetate | 16 ml | 16 ml | 16 ml |
| Aqueous phase | Lime-processed gelatin | 10.0 g | 10.0 g | 10.0 g |
| | Calcium nitrate | 0.05 g | 0.04 g | 0.05 g |
| | Zinc nitrate | none | 0.08 g | none |
| | Carboxymethyl cellulose | none | none | 0.07 g |
| | Water | 35 ml | 31 ml | 33 ml |
| | Water (after emulsification) | 40 ml | 43 ml | 31 ml |
| | Antiseptic ① | 0.003 g | 0.002 g | 0.03 g |

Antiseptic ①

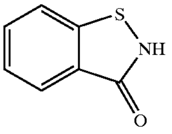

TABLE 18-continued

| | Composition of dispersion | | |
|---|---|---|---|
| | Yellow | Magenta | Cyan |

Dye (a)

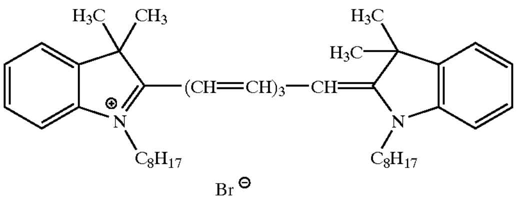

Auxiliary developing agent ①

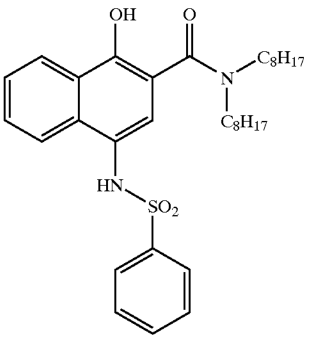

Surfactant ①

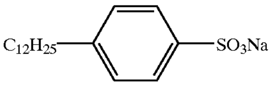

High-boiling solvent ①

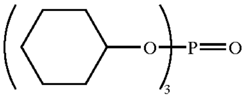

Antifoggant ③

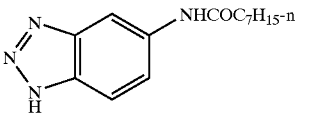

Antifoggant ④

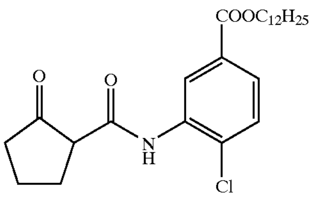

Antifoggant ⑤
Ascorbic acid palmitate
Developing agent ①

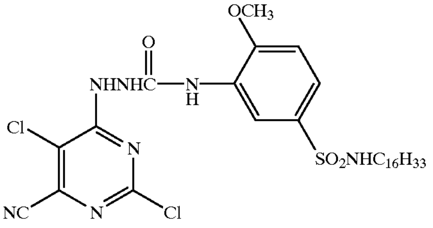

Compound (56) described in JP-A-9-152705
Yellow coupler ①

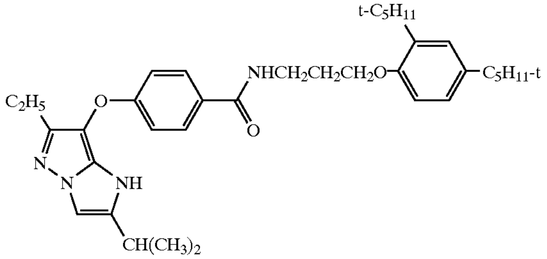

Compound (C-14) described in JP-A-9-152705
Magenta coupler ①

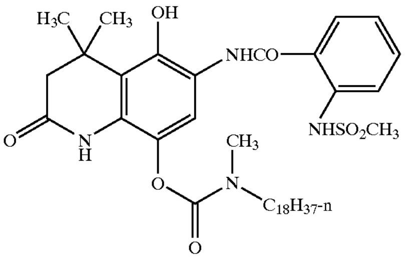

Compound (C-38) described in JP-A-9-152705
Cyan coupler ①

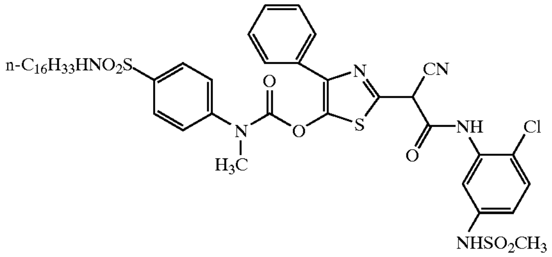

Compound (C-45) described in JP-A-9-152705

A gelatin dispersion of Antifoggants ④ and ⑥ and Auxiliary developing agent ① whose formulation is shown in Table 19 was prepared. That is, the oil phase components were dissolved by heating to about 60° C. to form a solution, and to the resultant solution, were added the aqueous phase components that had been heated to about 60° C., and after stirring and mixing them, the resultant mixture was dispersed for 10 min at 10,000 rpm by a homogenizer, to obtain a uniform dispersion.

TABLE 19

| Composition of dispersion | | |
|---|---|---|
| Oil phase | Antifoggant ④ | 1.0 g |
| | Antifoggant ⑥ | 0.8 g |
| | Auxiliary developing agent ① | 0.1 g |
| | High-boiling organic solvent ② | 2.3 g |
| | High-boiling organic solvent ① | 0.2 g |
| | Surfactant ① | 0.5 g |
| | Surfactant ② | 0.5 g |
| | Ethyl acetate | 10.0 ml |
| Aqueous phase | Lime-processed gelatin | 10.0 g |
| | Antiseptic ① | 0.004 g |
| | Calcium nitrate | 0.1 g |
| | Water | 35.0 ml |
| | Additional Water | 46 ml |

Antifoggant ⑥

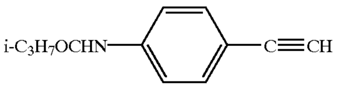

High-boiling organic solvent ②

$C_{26}H_{46.9}Cl_{7.1}$

EMPARA 40 (trade name: manufactured by Ajinomoto K.K.)

Surfactant ②

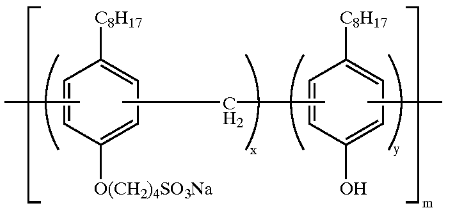

x:y = 4:6 m = 6.8

A gelatin dispersion of Reducing Agent ① whose formulation is shown in Table 20 was prepared. That is, the oil phase components were dissolved by heating to about 60° C. to form a solution, and to the resultant solution, were added the aqueous phase components that had been heated to about 60° C., and after stirring and mixing them, the resultant mixture was dispersed for 10 min at 10,000 rpm by a homogenizer, to obtain a uniform dispersion. From the thus-obtained dispersion, ethyl acetate was removed off using a vacuum organic solvent removing apparatus.

TABLE 20

| Composition of dispersion | | |
|---|---|---|
| Oil phase | Reducing agent ① | 7.5 g |
| | High-boiling organic solvent ③ | 4.7 g |
| | Surfactant ① | 1.9 g |
| | Ethyl acetate | 14.4 ml |
| Aqueous phase | Acid-processed gelatin | 10.0 g |
| | Antispetic ① | 0.002 g |
| | Antispetic ③ | 1.004 g |
| | Calcium nitrate | 2.1 g |
| | Water | 136.7 ml |

TABLE 20-continued

Composition of dispersion

Reducing agent ①

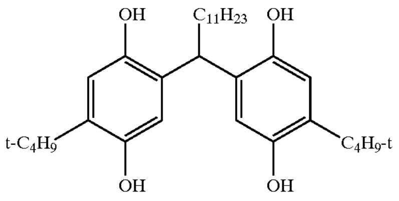

High-boiling organic solvent ③

$(C_4H_9(C_2H_5)CHCH_2O)_3—P{=}O$

Antiseptic ③

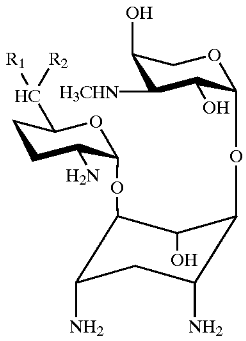

| $R_1$ | $R_2$ |
|---|---|
| $CH_3$ | $NHCH_3$ |
| $CH_3$ | $NH_2$ |
| H | $NH_2$ |
| H | $NHCH_3$ |

A dispersion of Polymer Latex (a) whose formulation is shown in Table 21 was prepared. That is, while a mixed solution of Polymer Latex (a), Surfactant ③, and water whose amounts are shown in Table 21 was stirred, Anionic Surfactant ① was added thereto, over 10 min, to obtain a uniform dispersion. The resulting dispersion was repeatedly diluted with water and concentrated using a ultrafiltration module (Ultrafiltration Module: ACV-3050, trade name, manufactured by Asahi Chemical Industry Co., Ltd.), to bring the salt concentration of the dispersion to ⅑, thereby obtaining the intended dispersion.

TABLE 21

| Composition of dispersion | |
|---|---|
| Polymer Latex (a) aqueous solution (solid content 13%) | 108 ml |
| Surfactant ③ | 20 g |
| Anionic surfactant ① aqueous solution (5%) | 600 ml |
| Water | 1232 ml |

Surfactant ③

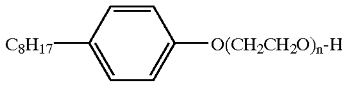

n = 85

TABLE 21-continued

| Composition of dispersion |
|---|

Anionic surfactant ①

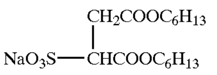

Polymer Latex a

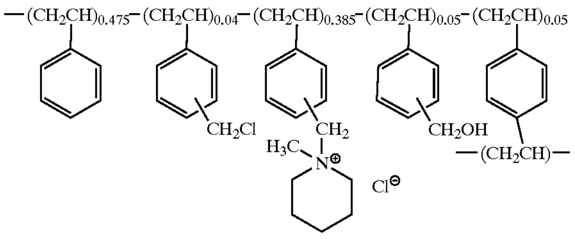

A gelatin dispersion of Stabilizer ① whose formulation is shown in Table 22 was prepared. That is, the oil phase components were dissolved at room temperature to form a solution, and to the resultant solution, were added the aqueous phase components that had been heated to about 40° C., and after stirring and mixing them, the resultant mixture was dispersed for 10 min at 10,000 rpm by a homogenizer. To the resultant dispersion, was added additional water, followed by stirring, thereby obtaining a uniform dispersion.

TABLE 22

| Composition of dispersion | | |
|---|---|---|
| Oil phase | Stabilizer ① | 40 g |
| | Sodium hydroxide | 0.3 g |
| | Methanol | 62.8 g |
| | High-boiling organic solvent ⑥ | 0.9 g |
| Aqueous phase | Gelatin from which calcium had been removed (Ca content 100 ppm or less) | 10 g |
| | Antiseptic ① | 0.04 g |
| | Water | 320.5 ml |

A gelatin dispersion of zinc hydroxide was prepared according to the formulation shown in Table 23. That is, after the components were mixed and dissolved, dispersing was carried out for 30 min in a mill, using glass beads having an average particle diameter of 0.75 mm. Then the glass beads were separated and removed off, to obtain a uniform dispersion. (Zinc hydroxide having a grain size of 0.25 $\mu$m was used.)

TABLE 23

| Composition of dispersion | |
|---|---|
| Zinc hydroxide | 15.9 g |
| Carboxymethyl cellulose | 0.7 g |
| Poly (sodium acrylate) | 1.07 g |
| Lime-processed gelatin | 4.2 g |
| Water | 100 ml |
| High-boiling organic solvent ① | 0.4 g |

The preparation method of a gelatin dispersion of a matt agent that was to be added to the protective layer is described.

A solution containing PMMA dissolved in methylene chloride was added, together with a small amount of a surfactant, to gelatin, and they were stirred and dispersed at high speed. Then the methylene chloride was removed off using a vacuum solvent removing apparatus, to obtain a uniform dispersion having an average particle size of 4.3 $\mu$m.

Using the above materials, Light-Sensitive Element 101 shown in Tables 24 to 25 was prepared.

TABLE 24

| Number of layer | Name of layer | Additive | Added amount ($mg/m^2$) |
|---|---|---|---|
| Constitution of Main Materials of Light-Sensitive Element 101 | | | |
| Seventh layer | Protective layer | Acid-processed gelatin | 442 |
| | | Reducing agent ① | 47 |
| | | High-boiling organic solvent ① | 30 |
| | | Colloidal silver grains | 2 |
| | | Matting agent (PMMA resin) | 17 |
| | | Surfactant ① | 16 |
| | | Surfactant ④ | 9 |
| | | Surfactant ⑤ | 2 |
| | | Calcium nitrate | 5 |
| Sixth layer | Intermediate layer | Lime-processed gelatin | 862 |
| | | Zinic hydroxide | 577 |
| | | Antifoggant ④ | 86 |
| | | Antifoggant ⑥ | 69 |
| | | Auxiliary developing agent ① | 9 |
| | | High-boiling organic solvent ① | 17 |
| | | High-boiling organic solvent ② | 198 |
| | | Surfactant ① | 43 |
| | | Surfactant ② | 43 |
| | | Dispersion of Polymer Latex a | 5 |
| | | Water-soluble polymer ① | 5 |
| | | Calcium nitrate | 17 |
| Fifth layer | 680 nm-light-sensitive layer | Lime-processed gelatin | 588 |
| | | Light-sensitive silver halide emulsion (1) | 301 |
| | | Magenta coupler ① | 420 |
| | | High-boiling organic solvent ① | 412 |
| | | Developing agent ① | 336 |
| | | Antifoggant ③ | 2 |
| | | Antifoggant ④ | 5 |
| | | Surfactant ① | 12 |
| | | Auxiliary developing agent ① | 30 |
| | | Water-soluble polymer ① | 11 |
| Forth layer | Intermeduate layer | Lime-processed gelatin | 862 |
| | | Zinic hydroxide | 271 |
| | | Antifoggant ⑥ | 7 |
| | | Auxiliary developing agent ① | 57 |
| | | High-boiling organic solvent ① | 101 |
| | | High-boiling organic solvent ② | 9 |
| | | Surfactant ① | 21 |
| | | Surfactant ② | 21 |
| | | Water-soluble polymer ① | 4 |
| | | Calcium nitrate | 6 |
| | | Dispersion of Polymer Latex a | 5 |
| Table 25 (continued from Table 24) | | | |
| Third layer | 750 nm-light-sensitive layer | Lime-processed gelatin | 588 |
| | | Light-sensitive silver halide emulsion (2) | 106 |
| | | Stabilizer ① | 8 |
| | | Developing agent ① | 312 |
| | | Cyan coupler ① | 390 |
| | | Dya (a) | 13 |
| | | High-boiling organic solvent ① | 412 |
| | | Auxiliary developing agent ① | 30 |
| | | Antifoggant ③ | 2 |
| | | Surfactant ① | 12 |
| | | Carboxymethyl cellulose | 7 |
| | | Water-soluble polymer ① | 11 |

TABLE 24-continued

| Number of layer | Name of layer | Additive | Added amount (mg/m$^2$) |
|---|---|---|---|
| Second layer | Intermediate layer | Lime-processed gelatin | 862 |
| | | Antifoggant (6) | 7 |
| | | High-boiling organic solvent (1) | 101 |
| | | High-boiling organic solvent (2) | 9 |
| | | Auxiliary developing agent (1) | 57 |
| | | Surfactant (1) | 21 |
| | | Surfactant (2) | 21 |
| | | Water-soluble polymer (2) | 25 |
| | | Calcium nitrate | 6 |
| First layer | 810 nm-light-sensitive layer | Lime-processed gelatin | 588 |
| | | Light-sensitive silver halide emsulion (3) | 311 |
| | | Ultrafine-grain silver chloride emulsion | 30 |
| | | Stabilizer (1) | 8 |
| | | Yellow coupler (1) | 410 |
| | | Developing agent (1)/ 328 | |
| | | Dye (a) | 42 |
| | | High-boiling organic solvent (1) | 412 |
| | | Surfactant (1) | 12 |
| | | Auxiliary developing agent (1) | 30 |
| | | Antifoggant (4) | 38 |
| | | Antifoggant (5) | 18 |
| | | Water-soluble polymer (2) | 40 |
| | | Hardener (1) | 45 |

Support (Paper support whose both surfaces were laminated with polyethylene: thickness 135 $\mu$m)

High-boiling solvent (6)

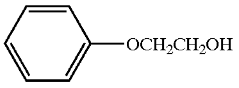

Surfactant (4)

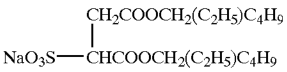

Surfactant (5)

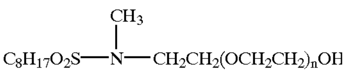

n = 15

Water-soluble polymer (1)

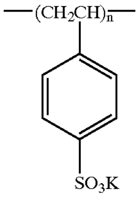

0.1 mol/1NaCl 30° C.
Limiting viscosity = 0.8
Molecular weight 1,000,000

TABLE 24-continued

| Number of layer | Name of layer | Additive | Added amount (mg/m$^2$) |
|---|---|---|---|

Water-soluble polymer (2)

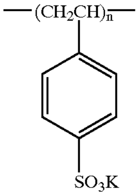

0.1 mol/1NaCl 30° C.
Limiting viscosity = 1.6
Molecular weight 1,000,000

Hardener (1)

$CH_2{=}CHSO_2CH_2SO_2CH{=}CH_2$

Then, light-sensitive elements 102–105 were formed in the same manner as the light-sensitive element 101, except that the developing agent (1) and the yellow coupler (1) shown in Table 18 were changed to each combination shown in Table 26. Furthermore, light-sensitive elements 106–109 were formed in the same manner as the light-sensitive element 101, except that the developing agent (1) and the magenta coupler (1) shown in Table 18 were changed to each combination shown in Table 27.

TABLE 26

| Light-sensitive material | Yellow coupler | Developing agent | Remarks |
|---|---|---|---|
| 101 | Yellow coupler (1) | Developing agent (1) | Comparative example |
| 102 | Yellow coupler (1) | R-22 | This invention |
| 103 | Cp-1 | R-22 | This invention |
| 104 | Cp-2 | R-25 | This invention |
| 105 | Cp-3 | R-28 | This invention |

TABLE 27

| Light-sensitive material | Magenta coupler | Developing agent | Remarks |
|---|---|---|---|
| 101 | Magenta coupler (1) | Developing agent (1) | Comparative example |
| 106 | Magenta coupler (1) | R-22 | This invention |
| 107 | Cp-6 | R-22 | This invention |
| 108 | Cp-7 | R-26 | This invention |
| 109 | Cp-10 | R-31 | This invention |

Each of these light-sensitive materials obtained in the above-mentioned way was combined with the dye fixation material R101. From each combination, an image was outputted, using PG-3000 (trade name) made by Fuji Photo Film Co., Ltd. Heating temperature was 83° C., and time was 20 seconds or 35 seconds.

The images outputted from the light-sensitive materials 102–109 were vivid color images. Thus, when the compound of the present invention was used, the sharpness of the resultant image was excellent.

A reflection densitometer X-rite 304 (trade name) made by X-rite Company was used to measure Dmax (highest density) and Dmin (lowest density) of the thus obtained images.

The results are shown in Table 28.

TABLE 28

| Light-sensitive material | 20 seconds processing Dmax | Dmin | 35 seconds processing Dmax | Dmin | Remarks |
|---|---|---|---|---|---|
| 101 | 0.93 | 0.13 | 1.56 | 0.15 | Comparative example (yellow) |
| 102 | 1.54 | 0.13 | 2.03 | 0.14 | This invention (yellow) |
| 103 | 1.69 | 0.14 | 2.15 | 0.15 | This invention (yellow) |
| 104 | 1.77 | 0.12 | 2.18 | 0.13 | This invention (yellow) |
| 105 | 1.99 | 0.12 | 2.33 | 0.13 | This invention (yellow) |
| 101 | 1.25 | 0.14 | 1.78 | 0.19 | Comparative example (magenta) |
| 106 | 2.18 | 0.14 | 2.74 | 0.15 | This invention (magenta) |
| 107 | 2.01 | 0.12 | 2.47 | 0.15 | This invention (magenta) |
| 108 | 2.1 | 0.15 | 2.58 | 0.16 | This invention (magenta) |
| 109 | 1.94 | 0.14 | 2.39 | 0.15 | This invention (magenta) |

As is apparent from Table 28, it can be understood that the light-sensitive materials using the compound of the present invention exhibited good photographic performances in a short time. The resultant images were stable under conditions of high temperature and humidity and the like.

The images obtained from the light-sensitive materials were irradiated with Xenon light having an illumination of 170,000 lux for a week. With respect to the portions having the magenta density or yellow density of 1.0, dye remaining rates were obtained. The results are shown in Table 29.

TABLE 29

| Light-sensitive material | Residual rate of dye (%) | Remarks |
|---|---|---|
| 101 | 70.2 | Comparative example (yellow) |
| 102 | 85.6 | This invention (yellow) |
| 103 | 81.2 | This invention (yellow) |
| 104 | 77.9 | This invention (yellow) |
| 105 | 83.5 | This invention (yellow) |
| 101 | 58.5 | Comparative example (magenta) |
| 106 | 66.7 | This invention (magenta) |
| 107 | 80.1 | This invention (magenta) |
| 108 | 82.6 | This invention (magenta) |
| 109 | 84.1 | This invention (magenta) |

The results in Tables 28 and 29 demonstrate that the light-sensitive materials using the compound of the present invention had both of high developed color density and excellent fastness to light.

Example 1-2

In the method described in Example 1 of JP-A-09-152702, the developing agents (Exemplified compounds R-22, R-23, R-25, R-10, R-11 and R-30) of the present invention were used in place of the compound example D-7. As a consequence, images were obtained which were excellent in color formation efficiency and had good storage stability, similar in the above Examples 1-1.

Example 1-3

A light-sensitive element (Sample 301) was produced by the following method.

First, the method of preparing silver halide emulsions will be described.

Eight kinds of silver halide emulsion grains (Emulsion-A to Emulsion-F) and Emulsion-T and Emulsion-U, which will be described below, were prepared by the following emulsion grain preparing method.

Preparation of Emulsion A (Octahedron Internal-Latent-Image-Type Direct Positive Emulsion):

To 1000 ml of an aqueous gelatin solution containing 0.05 M of potassium bromide, 1 g of 3,6-dithia-1,8-octanediol, 0.034 mg of lead acetate, and 60 g of deionized gelatin containing 100 ppm or less of Ca, was added 300 ml of 0.4 M aqueous silver nitrate solution over 40 minutes with the temperature being kept at 75° C., while in a controlled double jet method of adding the aqueous silver aqueous nitrate solution and a 0.4 M aqueous potassium bromide solution, the addition rate of the aqueous potassium bromide solution was adjusted in such a manner that pBr would be 1.60.

When the addition was finished, octahedron silver bromide crystal, which will be referred to as core grains hereinafter, was generated. The core grains had an average grain diameter (sphere equivalent diameter) of about 0.7 μm, and the grain sizes thereof were substantially even.

Then, chemical sensitization of core was performed under the following conditions.

1. Tank: a tank, the metal surface of which had a coating layer (thickness: 120 μm) made of a fluorine resin material FEP (polytetrafluoroethylene; Teflon, trade name) made by Du Pont. The tank had a semi-ball shaped bottom.

2. Stirring fan: a propeller of a jointless integration-type, the metal surface of which was coated with Teflon.

To a preparation solution of the Emulsion-A were added 1 mg of sodium thiosulfate, and 3 ml of an aqueous solution of 90 mg of potassium tetrachloroaurate and 1.2 g of potassium bromide in 1000 ml of water, and then the solution was heated at 75° C. for 80 minutes to conduct chemical sensitization. To the thus chemically-sensitized emulsion solution was added 0.15 M of potassium bromide. Thereafter, in the same manner as in the preparation of the core grains, to the resultant solution was added 670 ml of a 0.9 M aqueous silver nitrate solution over 70 minutes with the temperature being kept at 75° C., while in a controlled double jet method of adding the aqueous silver nitrate solution and a 0.9 M aqueous potassium bromide solution, the addition rate of the aqueous potassium bromide solution was adjusted in such a manner that pBr would be 1.30.

This emulsion was washed with water in a usual flocculation manner, and then thereto were added the above-mentioned gelatin, 2-phenoxyethanol and methyl p-hydroxybenzoate, to obtain octahedron silver bromide crystal, which will be referred to as internal-latent-image-type core/shell grains hereinafter, having an average grain diameter (sphere equivalent diameter) of about 1.2 μm. The internal-latent-image-type core/shell grains had a substantially even grain size.

Then, to the internal-latent-image-type core/shell grain emulsion, was added 3 ml of an aqueous solution of 100 mg of sodium thiosulfate and 40 mg of sodium tetraborate in 1000 ml of water, and then thereto was added 14 mg of poly(N-vinylpyrrolidone). The resultant emulsion was heated and ripened at 60° C. Thereafter, 0.005 M of potassium bromide was added thereto, to prepare an octahedron internal-latent-image-type direct positive emulsion. Preparation of Emulsions-B to -F (octahedron internal-latent-image-type direct positive emulsions):

In the method of preparation of the Emulsion-A, the times for adding the aqueous silver nitrate solution and the aqueous potassium bromide solution were changed and the amounts of the chemicals added were changed, to obtain octahedron internal-latent-image-type direct positive silver halide emulsions, each of which had an average grain diameter (sphere equivalent diameter) shown in Table 30. The emulsions had a substantially even grain size.

TABLE 30

| Name of emulsion | Average grain diameter μm |
|---|---|
| B | 0.93 |
| C | 1.20 |
| D | 0.94 |
| E | 0.74 |
| F | 0.66 |

Preparation of Emulsion-T (Hexagonal Tabular Internal-Latent-Image-Type Direct Positive Emulsion):

To 1.2 liter of an aqueous gelatin solution containing 0.05 M of potassium bromide and 0.7% by weight of gelatin having an average molecular weight of 100,000 or less, were simultaneously added 33 ml of a 1.4 M aqueous silver nitrate solution containing the above-mentioned gelatin and 33 ml of a 2M aqueous potassium bromide solution over 1 minute by a double jet method while vigorously stirred. During this addition, the aqueous gelatin solution was kept at 30° C. Furthermore, thereto was added 300 ml of a gelatin solution containing 10% by mass of deionized gelatin having 100 ppm or less of Ca, and the temperature of the resultant emulsion was raised to 75° C.

Then, 40 ml of a 0.9 M aqueous silver nitrate solution was added thereto over 3 minutes, and then a solution containing 25% by mass of ammonia in water was added thereto. The emulsion was ripened at 75° C. to ripen. After the ripening, the ammonia was neutralized, and 5 mg of lead acetate (in the form of an aqueous solution) was added thereto. Thereafter, a 1M aqueous silver nitrate solution and a 1M aqueous potassium bromide solution were added thereto at a given accelerated flow rate (the flow rate at the finish time was six times larger than that at the initial time) by a double jet method while pBr was kept at 2.5. The volume of the aqueous silver nitrate solution to be used was 500 ml.

The thus produced grains, which will be referred to as core grains, were washed with water in a usual flocculation manner, and then thereto were added gelatin, 2-phenoxyethanol and methyl p-hydroxybenzoate, to obtain 750 g of hexagonal tabular core grains.

The resultant hexagonal tabular core grains had an average diameter of circle equivalent to projected area of 0.9 μm, and an average thickness of 0.20 μm. The hexagonal tabular grains occupied 95% of the total projection area.

Chemical sensitization of core was performed under the following conditions.

1. Tank: a tank, the metal surface of which had a coating layer (thickness: 120 μm) made of a fluorine resin material FEP made by Du Pont. The tank had a semi-ball shaped bottom.

2. Stirring fan: a propeller of a jointless integration-type, the metal surface of which was coated with Teflon.

To 200 g of the hexagonal tabular core emulsion, were added 1300 ml of water, 0.11 M of potassium bromide, and 40 g of deionized gelatin, and then the temperature of the mixture was raised to 75° C. Thereafter, thereto were added 0.3 g of 3,6-dithia-1,8-octanediol, 10 mg of sodium benzenethiosulfate, 2.4 ml of an aqueous solution wherein 90 mg of potassium tetrachloroaurate and 1.2 g of potassium bromide were dissolved into 1000 ml of water, and 15 mg of lead acetate (in the form of an aqueous solution), and then the mixture was heated at 75° C. for 180 minutes to perform chemical sensitization. In the same manner as the time of preparing the core grains, a 2M aqueous silver nitrate solution and a 2.5M aqueous potassium bromide solution were added to the thus chemically-sensitized core grains at a given accelerated flow rate (the flow rate at the finish time was three times larger than that at the initial time) by a double jet method, while the addition speed of the aqueous potassium bromide solution was adjusted so that pBr would be 2.2. The volume of the aqueous silver nitrate solution to be used was 810 ml.

Thereto was added 0.3 mole of potassium bromide, and then this emulsion was washed with water in a usual flocculation manner. Gelatin was added thereto. In this way, a hexagonal tabular internal-latent-image type core/shell emulsion was obtained. The resultant hexagonal tabular grains had an average diameter of circle equivalent to projected area of 2.0 μm, an average thickness of 0.38 μm, and an average volume size of 1.3 $(\mu m)^3$. The hexagonal tabular grains occupied 88% of the total projected area.

Then, to this hexagonal tabular internal-latent-image type core/shell emulsion was added 15 ml of an aqueous solution wherein 10 mg of sodium thiosulfate and 40 mg of sodium tetraborate were dissolved into 1000 ml of water. Furthermore, 20 mg of poly(N-vinylpyrrolidone) was added thereto. The emulsion was heated at 70° C. for 100 minutes to perform chemical sensitization of the surfaces of the grains. Thus, a hexagonal tabular internal-latent-image-type direct positive emulsion was prepared.

Preparation of Emulsion-U (Hexagonal Tabular Internal-Latent-Image-Type Direct Positive Emulsion):

When the outer shell of the Emulsion-T was formed, 0.15 mol % of iodide was uniformly incorporated thereto and then the amount of the formed outer shell was increased. Thus, hexagonal tabular grains were obtained, which had an average diameter of circle equivalent to projected area of 2.5 μm, an average grain thickness of 0.45 μm, and an average volume size of 1.7 $(\mu m)^3$, and which occupied 88% of the total projected area.

Then, thereto was added AgI fine-particle Emulsion-X in an amount corresponding to 0.04 mol % of the silver amount required for the formation of the grains at the initial time of chemical sensitization of the shell of the hexagonal tabular internal-latent-image-type core/shell emulsion. Thereafter, the resultant emulsion was subjected to the same shell chemical sensitization as in the case of the Emulsion-T, so as to prepare a hexagonal tabular internal-latent-image-type direct positive emulsion.

Preparation of Emulsion-X (AgI Fine-Particle Emulsion)

To water were added 0.5 g of potassium iodide and 26 g of gelatin. To the solution, the temperature of which was kept at 35° C., were added 80 ml of a silver nitrate solution containing 40 g of silver nitrate in water and 80 ml of a solution containing 39 g of potassium iodide in water over 5 minutes while the solution was stirred. At this time, each of the addition flow rates of the aqueous silver nitrate solution and the aqueous potassium iodide solution was set to 8 ml/minute at the initial time of the addition. The addition flow rates were linearly accelerated so that the addition of 80 ml of each of the solutions would be finished in 5 minutes.

After the formation of the grains was finished in this way, soluble salts were removed at 35° C. by a sedimentation method. Then, the temperature of the resultant solution was raised to 40° C., and then thereto were added 10.5 g of gelatin and 2.5 g of phenoxyethanol. The pH of the solution was adjusted to 6.8 with caustic sodium. The amount of the resultant emulsion was 730 g. The emulsion was monodispersive AgI fine grains having an average diameter of 0.015 μm.

The Emulsions-A to -F, -T and -U were used in the following manner to form a light-sensitive element (Sample 301) for comparison, having structures shown in Tables 31–35. Sensitizing dyes were added at the time of the end of shell chemical sensitization in accordance with dye kinds, dispersion forms, addition temperatures, and amounts shown in Table 36.

TABLE 31

Constitution of Main materials for Light-Sensitive Element 301

| Number of layer | Name of layer | Additive | Coated amount ($g/m^2$) |
|---|---|---|---|
| 24th layer | Protective layer | Matting agent (1) | 0.3514 |
| | | Gelatin | 0.196 |
| | | Surfactant (1) | $4.01 \times 10^{-3}$ |
| | | Surfactant (2) | $4.671 \times 10^{-3}$ |
| | | Surfactant (3) | $9.398 \times 10^{-3}$ |
| | | Additive (1) | $8.710 \times 10^{-3}$ |
| | | Additive (5) | $5.260 \times 10^{-3}$ |
| | | Additive (24) | $6.789 \times 10^{-3}$ |
| 23rd layer | Ultraviolet absorbing layer | Ultraviolet absorber (1) | $8.252 \times 10^{-2}$ |
| | | Ultraviolet absorber (2) | $4.355 \times 10^{-2}$ |
| | | Ultraviolet absorber (3) | $1.146 \times 10^{-2}$ |
| | | Surfactant (3) | $1.241 \times 10^{-2}$ |
| | | Additive (1) | $1.213 \times 10^{-2}$ |
| | | Additive (5) | $1.394 \times 10^{-2}$ |
| | | Additive (24) | $5.881 \times 10^{-5}$ |
| | | Additive (25) | $1.164 \times 10^{-4}$ |
| | | Hardener (1) | $7.462 \times 10^{-2}$ |
| | | Hardener (2) | $2.488 \times 10^{-2}$ |
| | | Gelatin | 0.299 |
| 22nd layer | Blue-light-sensitive layer (high speed) | Internal-latent-image-type direct positive emulsion: U | 0.460 |
| | | Nucleating agent (1) | $5.124 \times 10^{-6}$ |
| | | Additive (22) | $4.198 \times 10^{-6}$ |
| | | Additive (23) | $1.542 \times 10^{-6}$ |
| | | Additive (24) | $7.696 \times 10^{-6}$ |
| | | Additive (3) | $4.804 \times 10^{-3}$ |
| | | Additive (4) | $1.405 \times 10^{-2}$ |
| | | Additive (5) | $3.818 \times 10^{-6}$ |
| | | Gelatin | 0.513 |
| 21st layer | Blue-light-sensitive layer (low speed) | Internal-latent-image-type direct positive emulsion: A | 0.0745 |
| | | Internal-latent-image-type direct positive emulsion: B | 0.0745 |
| | | Nucleating agent (1) | $2.501 \times 10^{-6}$ |
| | | Additive (3) | $3.735 \times 10^{-3}$ |
| | | Additive (5) | $1.724 \times 10^{-2}$ |
| | | Additive (24) | $7.603 \times 10^{-5}$ |
| | | Additive (1) | $3.771 \times 10^{-3}$ |
| | | Surfactant (5) | $7.750 \times 10^{-3}$ |
| | | Gelatin | 0.309 |
| 20th layer | White reflection layer | Titanium dioxide | 0.4151 |
| | | Additive (1) | $7.667 \times 10^{-3}$ |
| | | Surfactant (1) | $9.354 \times 10^{-5}$ |
| | | Additive (5) | $1.348 \times 10^{-2}$ |
| | | Additive (24) | $1.117 \times 10^{-4}$ |
| | | Additive (26) | $8.384 \times 10^{-3}$ |
| | | Additive (8) | $3.316 \times 10^{-3}$ |
| | | Gelatin | 0.254 |

Table 32 (continued from Table 31)

| Number of layer | Name of layer | Additive | Coated amount ($g/m^2$) |
|---|---|---|---|
| 19th layer | Yellow colored material layer | Color developing agent ① | 0.348 |
| | | Yellow coupler ① | 0.317 |
| | | High-boiling organic solvent (1) | 0.350 |
| | | Surfactant (5) | $1.700 \times 10^{-2}$ |
| | | Additive (24) | $1.496 \times 10^{-3}$ |

TABLE 31-continued

Constitution of Main materials for Light-Sensitive Element 301

| Number of layer | Name of layer | Additive | Coated amount ($g/m^2$) |
|---|---|---|---|
| | | Additive (1) | $7.032 \times 10^{-3}$ |
| | | Gelatin | 0.793 |
| 18th layer | Intermediate layer | Additive (10) | $1.010 \times 10^{-2}$ |
| | | Surfactant (1) | $3.425 \times 10^{-4}$ |
| | | Additive (1) | $7.039 \times 10^{-3}$ |
| | | Additive (23) | $1.605 \times 10^{-2}$ |
| | | Additive (24) | $6.540 \times 10^{-5}$ |
| | | Gelatin | 0.332 |
| 17th layer | Color mixing prevented layer | Color mixing prevention agent (1) | 0.312 |
| | | Poly(methyl methacrylate) | 0.538 |
| | | Surfactant (5) | $3.700 \times 10^{-2}$ |
| | | Additive (1) | $7.039 \times 10^{-3}$ |
| | | Additive (12) | 0.383 |
| | | Additive (26) | $1.562 \times 10^{-2}$ |
| | | Gelatin | 0.640 |
| 16th layer | Green-light-sensitive layer (high speed) | Internal-latent-image-type direct positive emulsion: T | 0.435 |
| | | Nucleating agent (1) | $2.391 \times 10^{-6}$ |
| | | Additive (22) | $6.403 \times 10^{-2}$ |
| | | Additive (23) | $1.595 \times 10^{-2}$ |
| | | Additive (3) | $7.988 \times 10^{-2}$ |
| | | Additive (5) | $3.687 \times 10^{-2}$ |
| | | Additive (24) | $2.161 \times 10^{-2}$ |
| | | Additive (26) | $2.623 \times 10^{-3}$ |
| | | Additive (1) | $7.803 \times 10^{-2}$ |
| | | Surfactant (5) | $3.792 \times 10^{-2}$ |
| | | High-boiling organic solvent (2) | $4.182 \times 10^{-2}$ |
| | | Gelatin | 0.615 |
| 15th layer | Green-light-sensitive layer (low speed) | Internal-latent-image-type direct positive emulsion: C | 0.130 |
| | | Internal-latent-image-type direct positive emulsion: D | 0.130 |
| | | Nucleating agent (1) | $1.843 \times 10^{-6}$ |
| | | Additive (3) | $4.048 \times 10^{-2}$ |
| | | Additive (22) | $2.204 \times 10^{-2}$ |
| | | Additive (23) | $4.048 \times 10^{-2}$ |
| | | Additive (24) | $8.331 \times 10^{-5}$ |
| | | Additive (26) | $1.329 \times 10^{-3}$ |
| | | Additive (5) | $2.146 \times 10^{-2}$ |
| | | Additive (1) | $4.094 \times 10^{-3}$ |
| | | Surfactant (5) | $1.933 \times 10^{-2}$ |
| | | Gelatin | 0.329 |

Table 33 (continued from Table 31)

| Number of layer | Name of layer | Additive | Coated amount ($g/m^2$) |
|---|---|---|---|
| 14th layer | Intermediate layer | Additive (1) | $6.989 \times 10^{-3}$ |
| | | Surfactant (1) | $2.822 \times 10^{-4}$ |
| | | Additive (5) | $1.162 \times 10^{-2}$ |
| | | Additive (24) | $5.242 \times 10^{-5}$ |
| | | Gelatin | 0.266 |
| 13th layer | Magenta colored material layer | Color developing agent ① | 0.272 |
| | | Magenta coupler ① | 0.303 |
| | | High-boiling organic solvent (1) | 0.320 |
| | | Additive (13) | $8.462 \times 10^{-4}$ |
| | | Additive (5) | $1.740 \times 10^{-2}$ |
| | | Additive (24) | $5.653 \times 10^{-4}$ |
| | | Surfactant (5) | $1.820 \times 10^{-2}$ |
| | | Additive (14) | $2.039 \times 10^{-2}$ |
| | | Additive (1) | $8.247 \times 10^{-3}$ |
| | | Gelatin | 0.405 |
| 12th layer | Intermediate layer | Additive (10) | $3.806 \times 10^{-3}$ |
| | | Surfactant (1) | $3.002 \times 10^{-4}$ |
| | | Additive (1) | $7.064 \times 10^{-3}$ |
| | | Gelatin | 0.283 |
| 11th layer | Color-mix preventing layer | Color mixing prevention agent (1) | 0.320 |
| | | Poly(methyl methacrylate) | 0.554 |
| | | Surfactant (5) | $3.806 \times 10^{-2}$ |
| | | Additive (1) | $7.039 \times 10^{-3}$ |
| | | Additive (12) | 0.554 |
| | | Additive (26) | $1.607 \times 10^{-2}$ |
| | | Gelatin | 0.658 |
| 10th layer | Red-light-sensitive layer (high | Internal-latent-image-type direct positive emulsion: T | 0.373 |
| | | Nucleating agent (1) | $1.143 \times 10^{-5}$ |
| | | Additive (22) | $4.231 \times 10^{-2}$ |

TABLE 31-continued

Constitution of Main materials for Light-Sensitive Element 301

| Number of layer | Name of layer | Additive | Coated amount ($g/m^2$) |
|---|---|---|---|
| | speed) | Additive (23) | $1.555 \times 10^{-2}$ |
| | | Additive (3) | $9.488 \times 10^{-3}$ |
| | | Additive (4) | $2.755 \times 10^{-2}$ |
| | | Additive (5) | $2.993 \times 10^{-2}$ |
| | | Additive (24) | $1.366 \times 10^{-4}$ |
| | | Additive (1) | $3.420 \times 10^{-3}$ |
| | | Surfactant (5) | $2.454 \times 10^{-2}$ |
| | | High-boiling organic solvent (2) | $3.069 \times 10^{-2}$ |
| | | Gelatin | 0.487 |
| | | Table 34 (continued from Table 31) | |
| 9th layer | Red-light-sensitive layer (low speed) | Internal-latent-image-type direct positive emulsion: E | 0.083 |
| | | Internal-latent-image-type direct positive emulsion: F | 0.083 |
| | | Nucleating agent (1) | $1.617 \times 10^{-5}$ |
| | | Additive (3) | $7.489 \times 10^{-3}$ |
| | | Additive (4) | $2.190 \times 10^{-2}$ |
| | | Additive (5) | $2.818 \times 10^{-2}$ |
| | | Additive (24) | $3.794 \times 10^{-4}$ |
| | | Additive (1) | $5.963 \times 10^{-3}$ |
| | | Surfactant (5) | $1.554 \times 10^{-2}$ |
| | | Gelatin | 0.260 |
| 8th layer | White reflection layer | Titanium dioxide | 1.684 |
| | | Additive (1) | $2.231 \times 10^{-3}$ |
| | | Surfactant (1) | $3.794 \times 10^{-4}$ |
| | | Additive (8) | $1.345 \times 10^{-3}$ |
| | | Additive (5) | $3.619 \times 10^{-2}$ |
| | | Additive (24) | $3.794 \times 10^{-4}$ |
| | | Additive (26) | $3.401 \times 10^{-2}$ |
| | | Gelatin | 0.655 |
| 7th layer | Cyan colored material layer | Cyan dye-releasing compound (1) | 0.1031 |
| | | Cyan dye releasing compound (2) | 0.1852 |
| | | High-boiling organic solvent (1) | $8.403 \times 10^{-2}$ |
| | | Additive (3) | $1.106 \times 10^{-2}$ |
| | | Additive (4) | $3.234 \times 10^{-2}$ |
| | | Additive (5) | $9.989 \times 10^{-3}$ |
| | | Additive (6) | $3.150 \times 10^{-2}$ |
| | | Additive (24) | $5.753 \times 10^{-4}$ |
| | | Additive (7) | $1.594 \times 10^{-2}$ |
| | | Surfactant (4) | $2.890 \times 10^{-2}$ |
| | | Additive (9) | $3.438 \times 10^{-3}$ |
| | | Additive (1) | $2.606 \times 10^{-3}$ |
| | | Hardener (3) | $1.053 \times 10^{-2}$ |
| | | Gelatin | 0.364 |
| 6th layer | Inter-mediate layer | Surfactant (1) | $2.136 \times 10^{-2}$ |
| | | Additive (1) | $1.170 \times 10^{-2}$ |
| | | Additive (5) | $1.309 \times 10^{-2}$ |
| | | Additive (24) | $5.691 \times 10^{-2}$ |
| | | Gelatin | 0.289 |
| 5th layer | Shading layer | Carbon black | 1.552 |
| | | Surfactant (1) | $2.578 \times 10^{-2}$ |
| | | Additive (1) | 1.331 |
| | | Additive (5) | $7.685 \times 10^{-2}$ |
| | | Additive (14) | $9.354 \times 10^{-2}$ |
| | | Additive (26) | $2.701 \times 10^{-2}$ |
| | | Gelatin | 0.878 |
| | | Table 35 (continued from Table 31) | |
| 4th layer | Inter-mediate layer | Surfactant (1) | $6.77 \times 10^{-4}$ |
| | | Additive (1) | $9.029 \times 10^{-3}$ |
| | | Additive (5) | $1.278 \times 10^{-2}$ |
| | | Additive (24) | $5.691 \times 10^{-5}$ |
| | | Hardener (1) | $2.132 \times 10^{-2}$ |
| | | Hardener (2) | $7.107 \times 10^{-5}$ |
| | | Gelatin | 0.289 |
| Third layer | White reflection layer | Titanium dioxide | 17.905 |
| | | Surfactant (1) | $1.464 \times 10^{-2}$ |
| | | Additive (1) | 0.144 |
| | | Additive (26) | $2.595 \times 10^{-2}$ |
| | | Gelatin | 2.802 |
| Second layer | Inter-mediate | Surfactant (7) | $1.286 \times 10^{-2}$ |
| | | Additive (5) | $1.167 \times 10^{-2}$ |

TABLE 31-continued

Constitution of Main materials for Light-Sensitive Element 301

| Number of layer | Name of layer | Additive | Coated amount ($g/m^2$) |
|---|---|---|---|
| | layer | Additive (24) | $8.167 \times 10^{-5}$ |
| | | Gelatin | 0.399 |
| First layer | Image-receiving layer | Polymer mordant (1) | 2.820 |
| | | Additive (17) | 0.2839 |
| | | Additive (5) | $8.172 \times 10^{-2}$ |
| | | Additive (24) | $5.721 \times 10^{-4}$ |
| | | Gelatin | 2.795 |
| Support (90 μm of polyethylene terephthalate undercoated and containing titanium dioxide for preventing light piping) | | | |
| Backing layer | Curl controlling layer | Ultraviolet absorber (4) | 0.40 |
| | | Ultraviolet absorber (5) | 0.10 |
| | | Diacetylcellulose (Acetylation degree 51%) | 4.20 |
| | | Additive (18) | 0.25 |
| | | Barium stearate | 0.11 |
| | | Hardener (4) | 0.50 |

TABLE 36

Content of sensitizing dyes per 1 kg of the emulsion

| Number of layer | Name of emulsion | Sensitizing dye type | Dye dispersion form | Temperature when added | Amount of dye g/1 kg emulsion |
|---|---|---|---|---|---|
| 22 | U | (9) | Aqueous solution | 70° C. | $9.38 \times 10^{-2}$ |
| | | (8) | Aqueous solution | | $1.19 \times 10^{-1}$ |
| 21 | A | (9) | Aqueous solution | 60° C. | $6.50 \times 10^{-2}$ |
| | | (8) | Aqueous solution | | $1.47 \times 10^{-1}$ |
| 21 | B | (9) | Aqueous solution | 60° C. | $7.31 \times 10^{-2}$ |
| | | (8) | Aqueous solution | | $1.66 \times 10^{-1}$ |
| 16 | T | (7) | Gelatin dispersion | 60° C. | $1.18 \times 10^{-1}$ |
| | | (4) | Gelatin dispersion | | $2.94 \times 10^{-3}$ |
| | | (6) | Dispersion of water/organic solvent with surfactant | | $9.23 \times 10^{-2}$ |
| 15 | C | (7) | Gelatin dispersion | 40° C. | $6.49 \times 10^{-2}$ |
| | | (4) | Gelatin dispersion | | $1.62 \times 10^{-3}$ |
| | | (6) | Dispersion of water/organic solvent with surfactant | | $4.85 \times 10^{-2}$ |
| 15 | D | (7) | Gelatin dispersion | 40° C. | $7.34 \times 10^{-2}$ |
| | | (4) | Gelatin dispersion | | $1.83 \times 10^{-3}$ |
| | | (6) | Dispersion of water/organic solvent with surfactant | | $5.69 \times 10^{-2}$ |
| 10 | T | (5) | Aqueous solution | 60° C. | $3.10 \times 10^{-2}$ |
| | | (4) | Gelatin dispersion | | $2.26 \times 10^{-2}$ |
| | | (3) | Gelatin dispersion | | $2.26 \times 10^{-2}$ |
| | | (2) | Gelatin dispersion | | $2.79 \times 10^{-3}$ |
| | | (1) | Gelatin dispersion | | $9.20 \times 10^{-2}$ |
| 9 | E | (5) | Aqueous solution | 60° C. | $1.63 \times 10^{-2}$ |
| | | (4) | Gelatin dispersion | | $1.34 \times 10^{-2}$ |
| | | (3) | Gelatin dispersion | | $1.34 \times 10^{-2}$ |
| | | (2) | Gelatin dispersion | | $1.91 \times 10^{-3}$ |
| | | (1) | Gelatin dispersion | | $6.32 \times 10^{-2}$ |
| 9 | F | (5) | Aqueous solution | 50° C. | $1.17 \times 10^{-2}$ |
| | | (4) | Gelatin dispersion | | $8.90 \times 10^{-3}$ |
| | | (3) | Gelatin dispersion | | $8.90 \times 10^{-3}$ |
| | | (2) | Gelatin dispersion | | $1.32 \times 10^{-3}$ |
| | | (1) | Gelatin dispersion | | $4.37 \times 10^{-2}$ |

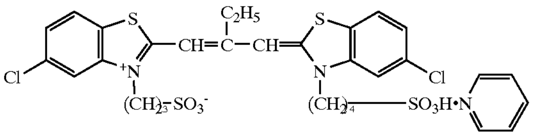

Molecular Weight: 728.77
Molecular formula: $C_{25}H_{26}Cl_2N_2O_6S_4.C_6H_5N_1$
Sensitizing dye (1)

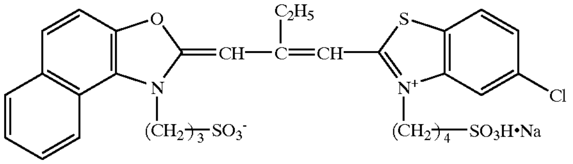

Molecular weight: 686.24
Molecular formula: $C_{30}H_{31}Cl_1N_2O_7S_3.NA_1$
Sensitizing dye (3)

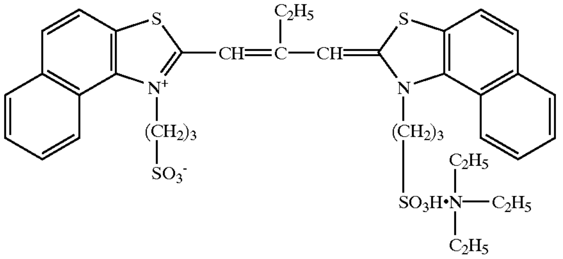

Molecular weight: 782.09
Molecular formula: $C_{33}H_{32}N_2O_6S_4.C_6H_{15}N_1$
Sensitizing dye (2)

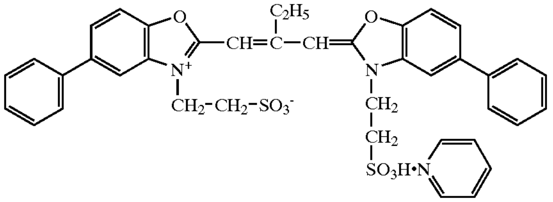

Molecular weight: 751.89
Molecular formula: $C_{33}H_{32}N_2O_8S_2.C_5H_5N_1$
Sensitizing dye (7)

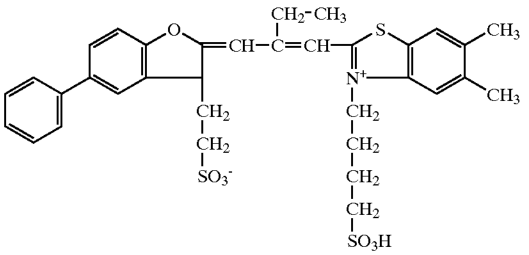

Molecular weight: 707.96
Molecular formula: $C_{33}H_{36}N_2O_7S_3.K_1$
Sensitizing dye (4)

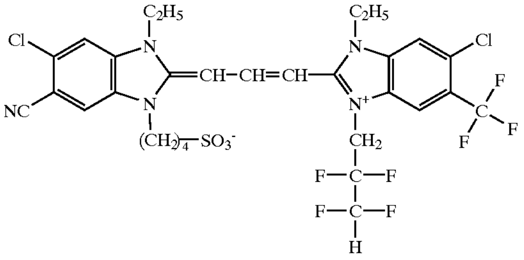

Molecular weight: 742.57
Molecular formula: $C_{30}H_{28}Cl_2F_7N_5O_3S_1$
Sensitizing dye (6)

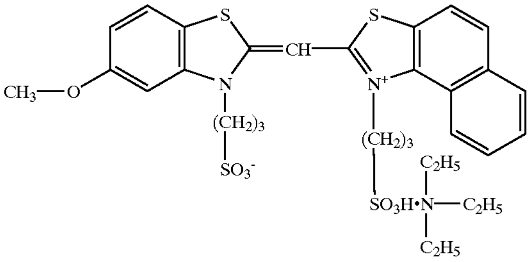

Molecular weight: 707.96
Molecular formula: $C_{26}H_{26}N_2O_7S_4.C_6H_5N_1$
Sensitizing dye (9)

-continued
| | | |
|---|---|---|
| 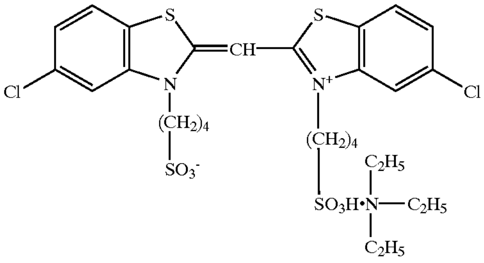 | Molecular weight: Molecular formula: Sensitizing dye (5) | 724.83 $C_{23}H_{24}Cl_2N_2O_6S_4 \cdot C_6H_{15}N_1$ |
| 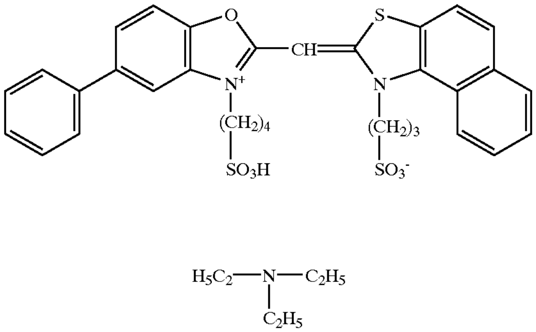 | Molecular weight: Molecular formula: Sensitizing dye (8) | 752.00 $C_{32}H_{30}N_2O_3S_3 \cdot C_6H_{15}N_1$ |
Color developing agent 1
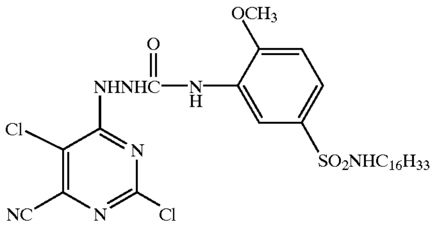
Compound (56) described in JP-A-9-152705
Yellow coupler 1
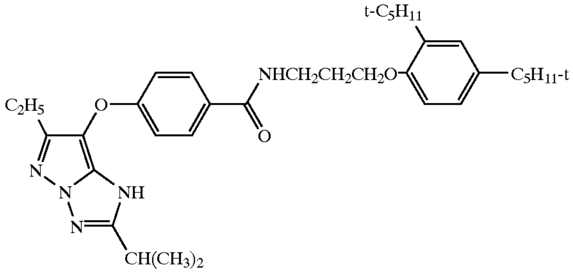
Compound (C-14) described in JP-A-9-152705

-continued
Magenta coupler 1
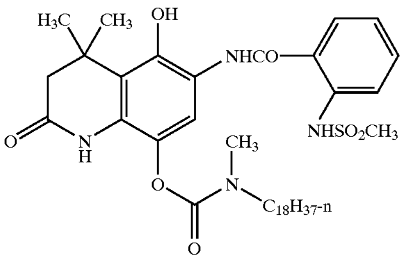
Compound (c-38) described in JP-A-9-152705
Cyan dye-releasing compound (1)
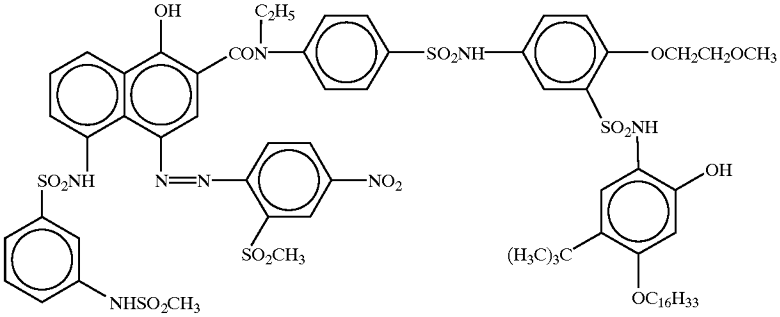
Cyan dye-releasing compound (2)
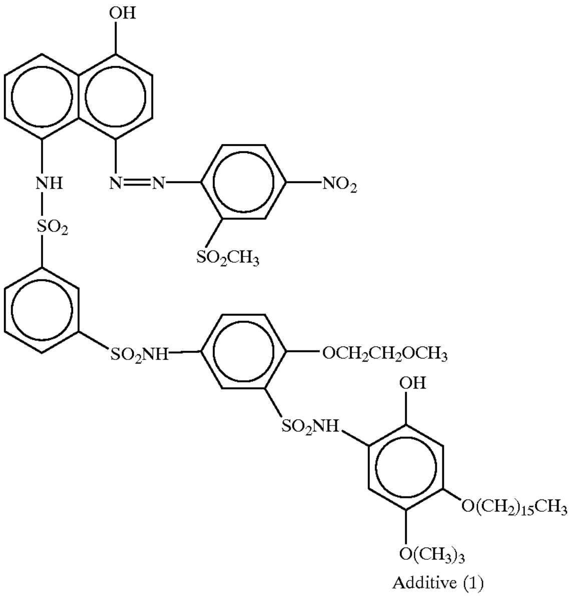
Additive (1)
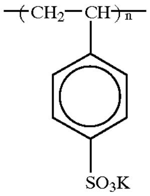
Additive (3)
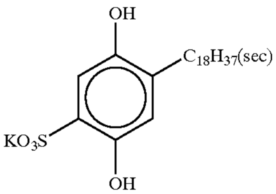

-continued
Additive (4)
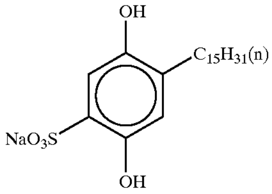
Additive (5)
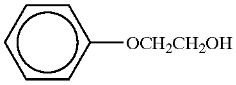
Additive (6)
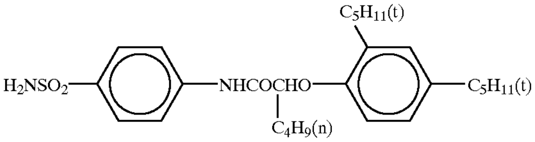
Additive (7)
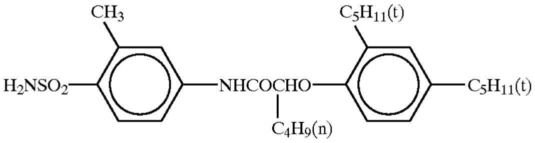
Additive (8)
Carboxymethyl cellulose
(CMC CELLOGEN 6A, trade name, manufactured by Dai-ichi Kogyo Seiyaku Co., Ltd.)
Additive (9)
Polyvinyl alcohol (PVA-220E, trade name)
Polymerization degree about 2,000; Saponification degree 88%
Additive (10)
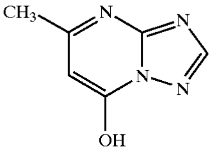
Additive (12)
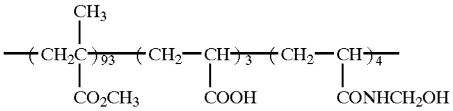
Additive (13)
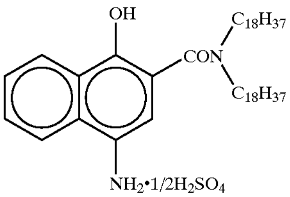
Additive (14)
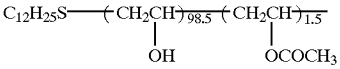

-continued
Additive (17)
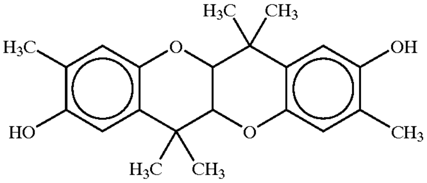
Additive (18)
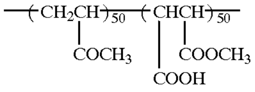
Additive (22)
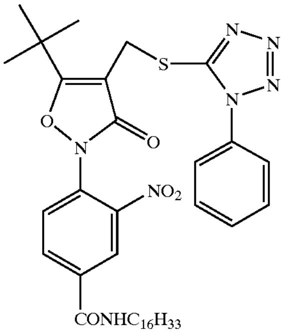
Additive (23)
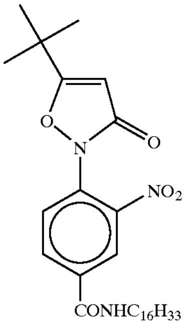
Color-mixing inhibitor (1)
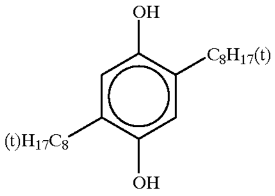
Additive (24)
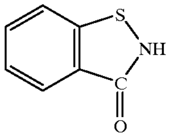
Additive (25)
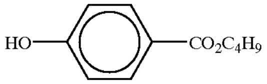

-continued
Additive (26)
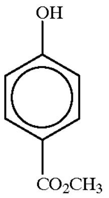
Matting agent(1)
Latex of sphere polymethyl methacrylate
(average particle diameter : 3 μm)
Surfactant (1)
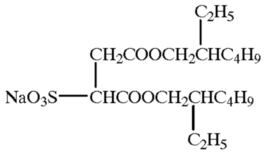
Surfactant (2)
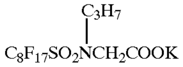
Surfactant (3)
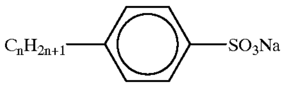
(n = 12.6)
Surfactant (4)
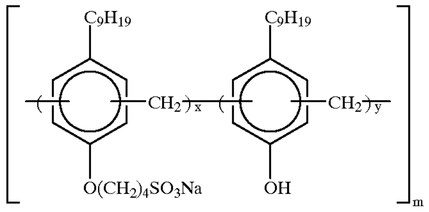
x/y = 4/6 m = 6.8
Surfactant (5)
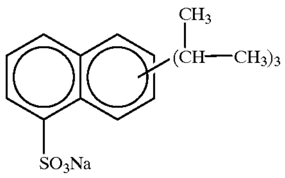
Surfactant (6)
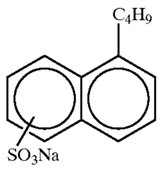
Surfactant (7)
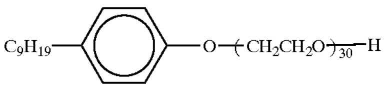
Ultra-violet absorbent (1)
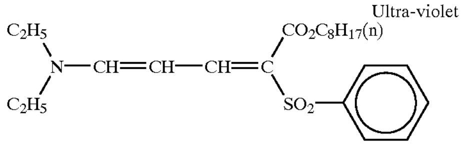

-continued
Ultra-violet absorbent (2)
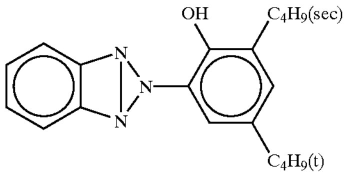
Ultra-violet absorbent (1)
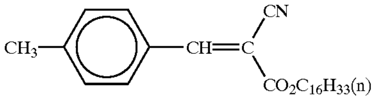
High-boiling organic solvent (1)
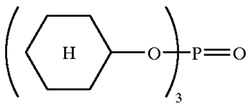
High-boiling organic solvent (2)
$-((iso)C_9H_{19}-O)_3-P=O$
Ultra-violet absorbent (4)
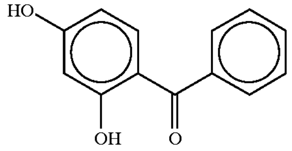
Ultra-violet absorbent (5)
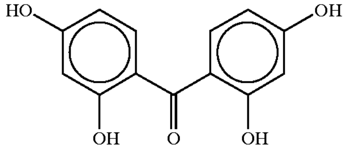
Hardener (1)
$CH_2=CHSO_2CH_2CONH(CH_2)_2NHCOCH_2SO_2CH=CH_2$
Hardener (2)
$CH_2=CHSO_2CH_2CONH(CH_2)_3NHCOCH_2SO_2CH=CH_2$
Hardener (3)
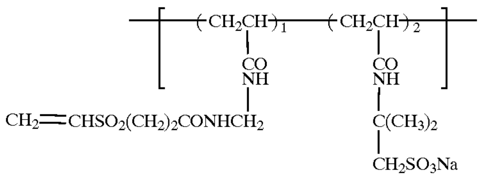
Hardener (4)
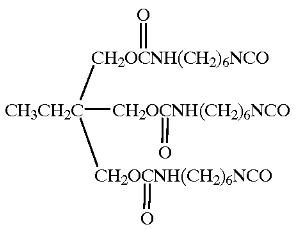

-continued

Nucleating agent (1)

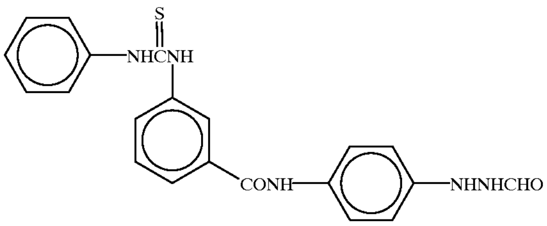

Polymer mordant (1)

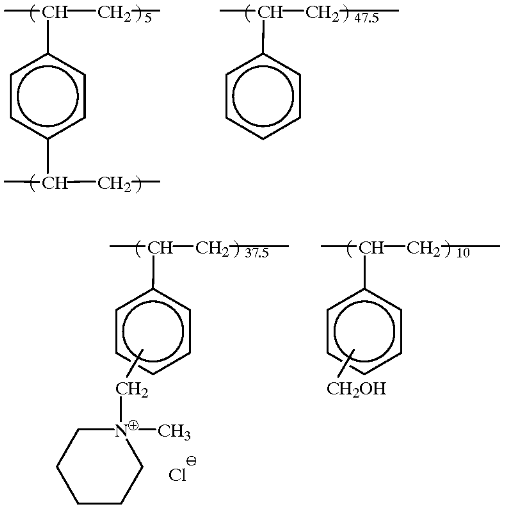

Formation of a Cover Sheet

Application was performed onto a transparent support having a thickness of 75 μm so as to have a layer structure shown in Table 37. Thus, a cover sheet was formed.

TABLE 37

Layer constitution of cover sheet

| Number of layer | Name of layer | Additive | Coated amount ($g/m^2$) |
|---|---|---|---|
| Third layer | Temperature compensating layer | Temperature compensating polymer (1) | 0.43 |
| | | Temperature compensating polymer (2) | 1.20 |
| | | Surfactant (8) | 0.0024 |
| Second layer | Alkali barrier layer | Acetylcellulose (Acetylation degree 51%) | 2.87 |
| | | Additive (19) | 0.20 |
| | | Additive (20) | 0.20 |
| | | Hardener (2) | 0.35 |
| First layer | Neutralization layer | Acid polymer (1) | 10.40 |
| | | Acetylcellulose (Acetylation degree 45%) | 0.70 |
| | | Hardener (5) | 0.049 |
| Support (75 μm of polyethylene terephthalate undercoated by gelatin and containing additive (21) for preventing light piping) | | | |
| Backing layer | Curl controlling layer | Acetylcellulose (Acetylation degree 55%) | 9.10 |
| | | Silica (average particle diameter: 3~4 μm) | 0.04 |

The following will show chemical structures of compounds to be used in the cover sheet.

Surfactant (8)

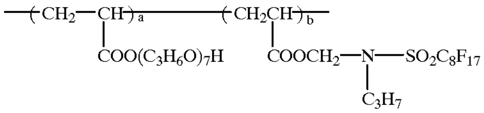

a/b was 6/4 (wt ratio)
Mw 30000~50000

Additive (19)

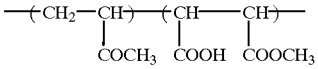

Additive (20)

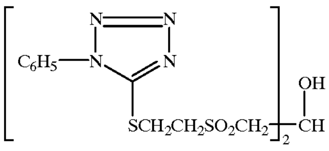

Hardener (5)

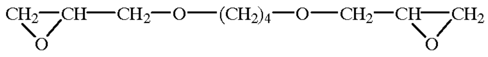

-continued

Additive (21)

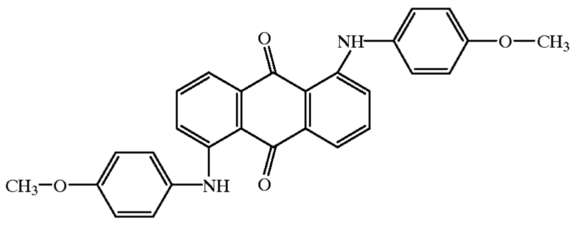

Temperature compensating polymer (1)

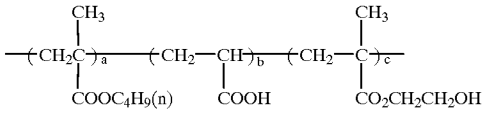

a/b/c = 66.1/5.5/28.4 (wt ratio)

-continued

Temperature compensating polymer (2)

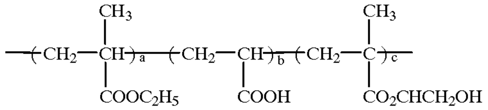

a/b/c = 66.1/5.5/28.4 (wt ratio)

Acid polymer (1)

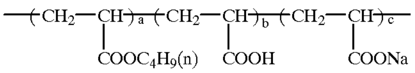

a/b/c = 20/76/4 (molar ratio)

The following will describe the formulation of an alkaline processing composition to be used.

| | |
|---|---|
| Silver nitrate | 0.10 g |
| Carbon black (Dai-nichi Seika Co.) | 160 g |
| Additive (27) | 8.60 g |
| Na salt of carboxymethyl cellulose | 58.0 g |
| Benzylalcohol | 2.50 g |
| Additive (28) | 2.10 g |
| Potassium sulfite (anhydride) | 1.90 g |
| 5-methylbenzotriazole | 2.50 g |
| 1-p-tolyl-4-hydroxymethyl-4-methyl-3-pyrazolidone | 7.00 g |
| 1-phenyl-4-hydroxymethyl-4-methyl-3-pyrazolidone | 10.0 g |
| Potassium hydroxide | 56.0 g |
| Aluminum nitrate | 0.60 g |
| Zinc nitrate | 0.60 g |
| Additive (29) | 6.60 g |
| Additive (14) | 1.80 g |
| 1,2-benzisothiazoline-3-one | 0.003 g |

Additive (27)

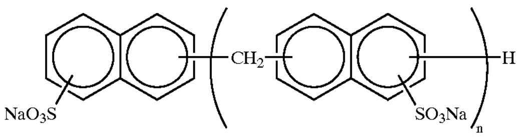

Additive (28)

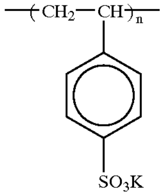

-continued

Additive (29)

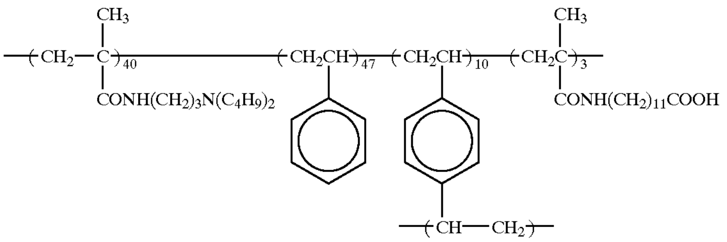

Preparation of Light-Sensitive Materials 302–304

Light-sensitive materials 302–304 were prepared in the same manner as in the preparation of the light-sensitive material 301, except that the color-developing agents and the couplers in the 13th layer and the 19th layer of the light-sensitive material 301 were replaced by equivalent moles of the following color-developing agents and couplers shown in Table 38.

TABLE 38

| Sample No. | Color developing agent of 13th layer | Coupler of 13th layer | Color developing agent of 19th layer | Coupler of 19th layer | Remarks |
|---|---|---|---|---|---|
| 301 | Color developing agent ① | Magenta coupler ① | Color developing agent ① | Yellow coupler ① | Comparative example |
| 302 | R40 | Cp-13 | R40 | Cp-11 | This invention |
| 303 | R41 | Cp-14 | R22 | Cp-11 | This invention |
| 304 | R42 | Cp-13 | R40 | Cp-12 | This invention |

Then, each of the light-sensitive elements 301–304 was subjected to gray exposure from the side of the emulsion layer through a continuous wedge. Subsequently the cover sheet was put on the exposed element and then a pressing roller was used to develop the alkaline processing composition between the sheet and the element to have a thickness of 55 μm. The processing was performed at 25° C. After two hours, the highest transfer densities of yellow and magenta were measured with a color densitometer. Furthermore, after irradiation with a fluorescent lamp having an illuminance of 17,000 lux for 2 weeks, the highest transfer densities of yellow and magenta were also measured.

Measured results are shown in Table 39.

TABLE 39

| Sample | Maximum transferred density after 2 hours | | Maximum transferred density after 2 weeks irradiation with fluorescent lamp | | |
|---|---|---|---|---|---|
| No. | Yellow | Magenta | Yellow | Magenta | Remarks |
| 301 | 1.57 | 1.82 | 0.56 | 0.54 | Comparative example |
| 302 | 1.80 | 2.05 | 165 | 1.83 | This invention |
| 303 | 1.92 | 2.25 | 1.85 | 1.99 | This invention |
| 304 | 1.89 | 2.23 | 1.74 | 1.94 | This invention |

As is apparent from comparison with the sample 301 (Comparative example) with the samples 302, 303 and 304 (This invention), the compounds of the present invention were superior in color-forming property and image stability than known compounds.

Example 2-1

A dye fixation material (image-receiving element) R101 was formed in the same manner as in the above Example 1-1, except that in Example 2-1, the following was used as the anionic surfactant (2).

Anionic surfactant (2)

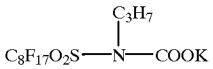

Then, a light-sensitive material for heat-development was produced by the following method.

The light-sensitive silver halide emulsions, and the colloidal silver emulsion dispersion were made in the same manner as in the above Example 1-1, except that in the preparation of the Light-sensitive silver halide emulsion (3), the sensitizing dye ③ (that was added in the Example 1-1 at the time of chemical sensitization) was not added.

Then, the preparation methods of gelatin dispersions of hydrophobic additives are described.

Gelatin dispersions of a yellow-dye-providing compound, a magenta-dye-providing compound, and a cyan-dye-providing compound, whose formulations are shown in Table 40, were prepared, respectively. That is, the oil phase components were dissolved by heating to about 70° C., to form a uniform solution, and to the resultant solution, were added the aqueous phase components that had been heated to about 60° C., followed by stirring to mix and dispersing by a homogenizer for 10 min at 10,000 rpm. To the resultant dispersion, was added additional water, followed by stirring, to obtain a uniform dispersion.

Furthermore, the gelatin dispersion of the cyan dye-providing compound was subjected to ultrafiltration using an ultrafiltration module (ultrafiltration module: ACV-3050, trade name, made by Asashi Chemical Co., Ltd.), so that the amount thereof would be 1/17.6 of the amount of ethyl acetate shown in Table 40.

TABLE 40

| | | Composition of dispersion | | |
|---|---|---|---|---|
| | | Yellow | Magenta | Cyan |
| Oil phase | Yellow-dye-providing compound ① | 1.68 g | None | None |
| | Yellow-dye-providing compound ② | 4.03 g | None | None |
| | Cyan-dye-providing compound ① | None | None | 4.45 g |
| | Magenta-dye-providing | None | 5.27 g | None |

TABLE 40-continued

| | | Composition of dispersion | | |
|---|---|---|---|---|
| | | Yellow | Magenta | Cyan |
| | compound ① | | | |
| | Reducing agent ① | 0.47 g | 0.06 g | 0.29 g |
| | Antifoggant ③ | 0.1 g | None | 0.06 g |
| | Antifoggant ④ | None | 0.021 g | None |
| | Surfactant ① | 0.6 g | 0.23 g | 0.45 g |
| | High-boiling solvent ① | 0.84 g | None | 1.34 g |
| | High-boiling solvent ② | 2.01 g | 2.63 g | 4.47 g |
| | Development accelerator ① | 1.01 g | None | None |
| | Dye (a) | 0.59 g | None | 0.14 g |
| | Water | 0.19 ml | None | 0.3 g |
| | Ethyl acetate | 10 ml | 16 ml | 16 ml |
| Aqueous phase | Lime-processed gelatin | 5.5 g | 3.1 g | 2.4 g |
| | Calcium nitrate | 0.05 g | 0.04 g | None |
| | Surfactant ① | None | None | None |
| | Sodium hydroxide aq. soln. (1 mol/l) | None | None | 0.07 g |
| | Carboxymethyl cellulose | None | None | 31 g |
| | Water | 35 ml | 31 ml | 40 ml |
| | Water (after emulsification) | 40 ml | 43 ml | 0.03 ml |
| | Antiseptic ① | 0.003 g | 0.002 g | None |

A gelatin dispersion of Antifoggant ④ whose formulation is shown in Table 41 was prepared. That is, the oil phase components were dissolved by heating to about 60° C. to form a solution, and to the resultant solution, were added the aqueous phase components that had been heated to about 60° C., and after stirring and mixing them, the resultant mixture was dispersed for 10 min at 10,000 rpm by a homogenizer, to obtain a uniform dispersion.

TABLE 42

| | | Composition of dispersion |
|---|---|---|
| Oil phase | Antifoggant ④ | 0.8 g |
| | Reducing agent ① | 0.1 g |
| | High-boiling solvent ② | 2.3 g |
| | High-boiling solvent ⑤ | 0.2 g |
| | Surfactant ① | 0.5 g |
| | Surfactant ④ | 0.5 g |
| | Ethyl acetate | 10.0 ml |
| Aqueous phase | Acid-processed gelatin | 10.0 g |
| | Antiseptic ① | 0.004 g |
| | Calcium nitrate | 0.1 g |
| | Water | 35.0 ml |
| | Additional Water | 46 ml |

A gelatin dispersion of Reducing Agent ② whose formulation is shown in Table 42 was prepared. That is, the oil phase components were dissolved by heating to about 60° C. to form a solution, and to the resultant solution, were added the aqueous phase components that had been heated to about 60° C., and after stirring and mixing them, the resultant mixture was dispersed for 10 min at 10,000 rpm by a homogenizer, to obtain a uniform dispersion. From the thus-obtained dispersion, ethyl acetate was removed off using a vacuum organic solvent removing apparatus.

TABLE 43

| | | Composition of dispersion |
|---|---|---|
| Oil phase | Reducing agent ② | 7.5 g |
| | High-boiling solvent ① | 4.7 g |
| | Surfactant ① | 1.9 g |
| | Ethyl acetate | 14.4 ml |

TABLE 43-continued

| | | Composition of dispersion |
|---|---|---|
| Aqueous phase | Acid-processed gelatin | 10.0 g |
| | Antiseptic ① | 0.002 g |
| | Antiseptic ④ | 1.004 g |
| | Calcium nitrate | 2.1 g |
| | Water | 136.7 ml |

A dispersion of Polymer Latex (a) whose formulation is shown in Table 43 was prepared. That is, while a mixed solution of Polymer Latex (a), Surfactant ⑤, and water whose amounts are shown in Table 43 was stirred, Anionic Surfactant ⑥ was added thereto, over 10 min, to obtain a uniform dispersion. The resulting dispersion was repeatedly diluted with water and concentrated using a ultrafiltration module (Ultrafiltration Module: ACV-3050, trade name, manufactured by Asahi Chemical Industry Co., Ltd.), to bring the salt concentration of the dispersion to 1/9, thereby obtaining a dispersion.

TABLE 43

| | Composition of dispersion |
|---|---|
| Polymer Latex (a) aqueous solution (solid content 13%) | 108 ml |
| Surfactant ⑤ | 20 g |
| Anionic surfactant ⑥ aqueous solution (5%) | 600 ml |
| Water | 1232 ml |

A gelatin dispersion of Stabilizer ① whose formulation is shown in Table 44 was prepared. That is, the oil phase components were dissolved at room temperature to form a solution, and to the resultant solution, were added the aqueous phase components that had been heated to about 40° C., and after stirring and mixing them, the resultant mixture was dispersed for 10 min at 10,000 rpm by a homogenizer. To the resultant dispersion, was added additional water, followed by stirring, thereby obtaining a uniform dispersion.

TABLE 44

| | | Composition of dispersion |
|---|---|---|
| Oil phase | Stabilizer① | 4.0 g |
| | Sodium hydroxide | 0.3 g |
| | Methanol | 62.8 g |
| | High-boiling solvent | 0.9 g |
| Aqueous phase | Gelatin from which calcium had been removed (Ca content 100 ppm or less) | 10 g |
| | Antiseptic① | 0.04 g |
| | Water | 320.5 ml |

A gelatin dispersion of zinc hydroxide was prepared according to the formulation shown in Table 45. That is, after the components were mixed and dissolved, dispersing was carried out for 30 min in a mill, using glass beads having an average particle diameter of 0.75 mm. Then the glass beads were separated and removed off, to obtain a uniform dispersion. (Zinc hydroxide having a grain size of 0.25 μm was used.)

TABLE 45

| | Composition of dispersion |
|---|---|
| Zinc hydroxide | 15.9 g |
| Carboxymethyl cellulose | 0.7 g |
| Poly(sodium acrylate) | 1.07 g |
| Lime-processed gelatin | 4.2 g |
| Water | 100 ml |
| High-boiling solvent ② | 0.4 g |

The preparation method of a gelatin dispersion of a matt agent that was to be added to the protective layer is described.

A solution containing PMMA dissolved in methylene chloride was added, together with a small amount of a surfactant, to gelatin, and they were stirred and dispersed at high speed. Then the methylene chloride was removed off using a vacuum solvent removing apparatus, to obtain a uniform dispersion having an average particle size of 4.3 μm.

Yellow-dye-providing compound 1

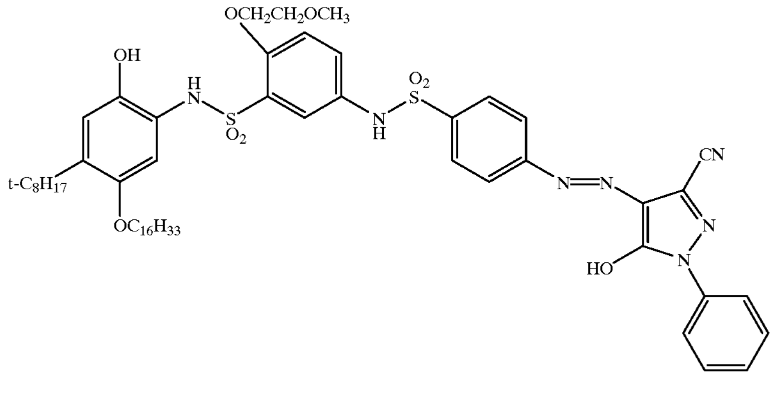

Yellow-dye-providing compound 2

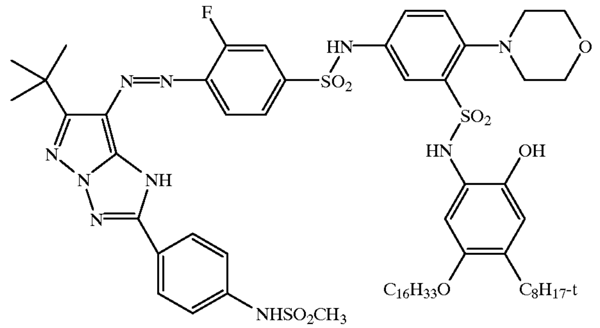

Cyan-dye-providing compound 1

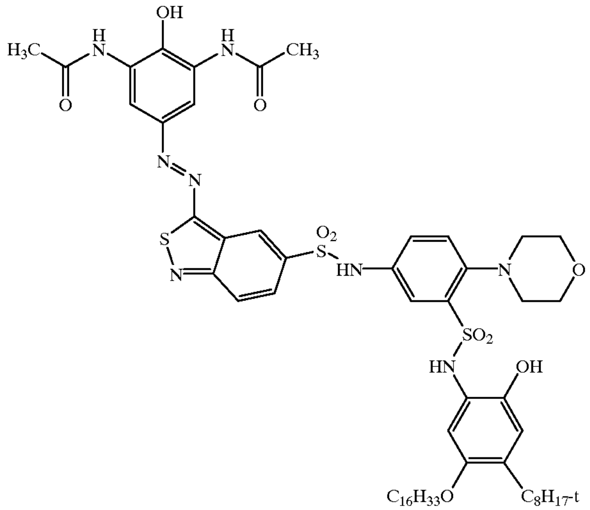

-continued
Dye (a)
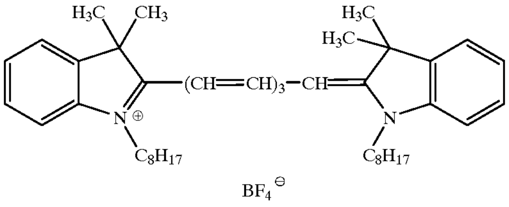
Magenta-dye-providing compound 1
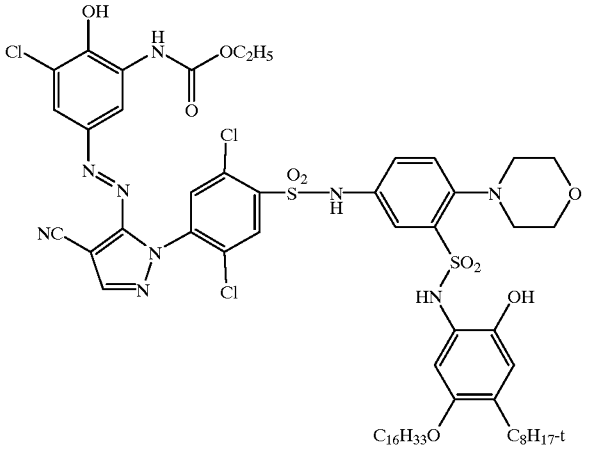
Reducing agent 1
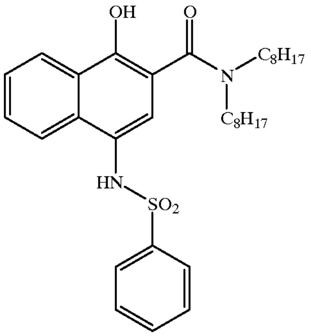
Antifoggant 3
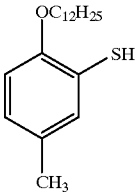
Antifoggant 4
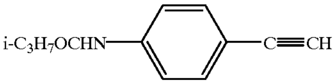
Surfactant 1
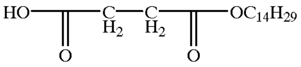
Development accelerator 1
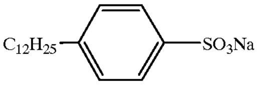
High-boiling organic solvent 1
$(C_4H_9(C_2H_5)CHCH_2O)_3—P{=}O$
Antiseptic 1
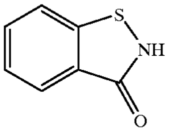
High-boiling organic solvent 2
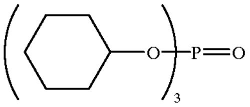
Reducing agent 2
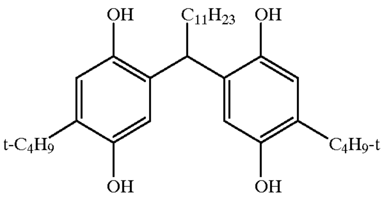
Antiseptic 4
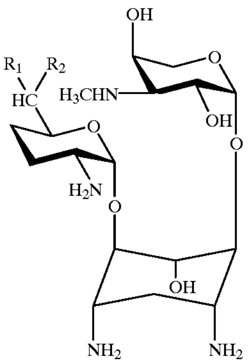
| $R_1$ | $R_2$ |
|---|---|
| $CH_3$ | $NHCH_3$ |
| $CH_3$ | $NH_2$ |
| H | $NH_2$ |
| H | $NHCH_3$ |

-continued

Water-soluble polymer 1

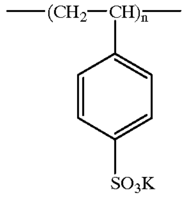

Limiting viscosity number [η] = 1.6
(0.1 mol/l NaCl 30° C.)
Molecular weight = 1,000,000

Water-soluble polymer 2

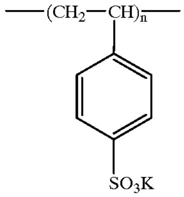

Limiting viscosity number [η] = 0.8
(0.1 mol/l NaCl 30° C.)
Molecular weight = 400,000

Sensitizing dye 3

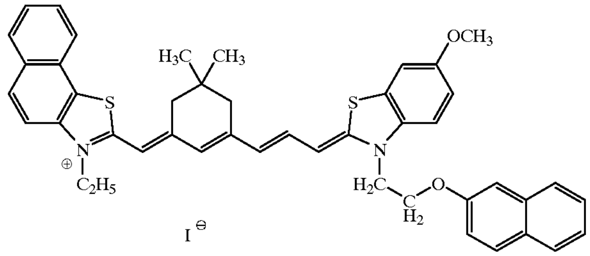

Hardener 1

$CH_2{=}CHSO_2CH_2SO_2CH{=}CH_2$

Surfactant 2

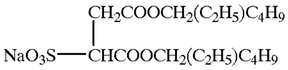

Surfactant 3

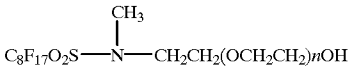

n = 15

Surfactant 7

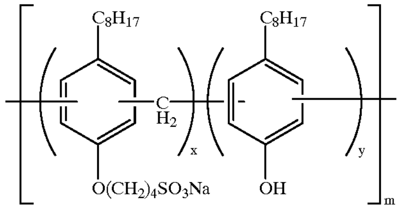

x:y = 4:6 m = 6.8

High-boiling organic solvent 5

$C_{26}H_{46.9}Cl_{7.1}$
EMPARA 40 (trade name: manufactured by Ajinomoto K.K.)

Polymer Latex a

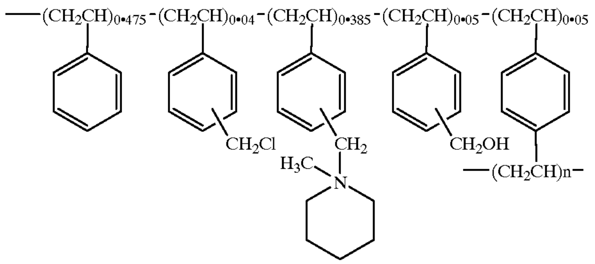

Surfactant 4

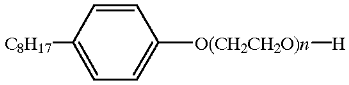

n = 20

Surfactant 5

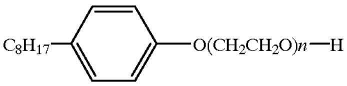

n = 50

Surfactant 6

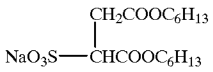

Antifoggant 5

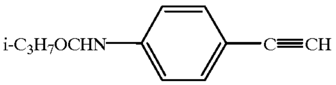

Using the above materials, Light-Sensitive Material shown in Tables 46 and 47 was prepared.

TABLE 46

Constitution of Main Materials of Light-Sensitive Material 1101

| Number of layer | Name of layer | Additive | Added amount ($mg/m^2$) |
|---|---|---|---|
| Seventh layer | Protective layer | Acid-processed gelatin | 378 |
| | | Reducing agent (2) | 70 |
| | | High-boiling solvent (1) | 44 |
| | | Colloidal silver grains | 2 |
| | | Matting agent (PMMA resin) | 17 |
| | | Surfactant (1) | 19 |
| | | Surfactant (2) | 16 |
| | | Surfactant (3) | 2 |
| | | Surfactant (4) | 12 |
| | | Surfactant (6) | 17 |
| | | Dispersion of Polymer Latex a | 14 |
| | | Calcium nitrate | 5 |
| Sixth layer | Intermediate layer | Lime-processed gelatin | 882 |
| | | Zinic hydroxide | 577 |
| | | Antifoggant (4) | 18 |
| | | Reducing agent (1) | 2 |
| | | High-boiling solvent (2) | 54 |
| | | High-boiling solvent (5) | 6 |
| | | Surfactant (1) | 1 |
| | | Surfactant (2) | 0.5 |
| | | Surfactant (7) | 11 |
| | | Water-soluble polymer (1) | 5 |
| | | Calcium nitrate | 17 |
| Fifth layer | 680 nm-light-sensitive layer | Lime-processed gelatin | 428 |
| | | Light-sensitive silver halide emulsion (1) | 287 |
| | | Magenta-dye-providing compound (1) | 487 |
| | | High-boiling solvent (2) | 244 |
| | | Reducing agent (1) | 18 |
| | | Antifoggant (4) | 20 |
| | | Surfactant (1) | 22 |
| | | Water-soluble polymer (1) | 11 |
| Forth layer | Intermediate layer | Lime-processed gelatin | 416 |
| | | Zinic hidroxide | 271 |
| | | Antifoggant (4) | 8 |
| | | Reducing agent (1) | 1 |
| | | High-boiling solvent (2) | 25 |
| | | High-boiling solvent (5) | 378 |
| | | Surfactant (1) | 5 |
| | | Surfactant (2) | 0.3 |
| | | Surfactant (7) | 5 |
| | | Water-soluble polymer (1) | 2 |
| | | Calcium nitrate | 8 |

TABLE 47

(continued from Table 46)

| Number of layer | Name of layer | Additive | Added amount ($mg/m^2$) |
|---|---|---|---|
| Third layer | 750 nm-light-sensitive layer | Lime-processed gelatin | 404 |
| | | Light-sensitive silver halide emulsion (2) | 184 |
| | | Stabilizer (1) | 8 |
| | | Cyan-dye-providing compound (1) | 428 |
| | | Dye (a) | 13 |
| | | High-boiling solvent (1) | 128 |
| | | High-boiling solvent (2) | 429 |
| | | Reducing agent (1) | 56 |
| | | Antifoggant (3) | 5 |
| | | Surfactant (1) | 43 |
| | | Carboxymethyl cellulose | 7 |
| | | Water-soluble polymer (1) | 9 |
| Second layer | Intermediate layer | Lime-processed gelatin | 708 |
| | | Antifoggant (5) | 4 |
| | | Reducing agent (1) | 2 |
| | | Surfactant (2) | 104 |
| | | Surfactant (5) | 14 |
| | | Calcium nitrate | 5 |

TABLE 47-continued (continued from Table 46)

| Number of layer | Name of layer | Additive | Added amount (mg/m$^2$) |
|---|---|---|---|
| First layer | 810 nm-light-sensitive layer | Lime-processed gelatin | 569 |
| | | Light-sensitive silver halide emulsion (3) | 330 |
| | | Fine-grain silver chloride emulsion | 30 |
| | | Stabilizer ① | 8 |
| | | Yellow-dye-providing compound ① | 119 |
| | | Yellow-dye-providing compound ② | 285 |
| | | Sensitizing dye ③ | 0.1 |
| | | Dye (a) | 42 |
| | | High-boiling solvent ① | 59 |
| | | High-boiling solvent ② | 143 |
| | | Surfactant ① | 41 |
| | | Reducing agent ① | 66 |
| | | Development accelerator ① | 71 |
| | | Antifoggant ③ | 6 |
| | | Water-soluble polymer ② | 41 |
| | | Hardener ① | 45 |

Support (Paper support whose both surfaces were laminated with polyethylene: thickness 135 μm)

Light-sensitive materials 1102 and 1103 were formed in the same manner as the light-sensitive material 1101, except that the gelatin dispersion of the magenta dye-providing compound of the fifth layer in the light-sensitive material 1101 was changed to each gelatin dispersion of dye-providing compound shown in the following Table 48.

Light-sensitive materials 1104 and 1105 were formed in the same manner as the light-sensitive material 1101, except that the gelatin dispersion of the yellow dye-providing compounds of the first layer in the light-sensitive material 1101 was changed to each gelatin dispersion of dye-providing compound shown in the following Table 48.

TABLE 48

| Light-sensitive material | Yellow-dye-providing compound | Magenta-dye-providing compound | Remarks |
|---|---|---|---|
| 1101 | Yellow-dye-providing compound ①<br>Yellow-dye-providing compound ② | Magenta-dye-providing compound ① | Comparative example |
| 1102 | — | K-1 | This invention |
| 1103 | — | K-4 | This invention |
| 1104 | K-7 | — | This invention |
| 1105 | K-10 | — | This invention |

Notes) "—" indicates that no change from the sample 1101 was performed.

Each of the light-sensitive materials 1101 to 1105 was combined with the dye fixation material R101, and then the combination was subjected to exposure to light and development, using PICTROGRAPHY 3000 (trade name) made by Fuji Photo Film Co., Ltd., to obtain an image on the image-receiving material.

A densitometer X rite 404, (trade name) made by X rite company, was used to measure the reflection density of the image. The maximum density (Dmax) and the minimum density (Dmin) of each of magenta and yellow were measured and evaluated.

The images obtained from the light-sensitive materials were irradiated with Xenon light having an illumination of 170,000 lux for a week. On the portions having a magnet density or a yellow density of 1.0, dye remaining rates were obtained. The results are shown in Table 49.

TABLE 49

| Light-sensitive material | Dmax | Dmin | Residual rate of dye (%) | Hue | Remarks |
|---|---|---|---|---|---|
| 1101 | 2.12 | 0.16 | 88.7 | Magenta | Comparative example |
| 1102 | 2.42 | 0.14 | 88.2 | Magenta | This invention |
| 1103 | 2.25 | 0.14 | 86.7 | Magenta | This invention |
| 1101 | 1.96 | 0.14 | 90.7 | Yellow | Comparative example |
| 1104 | 2.2 | 0.12 | 90 | Yellow | This invention |
| 1105 | 2.14 | 0.1 | 92.4 | Yellow | This invention |

The results in Table 49 demonstrate that the compound of the present invention had both of high developed color density and excellent fastness to light.

Example 2-2

Each of the compound examples (K-2), (K-5), (K-8) and (K-11) was used and evaluated in the same manner as in Examples described in JP-A-8-137072. As a result, it was found that the compound of the present invention had both the high developed color density and the high fastness to light.

Example 2-3

Each of the compound examples (K-3), (K-6), (K-9) and (K-12) was used and evaluated in the same manner as in Examples described in JP-A-6-332131. As a result, it was found that the compound of the present invention had a sharpness-improving effect and further had high developed color density and high fastness to light.

Example 2-4

The absorbances of the exemplified dye (DYE-7) and the dye for comparison (D-1) in N,N-dimethylformamide were measured. The results thereof are shown in FIG. 1. FIG. 1 demonstrates that the dye of the present invention exhibited a good absorbance property.

Dye for comparison (D-1)

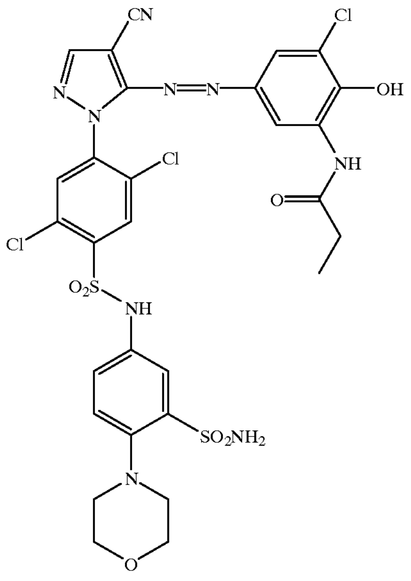

Having described our invention as related to the present embodiments, it is our intention that the invention not be limited by any of the details of the description, unless otherwise specified, but rather be construed broadly within its spirit and scope as set out in the accompanying claims.

What we claim is:

1. A color-developing agent, represented by the following formula (1-1):

formula (1-1)

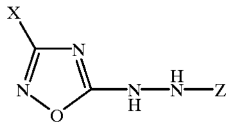

wherein X represents a hydrogen atom or a substituent with the proviso that X is not a phenyl group, and Z represents a carbamoyl, acyl, alkoxycarbonyl, or aryloxycarbonyl group.

2. The color-developing agent as claimed in claim 1, wherein X in the formula (1-1) is a substituent further comprising at least one substituent selected from the group consisting of —COOH, —$NHSO_2R$, —$SO_2NHR$, —$SO_2NHCOR$, —$CONHSO_2R$, —$NHCONHSO_2R$, —$SO_2NHCONRR$, —OH and —SH, in which R represents an alkyl, aryl or aromatic heterocyclic group which may be substituted, and R's may be the same or different from each other and may bond together to form a ring.

3. The color-developing agent as claimed in claim 1, wherein Z in the formula (1-1) is a carbamoyl group, in which the nitrogen atom on the carbamoyl group has at least one hydrogen atom.

4. A color-developing agent, represented by the following formula (1-1):

formula (1-1)

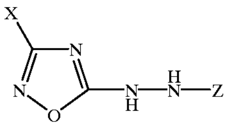

wherein X represents a hydrogen atom or a substituent selected from the group consisting of halogen atoms, noncyclic alkyl, cycloalkyl, bicycloalkyl, alkyl having a tricyclo structure or higher structure, noncyclic alkenyl, cycloalkenyl, bicycloalkenyl, alkynyl, naphthyl, substituted aryl, heterocyclic , cyano, hydroxyl, nitro, carboxyl, alkoxy, aryloxy, silyloxy, heterocyclic oxy, acyloxy, carbamoyloxy, alkoxycarbonyloxy, aryloxycarbonyloxy, amino, acylamino, aminocarbonylamino, alkoxycarbonylamino, aryloxycarbonylamino, sulfamoylamino, alkyl- and aryl-sulfonylamino, mercapto, alkylthio, arylthio, heterocyclic thio, sulfamoyl, sulfo, alkyl- and aryl-sulfinyl, alkyl- and aryl-sulfonyl, acyl, aryloxycarbonyl, alkoxycarbonyl, carbamoyl, arylazo and heterocyclic azo, imido, phosphino, phosphinyl, phosphinyloxy, phosphinylamino and silyl, and Z represents a carbamoyl, acyl, alkoxycarbonyl, or aryloxycarbonyl group.

5. A color-developing agent, represented by the following formula (1-1):

formula (1-1)

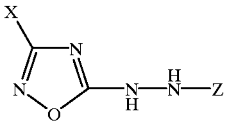

wherein x in the formula (1-1) is a hydrogen atom or a substituent further comprising at least one substituent selected from the group consisting of —COOH, —$NHSO_2R$, —$SO_2NHR$, —$SO_2NHCOR$, —$CONHSO_2R$, —$NHCONHSO_2R$, —$SO_2NHCONRR$, —OH and —SH, in which R represents an alkyl, aryl or aromatic heterocyclic group which may be substituted, and R's may be the same or different from each other and may bond together to form a ring, and Z represents a carbamoyl, acyl, alkoxycarbonyl, or aryloxycarbonyl group.

6. The color-developing agent as claimed in claim 5 wherein Z in the formula (1-1) is a carbamoyl group, in which the nitrogen atom on the carbamoyl group has at least one hydrogen atom.

7. The color-developing agent as claimed in claim 1, wherein the substituent is fluorine, chlorine, bromine, iodine, noncyclic alkyl having 1–30 carbon atoms, substituted or unsubstituted cycloalkyl having 3–30 carbon atoms, substituted or unsubstituted bicycloalkyl having 5–30 carbon atoms, substituted or unsubstituted alkenyl having 2–30 carbon atoms, substituted or unsubstituted cycloalkenyl having 3–30 carbon atoms, substituted or unsubstituted bicycloalkenyl having 5–30 carbon atoms, substituted or unsubstituted alkynyl having 2–30 carbon atoms, substituted aryl having 6–30 carbon atoms, monovalent groups obtained by removing one hydrogen atom from 5- or 6-membered and substituted or unsubstituted and aromatic or non-aromatic heterocyclic compounds, cyano, hydroxyl, nitro, carboxyl, substituted or unsubstituted alkoxy having 1–30 carbon atoms, substituted or unsubstituted aryloxy having 6–30 carbon atoms, silyloxy having 3–20 carbon atoms, substituted or unsubstituted heterocyclic oxy having 2–30 carbon atoms, formyloxy, substituted or unsubstituted alkylcarbonyloxy having 2–30 carbon atoms, and substituted or unsubstituted arylcarbonyloxy having 6–30 carbon atoms, substituted or unsubstituted carbamoyloxy having 1–30 carbon atoms, substituted or unsubstituted alkoxycarbonyloxy having 2–30 carbon atoms, substituted or unsubstituted aryloxycarbonyloxy having 7–30 carbon atoms, amino, substituted or unsubstituted alkylamino having 1–30 carbon atoms, and substituted or unsubstituted anilino having 6–30 carbon atoms, formylamino, substituted or unsubstituted alkylcarbonylamino having 1–30 carbon atoms, and substituted or unsubstituted arylcarbonylamino having 6–30 carbon atoms, substituted or unsubstituted aminocarbonylamino having 1–30 carbon atoms, substituted or unsubstituted alkoxycarbonylamino having 2–30 carbon atoms, substituted or unsubstituted aryloxycarbonylamino having 7–30 carbon atoms, substituted or unsubstituted sulfamoylamino having 0–30 carbon atoms, substituted or unsubstituted alkylsulfonylamino having 1–30 carbon atoms, and substituted or unsubstituted arylsulfonylamino having 6–30 carbon atoms, mercapto, substituted or unsubstituted alkylthio having 1–30 carbon atoms, substituted or unsubstituted arylthio having 6–30 carbon atoms, substituted or unsubstituted heterocyclic thio having 2–30 carbon atoms, substituted or unsubstituted sulfamoyl having 0–30 carbon atoms, substituted or unsubstituted alkylsulfinyl having 1–30 carbon atoms, and substituted or unsubstituted arylsulfinyl having 6–30 carbon atoms, substituted or unsubstituted alkylsulfonyl having 1–30 carbon atoms, and substituted or unsubstituted arylsulfonyl having 6–30 carbon atoms, formyl, substituted or unsubstituted alkylcarbonyl having 2–30 carbon atoms, and substituted or unsubstituted arylcarbonyl having 7–30 carbon atoms, substituted or unsubstituted aryloxycarbonyl having 7–30 carbon atoms, substituted or unsubstituted alkoxycarbonyl having 2–30 carbon atoms, substituted or unsubstituted carbamoyl having 1–30 carbon atoms, substituted or unsubstituted arylazo having 6–30 carbon atoms, and substituted or unsubstituted heterocyclic azo having 3–30 carbon atoms, N-succimido, and N-phthalimido, substituted or unsubstituted phosphino having 2–30 carbon atoms, substituted or unsubstituted phosphinyl having 2–30 carbon atoms, substituted or unsubstituted phosphinyloxy having 2–30 carbon atoms, substituted or unsubstituted phosphinylamino having 2–30 carbon atoms, substituted or unsubstituted silyl having 3–30 carbon atoms.

* * * * *